US010274466B2

(12) United States Patent
McDonald et al.

(10) Patent No.: US 10,274,466 B2
(45) Date of Patent: Apr. 30, 2019

(54) ELUCIDATION OF ION EXCHANGE CHROMATOGRAPHY INPUT OPTIMIZATION

(71) Applicant: Genentech, Inc., South San Francisco, CA (US)

(72) Inventors: Daniel McDonald, South San Francisco, CA (US); Thomas Patapoff, South San Francisco, CA (US); Yajun Wang, Foster City, CA (US)

(73) Assignee: GENENTECH, INC., South San Francisco, CA (US)

( * ) Notice: Subject to any disclaimer, the term of this patent is extended or adjusted under 35 U.S.C. 154(b) by 365 days.

(21) Appl. No.: 14/904,422

(22) PCT Filed: Jul. 11, 2014

(86) PCT No.: PCT/US2014/046338
§ 371 (c)(1),
(2) Date: Jan. 11, 2016

(87) PCT Pub. No.: WO2015/006686
PCT Pub. Date: Jan. 15, 2015

(65) Prior Publication Data
US 2016/0161455 A1 Jun. 9, 2016

Related U.S. Application Data

(60) Provisional application No. 61/845,890, filed on Jul. 12, 2013.

(51) Int. Cl.
*G01N 33/68* (2006.01)
*G01N 30/86* (2006.01)
*G01N 30/96* (2006.01)
*B01D 15/36* (2006.01)
*B01D 15/38* (2006.01)
*C07K 1/18* (2006.01)
*C07K 1/16* (2006.01)
*G01N 30/34* (2006.01)

(52) U.S. Cl.
CPC ....... *G01N 30/8658* (2013.01); *B01D 15/362* (2013.01); *B01D 15/363* (2013.01); *B01D 15/3847* (2013.01); *C07K 1/165* (2013.01); *C07K 1/18* (2013.01); *G01N 30/34* (2013.01); *G01N 30/96* (2013.01); *G01N 33/6854* (2013.01); *G01N 33/6803* (2013.01)

(58) Field of Classification Search
CPC ............... B01D 15/362; B01D 15/363; B01D 15/3847; C07K 1/165; C07K 1/18; G01N 30/34; G01N 30/8658; G01N 30/96; G01N 33/6854; G01N 33/6803; Y10T 436/25; Y10T 436/25125; Y10T 436/255 436/25; Y10T 436/25125; Y10T 436/255
USPC ......... 436/512, 548, 86, 161, 163, 174, 175, 436/178; 422/70, 527
See application file for complete search history.

(56) References Cited

U.S. PATENT DOCUMENTS

| 4,666,855 A * | 5/1987 | Yang ...................... G01N 33/84 204/548 |
|---|---|---|
| 4,676,980 A | 6/1987 | Segal et al. |
| 4,816,567 A | 3/1989 | Cabilly et al. |
| 5,208,020 A | 5/1993 | Chari et al. |
| 5,229,275 A | 7/1993 | Goroff |
| 5,500,362 A | 3/1996 | Robinson et al. |
| 5,534,615 A | 7/1996 | Baker et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,571,894 A | 11/1996 | Wels et al. |
| 5,573,905 A | 11/1996 | Lerner et al. |
| 5,587,458 A | 12/1996 | King et al. |
| 5,589,369 A | 12/1996 | Seidman et al. |
| 5,591,669 A | 1/1997 | Krimpenfort et al. |
| 5,591,828 A | 1/1997 | Bosslet et al. |
| 5,641,870 A | 6/1997 | Rinderknecht et al. |
| 5,648,237 A | 7/1997 | Carter |
| 5,693,780 A | 12/1997 | Newman et al. |
| 5,712,374 A | 1/1998 | Kuntsmann et al. |
| 5,731,168 A | 3/1998 | Carter et al. |
| 5,789,199 A | 8/1998 | Joly et al. |
| 5,821,337 A | 10/1998 | Carter et al. |
| 5,840,523 A | 11/1998 | Simmons et al. |
| 7,521,541 B2 | 4/2009 | Eigenbrot et al. |
| 9,810,670 B2 | 11/2017 | Wang et al. |
| 2006/0067930 A1 | 3/2006 | Adams et al. |

(Continued)

FOREIGN PATENT DOCUMENTS

| EP | 0 287 513 A2 | 10/1988 |
|---|---|---|
| EP | 0 287 513 A3 | 10/1988 |

(Continued)

OTHER PUBLICATIONS

Zhang et al. Journal of Chromatography A, vol. 1272, Nov. 29, 2012, pp. 56-64.*
Guelat et al. Journal of Chromatography A, vol. 1298, Apr. 22, 2013, pp. 17-25.*
Ahamed et al "pH-gradient ion-exchange chromatography: An analytical tool for design and optimization of protein separations," *Journal of Chromatography* 1164(1-2):181-188, (Aug. 23, 2007).
Brennan et al. "Preparation of Bispecific Antibodies by Chemical Recombination of Monoclonal Immunoglobulin $G_1$ Fragments," *Science* 229:81-83, (Jul. 5, 1985).

(Continued)

*Primary Examiner* — Maureen Wallenhorst
(74) *Attorney, Agent, or Firm* — Morrison & Foerster LLP

(57) ABSTRACT

The present invention provides methods for determining chromatography separation conditions; for example, separation of a polypeptide and its charge variants. The invention also provides methods to determine a buffer condition for chromatography separation conditions. The invention also provides a robust method to analyze multiple polypeptide products.

44 Claims, 27 Drawing Sheets

(56) References Cited

U.S. PATENT DOCUMENTS

| | | | | |
|---|---|---|---|---|
| 2015/0285771 | A1* | 10/2015 | Wang | C07K 1/18 436/501 |
| 2018/0120273 | A1 | 5/2018 | Wang et al. | |

FOREIGN PATENT DOCUMENTS

| | | |
|---|---|---|
| EP | 0 287 513 B1 | 10/1988 |
| EP | 0 308 936 A2 | 3/1989 |
| EP | 0 404 097 B1 | 12/1990 |
| JP | S63-263457 A | 10/1988 |
| JP | 2002-529714 A | 9/2002 |
| JP | 2005-068161 A | 3/2005 |
| JP | 2006-087394 A | 4/2006 |
| JP | 2007-500852 A | 1/2007 |
| JP | 2007-536218 A | 12/2007 |
| JP | 2007-538260 A | 12/2007 |
| JP | 2008-503725 A | 2/2008 |
| JP | 2010-504080 A | 2/2010 |
| JP | 2012-519706 A | 8/2012 |
| JP | 2013-500244 A | 1/2013 |
| WO | WO 91/00360 A1 | 1/1991 |
| WO | WO 92/20373 A1 | 11/1992 |
| WO | WO 93/08829 A1 | 5/1993 |
| WO | WO 93/11161 A1 | 6/1993 |
| WO | WO 93/16185 A1 | 8/1993 |
| WO | WO 94/04690 A1 | 3/1994 |
| WO | WO 94/04690 C1 | 3/1994 |
| WO | WO-94/11026 A2 | 5/1994 |
| WO | WO-94/11026 A3 | 5/1994 |
| WO | WO-1999/57134 A1 | 11/1999 |
| WO | W0-00/29004 A1 | 5/2000 |
| WO | WO-00/27496 A1 | 5/2000 |
| WO | WO-00/59863 A1 | 10/2000 |
| WO | WO 02/051870 A2 | 7/2002 |
| WO | WO 02/051870 A3 | 7/2002 |
| WO | WO 03/035694 A2 | 5/2003 |
| WO | WO-2004/024866 A2 | 3/2004 |
| WO | WO-2004/103519 A2 | 12/2004 |
| WO | WO-2004/103519 A3 | 12/2004 |
| WO | WO 2005/035572 A2 | 4/2005 |
| WO | WO 2005/035572 A3 | 4/2005 |
| WO | WO-2005/104763 A2 | 11/2005 |
| WO | WO-2005/104763 A3 | 11/2005 |
| WO | WO-2005/114930 A2 | 12/2005 |
| WO | WO-2005/114930 A3 | 12/2005 |
| WO | WO-2006/007429 A1 | 1/2006 |
| WO | WO-2008/007073 A2 | 1/2008 |
| WO | WO-2008/007073 A3 | 1/2008 |
| WO | WO-2010/102241 A1 | 9/2010 |
| WO | WO-2011/009623 A1 | 1/2011 |
| WO | WO-2012/102104 A1 | 8/2012 |
| WO | WO-2012/129680 A1 | 10/2012 |
| WO | WO-2014/078729 A1 | 5/2014 |

OTHER PUBLICATIONS

Brodeur et al. "Mouse-Human Myeloma Partners for the Production of Heterohybridomas," Chapter 4 in *Monoclonal Antibody Production Techniques and Applications*, Marcel Dekker, Inc.: New York, New York, pp. 51-63, (1987).

Brüggemann et al. "Designer Mice: The Production of Human Antibody Repertoires in Transgenic Animals," *Year in Immuno.* 7:33-40, (1993).

Capel et al. "Heterogeneity of Human IgG Fc Receptor," *Immunomethods* 4:25-34, (1994).

Caron et al. "Engineered Humanized Dimeric Forms IgG Are More Effective Antibodies," *J. Exp Med.* 176:1191-1195 (1992).

Carter et al. "High Level *Escherichia coli* Expression and Production of a Bivalent Humanized Antibody Fragment," *Bio/Technology* 10:163-167, (Feb. 1992).

Carter et al. "Humanization of an Anti-p185$^{HER2}$ Antibody for Human Cancer Therapy," *Proc. Natl. Acad. Sci. USA* 89:4285-4289, (May 1992).

Charlton. "Expression and Isolation of Recombinant Antibody Fragments in *E. coli*," Chapter 14 in *Methods in Molecular Biology* Lo, B.K.C. ed., Humana Press: Totowa, NJ, pp. 245-254, (2003).

Chothia et al. "Canonical Structures for the Hypervariable Regions of Immunoglobulins," *J. Mol. Biol.* 196:901-917, (1987).

Clackson et al. "Making Antibody Fragments Using Phage Display Libraries," *Nature* 352:624-628, (Aug. 15, 1991).

Clynes et al. "Fc Receptor are Required in Passive and Active Immunity to Melanoma," *Proc. Natl.Acad. Sci. (USA)* 95:652-656 (Jan. 1998).

Cunningham et al. "High Resolution Epitope Mapping of hGH-Receptor Interactions by Alanine-Scanning Mutagenesis," *Science* 244:1081-1085 (Jun. 3, 1989).

Daeron. "Fc Receptor Biology," *Annu. Rev. Immunol.* 15:203-234, (1997).

Davies et al. "'Camelising' Human Antibody Fragments: NMR Studies on VH Domains," *Febs Lett.* 339(3):285-290, (Feb. 21, 1994).

De Haas et al. "Fcγ Receptor of Phagocytes," *J. Lab. Clin. Med.* 126:330-41 (1995).

Dooley et al. "Antibody Repertoire Development in Cartilaginous Fish," *Dev Comp Immunol.* 30(1-2):43-56, (2006).

Fang et al. "Temperature-induced changes in the bandwidth behaviour of proteins separated with cation-exchange adsorbents," *Journal of Chromatography* 729(I):67-79, (Apr. 5, 1996).

Farnan et al "Multiproduct High-Resolution Monoclonal Antibody Charge Variant Separations by pH Gradient Ion-Exchange Chromatography," *Analytical Chemistry* 81(21):8846-8857, (Nov. 1, 2009).

Gazzano-Santoro et al."A Non-Radioactive Complement-Dependent Cytotoxicity Assay for Anti-CD20 Monoclonal Antibody," *J. Immunol. Methods* 202:163 (1996).

GE Healthcare. "Ion Exchange Chromatography & Chromatofocusing Principles and Methods Ion Exchange Chromatography & Chromatofocusing—Principles and Methods imagination at Work," located at <http://www.gelifesciences.com/gehclsimages/GELS/Related%20Content/Files/1314823637792/litdoc11000421 20140416231512>, last visited on Aug. 28, 2014, pp. 7-183 (total pages 186), (2010).

Goding. "Production of Monoclonal Antibodies," Chapter 3 in *Monoclonal Antibodies: Principles and Practice*, Academic Press., pp. 56-103, Table of Contents pp. vii-ix, (1983).

Griffiths et al. "Human Anti-Self Antibodies with High Specificity From Phage Display Libraries," *EMBO J.* 12(2):725-734, (1993).

Gruber et al. "Efficient Tumor Cell Lysis Mediated by a Bispecific Single Chain Antibody Expressed in *Escherichia coli,*" *J. Immunol.* 152:5368-5374, (1994).

Guyer et al. "Immunoglobulin Binding by Mouse Intestinal Epithelial Cell Receptors, " *J. Immunol.* 117(2):587 (Aug. 1976).

Holliger et al. "'Diabodies': Small Bivalent and Bispecific Antibody Fragments," *Proc. Natl. Acad. Sci. USA* 90:6444-6448, (Jul. 1993).

Holt et al. "Domain Antibodies: Proteins for Therapy," *Trends Biotechnology* 21(11):484-490, (Nov. 2003).

Jakobovits et al. "Analysis of Homozygous Mutant Chimeric Mice: Deletion of the Immunoglobulin Heavy-Chain Joining Region Blocks B-Cell Development and Antibody Production," *Proc. Natl. Acad. Sci. USA* 90:2551-2555, (Mar. 1993).

Jakobovits et al. "Germ-line Transmission and Expression of a Human-Derived Yeast Artificial Chromosome," *Nature* 362:255-258, (Mar. 18, 1993).

Johnson,et al. "Human Antibody Engineering," *Current Opinion in Structural Biology* 3:564-571 (1993).

Jones et al. "Replacing the Complementarity-determining Regions in a Human Antibody With Those From a Mouse," *Nature* 321:522-525, (May 29, 1986).

Kelley et al. "High-Throughput Screening of Chromatographic Separations: IV. Ion-Exchange," *Biotechnology and Bioengineering* 100(5):950-963, (Aug. 1, 2008).

Kim et al. "Localization of the Site of the Murine IgG1 Molecule That is Involved in Binding to the Murine Intestinal Fc Receptor," *Eur. J. Immunol.* 24:2429-2434, (1994).

(56) References Cited

OTHER PUBLICATIONS

Kohler et al. "Continuous Cultures of Fused Cells Secreting Antibody of Predefined Specificity," *Nature* 256:495-497, (Aug. 7, 1975).
Kostelny et al. "Formation of a Bispecific Antibody by the Use of Leucine Zippers," *J. Immunol.* 148(5):1547-1553, (Mar. 1, 1992.
Kozbor. "A Human Hybrid Myeloma for Production of Human Monoclonal Antibodies," *J. Immunol.* 133(6):3001-3005, (Dec. 1984).
Lehninger. The Amino Acid Building Blocks of Proteins, Chapter 4 in *Biochemistry*, second ed., Worth Publishers, New York, New York, pp. 73-75, (1975).
Marks et al. (1991). "By-Passing Immunization: Human Antibodies from V-gene Libraries Displayed on Phage," *J. Mol. Biol.* 222:581-597, (1991).
Marks et al. "By-Passing Immunization: Building High Affinity Human Antibodies by Chain Shuffling," *Bio/Technology* 10:779-783, (Jul. 1992).
Mccafferty et al. "Phage Antibodies: Filmentous Phage Antibody Variable Domains," *Nature* 348:552-554 (Dec. 6, 1990).
Milstein et al. (Oct. 6, 1983). "Hybrid Hybridomas and Their Use in Immunohistochemistry," *Nature* 305:537-540, (Oct. 6, 1983).
Morimoto et al. "Single-Step Purification of F(ab')₂ Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24:107-117, (1992).
Morrison et al. "Chimeric Human Antibody Molecules: Mouse Antigen-Binding Domains with Human Constant Region Domains," *Proc. Natl. Acad. Sci.* 81:6851-6855, (Nov. 1984).
Munson et al. "Ligand: A Versatile Computerized Approach for Characterization of Ligand-Binding Systems," *Analy. Biochem.* 107:220-239, (1980).
Muyldermans et al. "Recognition of Antigens by Single-Domain Antibody Fragments: the Superfluous Luxury of Paired Domains," *Trends Biochem Sci.* 26(4):230-235, (Apr. 2001).
Plückthun. (1992). "Mono- and Bivalent Antibody Fragments Produced in *Escherichia coli*: Engineering, Folding and Antigen Binding," *Immunol Revs.* 130:151-188.
Pluckthun. "Antibodies of *Escherichia coli*," Chapter 11 in *The Pharmacology of Monoclonal Antibodies*, vol. 113, Rosenburg and Moore eds., Springer-Verlag, New York, New York, pp. 269-315 (1994).
Presta. "Antibody Engineering," *Curr. Op. Struct. Biol.* 2:593-596, (1992).
Presta et al. "Humanization of an Antibody Directed Against IgE," *J. Immunol.* 151(5):2623-2632, (Sep. 1, 1993).
Ravetch et al. "Fc Receptors," *Annu. Rev. Immunol* 9:457-492 (1991).
Riechmann et al. "Reshaping Human Antibodies for Therapy," *Nature* 332:323-327, (Mar. 24, 1988).
Shopes. "A Genetically Engineered Human IgG Mutant With Enhanced Cytolytic Activity," *J. Immunol.* 148:2918-2922, (May 1, 1992).
Sims et al. "A Humanized CD18 Antibody Can Block Function Without Cell Destruction," *J. Immunol.* 151(4):2296-2308, (Aug. 15, 1993).
Skerra. "Bacterial Expression of Immunoglobulin Fragments," *Curr. Opinion in Immunol.* 5:256-262, (1993).
Stevenson et al. "A Chimeric Antibody With Dual Fc Regions (bisFabFc) Prepared by Manipulations at the IgG Hinge," *Anti-Cancer Drug Design* 3:219-230, (1989).
Suresh et al. "Bispecific Monoclonal Antibodies From Hybrid Hybridomas," *Methods in Enzymology* 121:210-228, (1986).
Teshima et al. "Separation of Oxidized Variants of a Monoclonal Antibody by Anion-Exchange," *J. Chromatogr. A* 1218(15):2091-2097, (Apr. 15, 2011).
Traunecker et al. "Bispecific Single Chain Molecules (Janusins) Target Cytotoxic Lymphocytes on HIV Infected Cells," *EMBO J.* 10(12):3655-3659, (1991).
Tsonev et al. "Theory and Applications of a Novel Ion Exchange Chromatographic Technology Using Controlled pH Gradients for Separating Proteins on Anionic and Cationic Stationary Phases," *Journal of Chromatography* 1200(2):166-182, (Jul. 25, 2008).
Tutt et al. "Trispecific F(ab')₃ Derivatives That Use Cooperative Signaling Via the TCR/CD3 Complex and CD2 to Activate and Redirect Resting Cytotoxic T Cells" *J. Immunol.* 147:60-69, (Jul. 1, 1991).
Verhoeyen et al. "Reshaping Human Antibodies: Grafting an Antilysozyme Activity," *Science* 239:1534-1536, (Mar. 25, 1988).
Vitetta et al. "Redesigning Nature's Posions to Create Anti-Tumour Reagants," *Science* 238: 1098 (1987).
Vlasak et al. "Heterogeneity of Monoclonal Antibodies Revealed by Charge Sensitive Methods," *Curr. Phann. Biotechnol.* 9:468-481, (2008).
Wang et al. Impact of Methionine Oxidation in Human IgG1 Fc on Serum Half-Life of Monoclonal Antibodies, *Mol. Immunol.* 48:860-866, (Mar. 2011).
Ward et al. "Binding activities of a repertoire of single immunoglobulin variable domains secreted from *Escherichia coli*," Nature 341:544-546, (Oct. 12, 1989).
Waterhouse et al. "Combinatorial Infection and in vivo Recombination: A Strategy for Making Large Phage Antibody Repertoires," *Nucl. Acids Res.* 21(9):2265-2266, (1993).
Wolff et al. "Monoclonal Antibody Homodimers: Enhanced Antitumor Activity in Nude Mice," *Cancer Research* 53:2560-2565 (1993).
Zapata et al. "Engineering Linear F(ab')2 Fragments for Efficient Production in *Escherichia coli* and Enhanced Antiproliferative Activity," *Protein Eng.* 8(10):1057-1062, (1995).
International Search Report dated Sep. 9, 2014, for PCT Application No. PCT/US2014/046338, filed on Jul. 11, 2014, four pages.
Written Opinion dated Sep. 9, 2014, for PCT Application No. PCT/US2014/046338, filed on Jul. 11, 2014, eight pages.
Barlow et al. "The Distribution of charged groups in Proteins," *Biopolymers* 25: 1717-1733, (Sep. 1986).
Dick et al. "Identification and Measurement of Isoaspartic Acid Formation in the Complementarity Determinin Region of a Fully Human Monoclonal Antibody," *J. Chromatogr. B* 877(30):3841-3849, (2009, e-pub. Sep. 25, 2009).
He et al. "Analysis of Charge Heterogeneities in mAbs Using Imaged CE," *Electrophoresis* 30(5):714-722, (Mar. 2009).
Kim et al. "Characterization of a Unique IgG1 mAb CEX Profile by Limited Lys-C Proteolysis/CEX Separation Coupled With Mass Spectrometry and Structural analysis," *J. Chromatogr. B* 878(22):1973-1981, (Jul. 2010).
Miller et al. "Characterization of Site-Specific Glycation During Process Development of a Human Therapeutic Monoclonal Antibody," *J. Pharm Sci* 100(7):2543-2550, (Jul. 2011).
Liu et al. "Glutamine Deamidation of a Recombinant Monoclonal Antibody," *Rapid Commun Mass Spectrom* 22(24):4081-4088, (Dec. 2008).
Sosic et al. "Application of Imaging Capillary IEF for Characterization and Quantitative Analysis of Recombinant Protein Charge Heterogeneity," *Electrophoreis* 29:4368-4376, (Nov. 29, 2008).
Amersham Biosciences. (2004). "Ion Exchange Chromatography & Chromatofocusing. Principles and Methods," Edition AA, Amersham Biosciences, 188 pages.

\* cited by examiner

ELUCIDATION OF ION EXCHANGE CHROMATOGRAPHY INPUT OPTIMIZATION

CROSS-REFERENCE TO RELATED APPLICATIONS

This application is a National Phase application under 35 U.S.C. § 371 of International Application No. PCT/US2014/046338, filed Jul. 11, 2014, which claims priority to U.S. Provisional Patent Application No. 61/845,890, filed Jul. 12, 2013; the disclosure of each of which is hereby incorporated herein by reference in its entirety.

FIELD OF THE INVENTION

The present invention provides methods for analyzing preparations of polypeptides using ionic strength gradient ion exchange chromatography for protein charge variants.

BACKGROUND OF THE INVENTION

Proteins like monoclonal antibodies (mAbs) have mostly charged and polar amino acids at the surface in an aqueous environment (Barlow, D J and Thornton, J M (1986) *Biopolymers* 25:1717). Because of molecular interaction with the solution components, the surface residues can undergo multiple chemical and enzymatic modifications, leading to a heterogeneous mixture of protein variants with slight differences on their electrostatic surface (Dick, L W et al., (2009) *J. Chromatogr. B* 877:3841; Liu, H W et al., (2008) *Rapid Commun. Mass Spectrom.* 22:4081; Miller, A K, et al., (2011) *J. Pharm. Sci.* 100:2543; Wang, W R et al., (2011) *Mol. Immunol.* 48:860). Cation-exchange chromatography (CEC) is considered to be the gold standard to profile the charge heterogeneity of protein therapeutics according to a recent review by Vlasak, J and Ionescu, R (2008 *Curr. Pharm. Biotechnol.* 9:468). The charge sensitive separation method is typically required by the regulatory agencies to ensure the production consistency during manufacturing and to monitor the degradation level of protein therapeutics (Miller, A K, et al., (2011) *J. Pharm. Sci.* 100:2543; He, X P Z (2009) *Electrophoresis* 30:714; Sosic, Z et al., (2008) *Electrophoresis* 29:4368; Kim, J et al., (2010) *J. Chromatogr. B* 878:1973: Teshima, G et al., (2010) *J. Chromatogr. A* 1218:2091).

Ion exchange chromatography (IEC) is typically performed in a bind and elute mode. Generally a protein sample, such as an mAb, is introduced to the stationary phase under conditions that facilitate the protein binding to the column (i.e., in 100% buffer A). A salt or pH gradient (i.e. increasing % of buffer B) is applied to induce the different charged proteins to elute in order. IEC methods are typically product specific. The development of a method that is both robust, i.e. can withstand fluctuations in temperature and pH, and can sufficiently resolve the charge heterogeneity is resource intensive. Methods to develop an optimal buffer system that allows development of robust assays to determine the presence of contaminants in multiple polypeptide products are desirable. The present invention provides methods to predict optimal conditions for ion exchange based on mathematical modeling of both the polypeptide and the buffering system.

All references cited herein, including patent applications and publications, are incorporated by reference in their entirety.

BRIEF SUMMARY

In some aspects, the invention provides methods for identifying an optimal ion exchange chromatography separation condition to analyze a plurality of compositions, wherein each composition comprises a polypeptide with and one or more contaminants, the method comprising a) plotting a net charge versus pH curve at a selected temperature based on the amino acid composition of the polypeptides of two or more of the compositions, and b) determining the inflection point of the net charge versus pH curve at or near neutral pH by determining the second derivative of the plots of step a); wherein the optimal ion exchange chromatography separation condition is a pH at about a common inflection point for the polypeptides of one or more of the compositions. In some embodiments, the methods further comprise c) determining the change in the inflection point pH of the net charge versus pH curve with a change in the temperature (dIP/dT) for the polypeptides of two or more of the compositions, d) selecting a buffer for use in the chromatography, wherein a change in the acid dissociation constant of the buffer with change in temperature (dpKa/dT) is essentially the same as the dIP/dT of the polypeptides.

In other aspects, the invention provides method for identifying an optimal ion exchange chromatography separation condition to analyze a composition comprising a polypeptide with and one or more contaminants, the method comprising a) plotting a net charge versus pH curve at a selected temperature based on the amino acid composition of the polypeptide, and b) determining the inflection point of the net charge versus pH curve at or near neutral pH by determining the second derivative of the plots of step a); wherein the optimal ion exchange chromatography separation condition is a pH at about the inflection point for the polypeptide.

In some embodiments, if the net charge at the inflection point is positive, a cation exchange material is used for the ion exchange chromatography. In some embodiment, the cation exchange chromatography material is a sulfonated chromatography material or a carboxylated chromatography material. In other embodiments, if the net charge at the inflection point is negative, an anion exchange material is used for the chromatography. In some embodiments, the anion exchange chromatography material is a quarternary amine chromatography material or a tertiary amine chromatography material. In yet other embodiments, a mixed mode chormatography material is used for the chromatography. In some embodiments, the mixed mode ion exchange material is a mixture of sequentially packed sulfonated chromatography material or carboxylated chromatography material and a quarternary amine chromatography material or tertiary amine chromatography material.

In some embodiments, the buffer provides an effective buffer capacity at the inflection point pH. In some embodiments, the dIP/dT of the polypeptides of one or more of the compositions is about −0.02 pH units. In some embodiments, the change in temperature is from about 20° C. to about 70° C. In further embodiments, the change in temperature is from about 20° C. to about 50° C. In some embodiments, dpKa/dT=dIP/dT±50%. In some embodiments, the net charge of the polypeptide in the buffer selected in step d) changes by less than 0.5 over 30° C. In some embodiments, the buffer selected in step d) is used in the chromatography at a concentration ranging from about 5 mM to about 250 mM.

In some embodiments of the above embodiments, the buffer compositions further comprise a salt. In further embodiments, the salt is NaCl, KCl, $(NH_4)_2SO_4$, or $Na_2SO_4$. In some embodiments, the concentration of the salt ranges from about 1 mM to about 1M.

In some embodiments of the methods of the invention, the polypeptide is an antibody or immunoadhesin or fragment thereof. In some embodiments, the polypeptide is a monoclonal antibody or fragment thereof. In some embodiments, the antibody is a human antibody. In other embodiments, the antibody is a humanized antibody. In yet other embodiments, the antibody is a chimeric antibody. In some embodiments, the antibody is an antibody fragment.

In some embodiments of the methods of the invention, the contaminant is a variant of the polypeptide. In some embodiments, the contaminant is a degradation product of the polypeptide. In some embodiments, the contaminant is a charge variant of the polypeptide.

In some aspects, the invention provide methods for analyzing a composition, wherein the composition comprises a polypeptide and one or more contaminants, wherein the method effectively separates polypeptides from the contaminants, the method comprising a) determining the optimal pH and temperature ion exchange separation conditions for a plurality of compositions, each composition comprising a target polypeptide and one or more contaminants according to the methods of the invention, b) binding the polypeptide and one of more contaminants from the composition to an ion-exchange chromatography material using a loading buffer, wherein the loading buffer comprises a buffer identified by the method of the invention; c) eluting the polypeptide and one or more contaminants from the ion-exchange chromatography material using a gradient of an elution buffer, wherein the elution buffer comprises the buffer and a salt, wherein the concentration of the salt increases in a gradient over time, wherein the polypeptide and the one or more contaminants are separated by the gradient; and d) detecting the polypeptide and the one or more contaminants.

In some aspects, the invention provides methods for analyzing a composition comprising a polypeptide and one or more contaminants, wherein the method effectively separates the polypeptide from the contaminants, the method comprising a) binding the polypeptide and one of more contaminants to an ion-exchange chromatography material using a loading buffer, wherein the loading buffer comprises a buffer, and wherein the pH and temperature of the chromatography has been optimized for a plurality of target polypeptides by i) plotting a net charge versus pH curve at a selected temperature, wherein the curve is based on the amino acid composition of the polypeptide of two or more target polypeptides, and ii) determining the inflection point of the net charge versus pH curve by determining the second derivative of the plots of step i); wherein the optimal ion exchange chromatography condition is a pH at a common inflection point for two or more target polypeptides; b) eluting the polypeptide and one or more contaminants from the ion-exchange chromatography material using a gradient of an elution buffer, wherein the elution buffer comprises the buffer and a salt, wherein the polypeptide and the one or more contaminants are separated by the gradient; and c) detecting the polypeptide and the one or more contaminants In some embodiments, the selected temperature is ambient temperature. In some embodiments, the buffer is identified by a) determining the change in the inflection point pH of the net charge versus pH curve with a change in the temperature (dIP/dT) for the two or more target polypeptides, b) selecting a buffer for which a change in the acid dissociation constant buffer with change in temperature (dpKa/dT) is essentially the same as the dIP/dT of the one or more target polypeptides with common inflection points. In some embodiments, the buffer provides an effective buffer capacity at the inflection point pH.

In some aspects the invention provides methods for analyzing a composition comprising a polypeptide and one or more contaminants, wherein the method effectively separates the polypeptide from the contaminants, the method comprising a) binding the polypeptide and one of more contaminants to an ion-exchange chromatography material using a loading buffer, wherein the loading buffer comprises a buffer, and wherein the pH and temperature of the chromatography has been optimized for a plurality of target polypeptides; b) eluting the polypeptide and one or more contaminants from the ion-exchange chromatography material using a gradient of an elution buffer, wherein the elution buffer comprises the buffer and a salt, wherein the polypeptide and the one or more contaminants are separated by the gradient; and c) detecting the polypeptide and the one or more contaminants. In some embodiments, the buffer is N-(2-Acetamido)-2-aminoethanesulfonic acid (ACES) or 4-(2-hydroxyethyl)-1-piperazineethanesulfonic acid (HEPES). In further embodiments, the concentration of the buffer ranges from about 5 mM to about 20 mM. In some embodiments, the change in temperature is from about 20° C. to about 70° C. In further embodiments, the change in temperature is from about 20° C. to about 50° C. In some embodiments, dpKa/dT=dIP/dT±50%. In some embodiments, the net charge of the polypeptide in the buffer changes by less than 0.5 over 30° C. In some embodiments, the buffer is used in the chromatography at a concentration ranging from about 5 mM to about 250 mM.

In some embodiments of the above embodiments, the buffer compositions further comprise a salt. In further embodiments, the salt is NaCl, KCl, $(NH_4)_2SO_4$, or $Na_2SO_4$. In some embodiments, the concentration of the salt ranges from about 1 mM to about 1M. In some embodiments, the salt concentration increases from about 0 mM to about 100 mM in about 100 minutes. In other embodiments, the salt concentration increases from about 0 mM to about 80 mM in about 40 minutes.

In some embodiments of the methods of the invention, the polypeptide is an antibody or immunoadhesin or fragment thereof. In some embodiments, the polypeptide is a monoclonal antibody or fragment thereof. In some embodiments, the antibody is a human antibody. In other embodiments, the antibody is a humanized antibody. In yet other embodiments, the antibody is a chimeric antibody. In some embodiments, the antibody is an antibody fragment.

In some embodiments of the methods of the invention, the contaminant is a variant of the polypeptide. In some embodiments, the contaminant is a degradation product of the polypeptide. In some embodiments, the contaminant is a charge variant of the polypeptide.

In some emodiments, the chromatography material is a cation exchange chromatography material. In further embodiments, the cation exchange chromatography material is a sulfonated chromatography material or a carboxylated chromatography material.

In some aspects, the invention provides methods for analyzing a plurality of polypeptide compositions, wherein each polypeptide composition comprises an polypeptide and one or more charge variants of the polypeptide, wherein the method effectively separates the polypeptide from its charge variants; for each polypeptide composition the method comprises, a) binding the polypeptide and one of more charge variants to an ion-exchange chromatography material using a loading buffer at a flow rate of about 1 mL/minute, wherein the loading buffer comprises 10 mM HEPES buffer at about pH 7.6 at about 40° C.; b) eluting the polypeptide and the charge variants contaminants from the ion-exchange chromatography material using a gradient of an elution buffer, wherein the elution buffer comprises about 10 mM HEPES buffer at about pH 7.6 and a NaCl, wherein the concentration of the NaCl increases in the gradient from about 0 mM to about 80 mM in about 40 minutes, wherein the polypeptide and its charge variants are separated by the gradient; and c) detecting the polypeptide and the one or more charge variants. In some embodiments, the plurality of polypeptide compositions comprises different polypeptides. In some embodiments, the plurality of polypeptide compositions comprises polypeptides with different pIs. In some embodiments, the polypeptide compositions are antibody compositions.

DETAILED DESCRIPTION OF THE INVENTION

Figure 1:
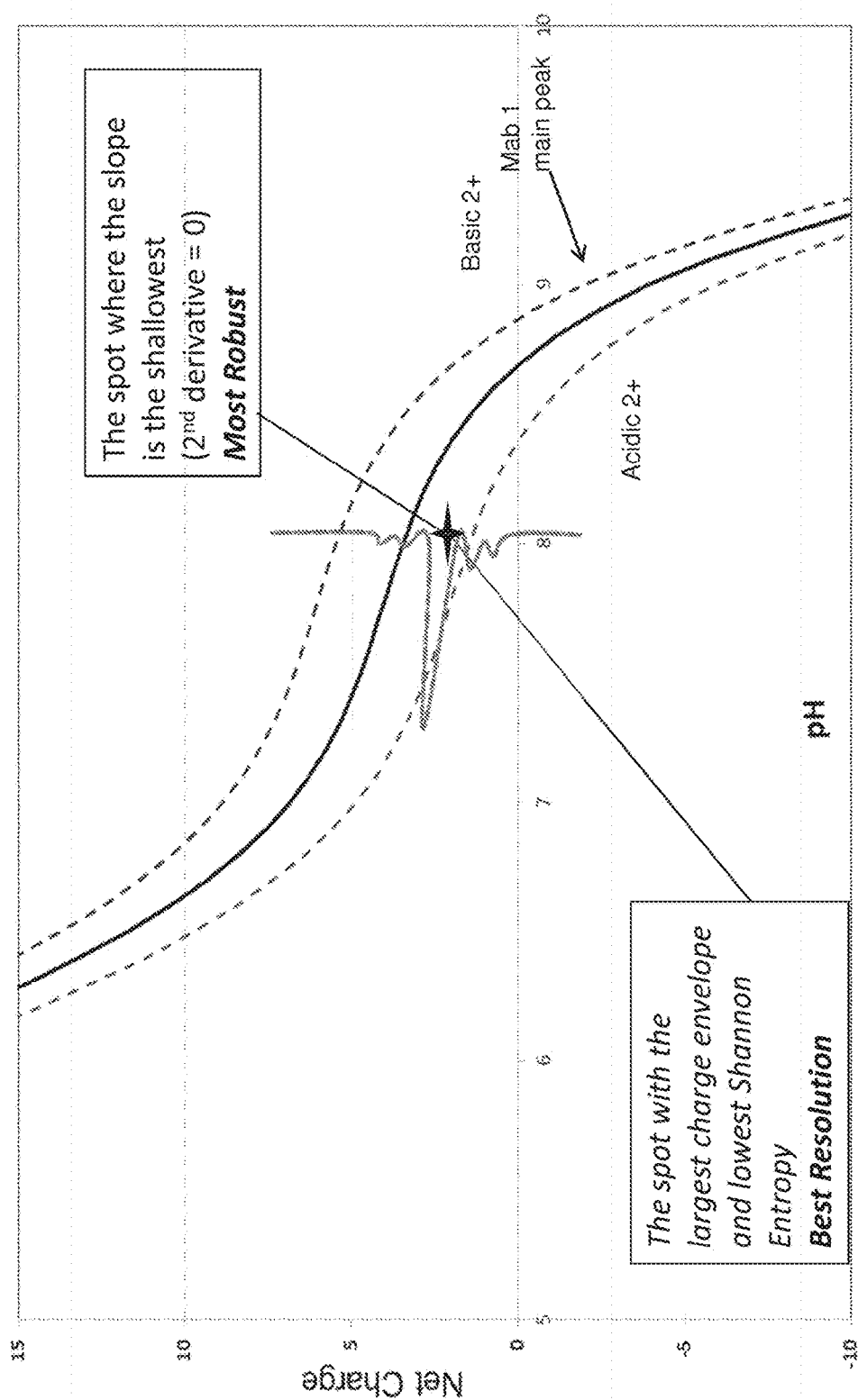
FIG. 1 is a graph plotting the calculated net charge versus pH for monoclonal antibody mAb1 (solid blank line) and its two charge variants. The dashed lines represents an acidic variant with two negative charges and a basic variant with two positive charges as indicated. The curves were created using the amino acid sequence composition of mAb1 and its variants. The star denotes the inflection point of the curve. A platform IEC method run at the inflection point pH will provide optimal resolution and robustness with respect to pH.

The invention provides methods for identifying an optimal ion exchange chromatography separation condition to analyze a composition comprising a polypeptide with and one or more contaminants, the method comprising a) plotting a net charge versus pH curve at a selected temperature based on the amino acid composition of the polypeptide, and b) determining the inflection point (IP) of the net charge versus pH curve at or near neutral pH by determining the second derivative of the plots of step a); wherein the optimal ion exchange chromatography separation condition is a pH at about the inflection point for the polypeptide. In some embodiments, the distribution of charge frequency is determined by calculating the Shannon entropy of the polypeptide at different pH values for a given temperature. As Shannon entropy decreases, the charge distribution of the polypeptide in a composition becomes more homogenous. As a result, the ability to resolve between the polypeptide and its charge variants improves.

In some embodiments, the invention provides methods to identify a buffer for use in an optimal ion exchange chromatography separation condition to analyze a composition comprising a polypeptide with and one or more contaminants. In some embodiments, a buffer is selected where the change in acid dissociation constant with temperature (dpKa/dT) is approximately equal to the change in inflection point as described above with temperature (dIP/dT).

In some aspects, the invention provides methods for identifying an optimal ion exchange chromatography separation condition to analyze a plurality of compositions, wherein each composition comprises a polypeptide with and one or more contaminants, the method comprising a) plotting a net charge versus pH curve at a selected temperature based on the amino acid composition of the polypeptides of two or more of the compositions, and b) determining the inflection point of the net charge versus pH curve at or near neutral pH by determining the second derivative of the plots of step a); wherein the optimal ion exchange chromatography separation condition is a pH at about a common inflection point for the polypeptides of one or more of the compositions. As such, the method can be used to analyze multiple products without the need for developing specific protocols for each product.

I. Definitions

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component or toxin. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

The term "polypeptide charge variant" as used herein refers to polypeptide that has been modified from its native state such that the charge of the polypeptide is altered. In some examples, charge variants are more acidic than the parent polypeptide; i.e. have a lower pI than the parent polypeptide. In other examples, charge variants are more basic than the parent polypeptide; i.e. have a higher pI than the parent polypeptide. Such modifications may be engineered or the result of natural processes such as oxidation, deamidation, C-terminal processing of lysine residues, N-terminal pyroglutamate formation, and glycation. In some examples, a polypeptide charge variant is a glycoprotein where the glycan attached to the protein is modified such that the charge of the glycoprotein is altered compared to parent glycoprotein, for example, by addition of sialic acid or its derivatives. An "antibody charge variant" as used herein is an antibody or fragment thereof wherein the antibody or fragment thereof has been modified from its native state such that the charge of the antibody or fragment thereof is altered.

"Purified" polypeptide (e.g., antibody or immunoadhesin) means that the polypeptide has been increased in purity, such that it exists in a form that is more pure than it exists in its natural environment and/or when initially synthesized and/or amplified under laboratory conditions. Purity is a relative term and does not necessarily mean absolute purity.

The term "antagonist" is used in the broadest sense, and includes any molecule that partially or fully blocks, inhibits, or neutralizes a biological activity of a native polypeptide. In a similar manner, the term "agonist" is used in the broadest sense and includes any molecule that mimics a biological activity of a native polypeptide. Suitable agonist or antagonist molecules specifically include agonist or antagonist antibodies or antibody fragments, fragments or amino acid sequence variants of native polypeptides, etc. Methods for identifying agonists or antagonists of a polypeptide may comprise contacting a polypeptide with a candidate agonist or antagonist molecule and measuring a detectable change in one or more biological activities normally associated with the polypeptide.

A polypeptide "which binds" an antigen of interest, e.g. a tumor-associated polypeptide antigen target, is one that binds the antigen with sufficient affinity such that the polypeptide is useful as a diagnostic and/or therapeutic agent in targeting a cell or tissue expressing the antigen, and does not significantly cross-react with other polypeptides. In such embodiments, the extent of binding of the polypeptide to a "non-target" polypeptide will be less than about 10% of the binding of the polypeptide to its particular target polypeptide as determined by fluorescence activated cell sorting (FACS) analysis or radioimmunoprecipitation (RIA).

With regard to the binding of a polypeptide to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. The term "immunoglobulin" (Ig) is used interchangeable with antibody herein.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody to specifically bind to a particular antigen.

The antigen binding specificity of an antibody is determined by the structural characteristics of the V region. The variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" (HVRs) that are each 9-12 amino acids long. The variable domains of native heavy and light chains each comprise four FRs, largely adopting β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Each V region typically comprises three HVRs, e.g. complementarity determining regions ("CDRs", each of which contains a "hypervariable loop"), and four framework regions. An antibody binding site, the minimal structural unit required to bind with substantial affinity to a particular desired antigen, will therefore typically include the three CDRs, and at least three, preferably four, framework regions interspersed there between to hold and present the CDRs in the appropriate conformation. Classical four chain antibodies have antigen binding sites which are defined by $V_H$ and $V_L$ domains in cooperation. Certain antibodies, such as camel and shark antibodies, lack light chains and rely on binding sites formed by heavy chains only. Single domain engineered immunoglobulins can be prepared in which the binding sites are formed by heavy chains or light chains alone, in absence of cooperation between $V_H$ and $V_L$.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" (HVR) when used herein refers to the amino acid residues of an antibody that are responsible for antigen binding. The hypervariable region may comprise amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

"Framework" or "FR" residues are those variable domain residues other than the hypervariable region residues as herein defined.

"Antibody fragments" comprise a portion of an intact antibody, preferably comprising the antigen binding region thereof. Examples of antibody fragments include Fab, Fab', $F(ab')_2$, and Fv fragments; diabodies; tandem diabodies (taDb), linear antibodies (e.g., U.S. Pat. No. 5,641,870, Example 2; Zapata et al., *Protein Eng.* 8(10):1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s). "Mono specific" refers to the ability to bind only one epitope. According to one embodiment the multispecific antibody is an IgG antibody that binds to each epitope with an affinity of 5 μM to 0.001 pM, 3 μM to 0.001 pM, 1 μM to 0.001 pM, 0.5 μM to 0.001 pM, or 0.1 μM to 0.001 pM.

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003): 21:484-490; WO 2005/035572; WO 03/035694; Febs Lett (1994) 339:285-290; WO00/29004; WO 02/051870).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the methods provided herein may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA* 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

For the purposes herein, an "intact antibody" is one comprising heavy and light variable domains as well as an Fc region. The constant domains may be native sequence constant domains (e.g. human native sequence constant domains) or amino acid sequence variant thereof. Preferably, the intact antibody has one or more effector functions.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

A "naked antibody" is an antibody (as herein defined) that is not conjugated to a heterologous molecule, such as a cytotoxic moiety or radiolabel.

In some embodiments, antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl. Acad. Sci. (USA)* 95:652-656 (1998).

"Human effector cells" are leukocytes that express one or more FcRs and perform effector functions. In some embodiments, the cells express at least FcγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

"Complement dependent cytotoxicity" or "CDC" refers to the ability of a molecule to lyse a target in the presence of complement. The complement activation pathway is initiated by the binding of the first component of the complement system (Clq) to a molecule (e.g. polypeptide (e.g., an antibody)) complexed with a cognate antigen. To assess complement activation, a CDC assay, e.g. as described in Gazzano-Santoro et al., *J. Immunol. Methods* 202:163 (1996), may be performed.

The terms "Fc receptor" or "FcR" are used to describe a receptor that binds to the Fc region of an antibody. In some embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Contaminants" refer to materials that are different from the desired polypeptide product. In some embodiments of the invention, contaminants include charge variants of the polypeptide. In some embodiments of the invention, contaminants include charge variants of an antibody or antibody fragment. In other embodiments of the invention, the contaminant includes, without limitation: host cell materials, such as CHOP; leached Protein A; nucleic acid; a variant, fragment, aggregate or derivative of the desired polypeptide; another polypeptide; endotoxin; viral contaminant; cell culture media component, etc. In some examples, the contaminant may be a host cell protein (HCP) from, for example but not limited to, a bacterial cell such as an *E. coli* cell, an insect cell, a prokaryotic cell, a eukaryotic cell, a yeast cell, a mammalian cell, an avian cell, a fungal cell.

As used herein, the term "immunoadhesin" designates antibody-like molecules which combine the binding specificity of a heterologous polypeptide with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand.

The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

As used herein "essentially the same" indicates that a value or parameter has not been altered by a significant effect. For example, an ionic strength of a chromatography mobile phase at column exit is essentially the same as the initial ionic strength of the mobile phase if the ionic strength has not changed significantly. For example, an ionic strength at column exit that is within 10%, 5% or 1% of the initial ionic strength is essentially the same as the initial ionic strength.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

II. Methods of Chromatography

A. Determining Optimal Ion Exchange Chromatography Separation Conditions

The invention provides methods to predict optimal ion exchange conditions to perform IEC on a polypeptide such that resolution loss is minimized with changes in pH and temperature. In some embodiments, the ion exchange chromatography is used to detect contaminants in a composition comprising a polypeptide. In some embodiments, the polypeptide is an antibody or antigen-binding fragment thereof. In some embodiments, the contaminant is a charge variant; for example, a basic charge variant and/or an acid charge variant of the polypeptide including basic charge variants and/or acidic charge variants of antibodies or antibody fragments.

In some embodiments of the invention, conditions are identified where the polypeptide is at charge equilibrium. Graphing the net charge state of a polypeptide (z) vs. pH demonstrates this equilibrium. The curve is created using the amino acid sequence of the polypeptide. The region of the curve with the slope nearest to zero is representative of the charge equilibrium. At equilibrium the polypeptide's net charge state resists change due to a pH change, shown graphically as the flattest region on the curve (FIG. 1). The stability of the polypeptide charge state contributes to assay robustness. The condition where a polypeptide is at equilibrium can be solved by setting the $2^{nd}$ derivative of the equation for the line of z to pH equal to 0. This in an inflection point of a curve where the curve transitions from concave to convex or vice versa. Although there are multiple inflection points (IP) on this curve (not shown in FIG. 1), the inflection point of interest is within the biological region where the absolute value of the slope is no longer decreasing. This IP produces a remarkably robust method due to the stability of the charge state with respect to pH.

A polypeptide's charge equilibrium is an ideal optimal charge for IEC resolution because contaminants with slight differences in net charge compared to a target polypeptide can be detected over a range of pH values. This is due to structure and properties of the amino acids that comprise the polypeptide. Six amino acids are used to calculate the net-charge state (z) (Table 1) because they play an important role in defining the pH-dependent characteristics of a protein. The acid disassociation constants, pKa defined as $(-\log_{10}K_a)$ and based on the constant ratio [A-]/[HA] is used to calculate the charge state of an amino acid. The result is not the actual value, however, but the probability of that charge state, P.

TABLE 1

Acid dissociation constants of select amino acids.

| Amino acid | pKa$_3$ |
|---|---|
| Asparagine; D | 3.65 |
| Glutamic acid; E | 4.25 |
| Histidine; H | 6.02 |
| Tyrosine; Y | 10.1 |
| Lysine; K | 10.53 |
| Arginine; R | 12.48 |

$$P = \left( \frac{10^{(pH-pKa)}}{10^{(pH-pKa)} + 1} \right) \quad \text{Equation 1}$$

For example using Equation 1 for histidine at pH 6.5, $P=10^{(6.5-6)}/(10^{(6.5-6)}+1) \approx 0.76$. This indicates that each histidine residue in a polypeptide containing ten histidine residues at pH 6.5 will have a 76% chance of being unprotonated, rather than a +0.24 charge (1−0.76). In other words, at pH 6.5 approximately three out of every four histidine residues in the polypeptide will be unprotonated. This can be compared to the calculation for the polypeptide at pH 7.5 (FIG. 2B) where nearly all of the histidine residues are deprotonated. The frequency of the most prevalent charge state decreases as the pH approaches the pKa of an amino acid's sidechain.

Figure 3:
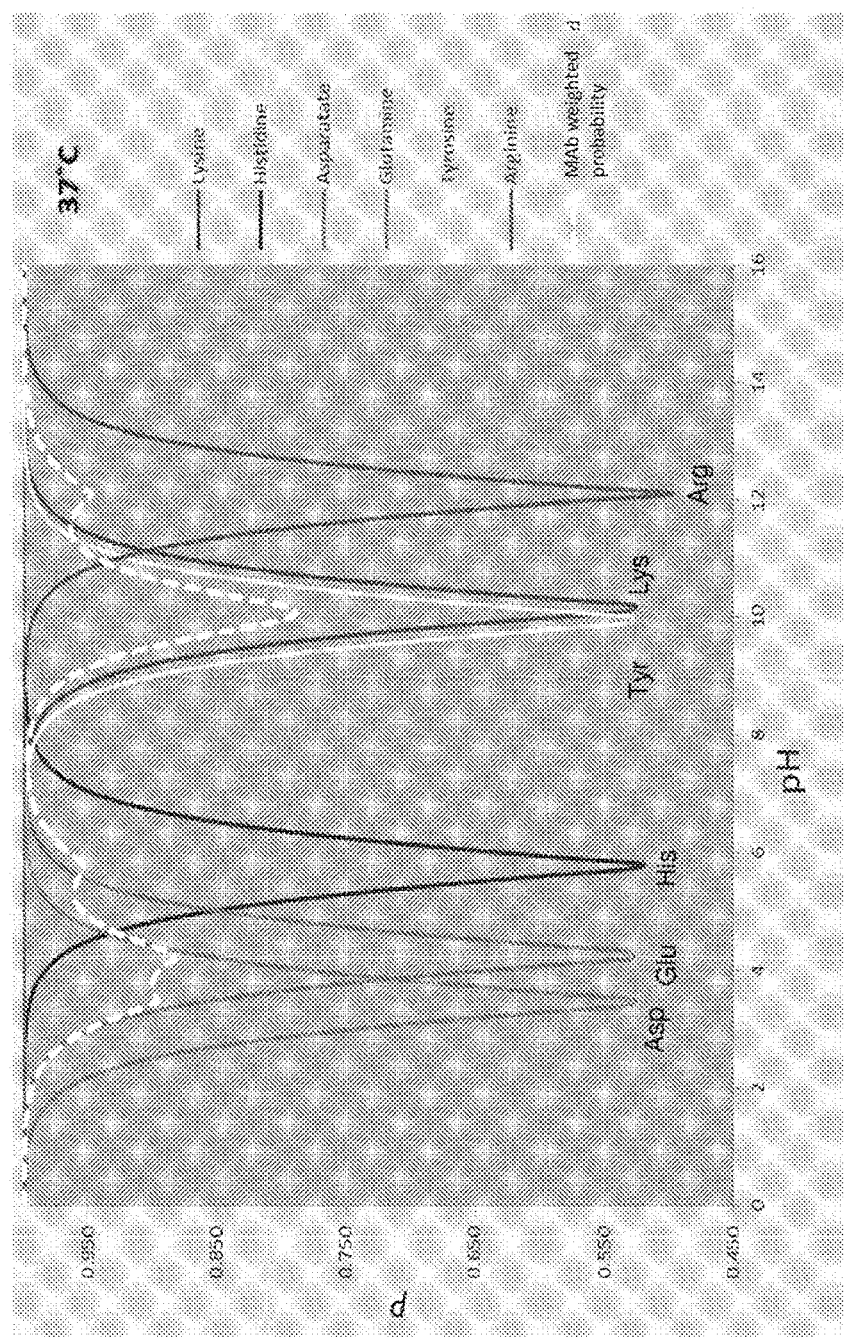
FIG. 3 is a graph of a typical monoclonal antibody in relation to charge frequency for polar amino acids as a function of pH. The probability of most abundant charge state at different pHs for six amino acids contributing to charge calculation at 37 C is plotted as solid lines, and the weighted combination of these amino acid residues for mAb1 is plotted as a dashed line.
Figure 5:
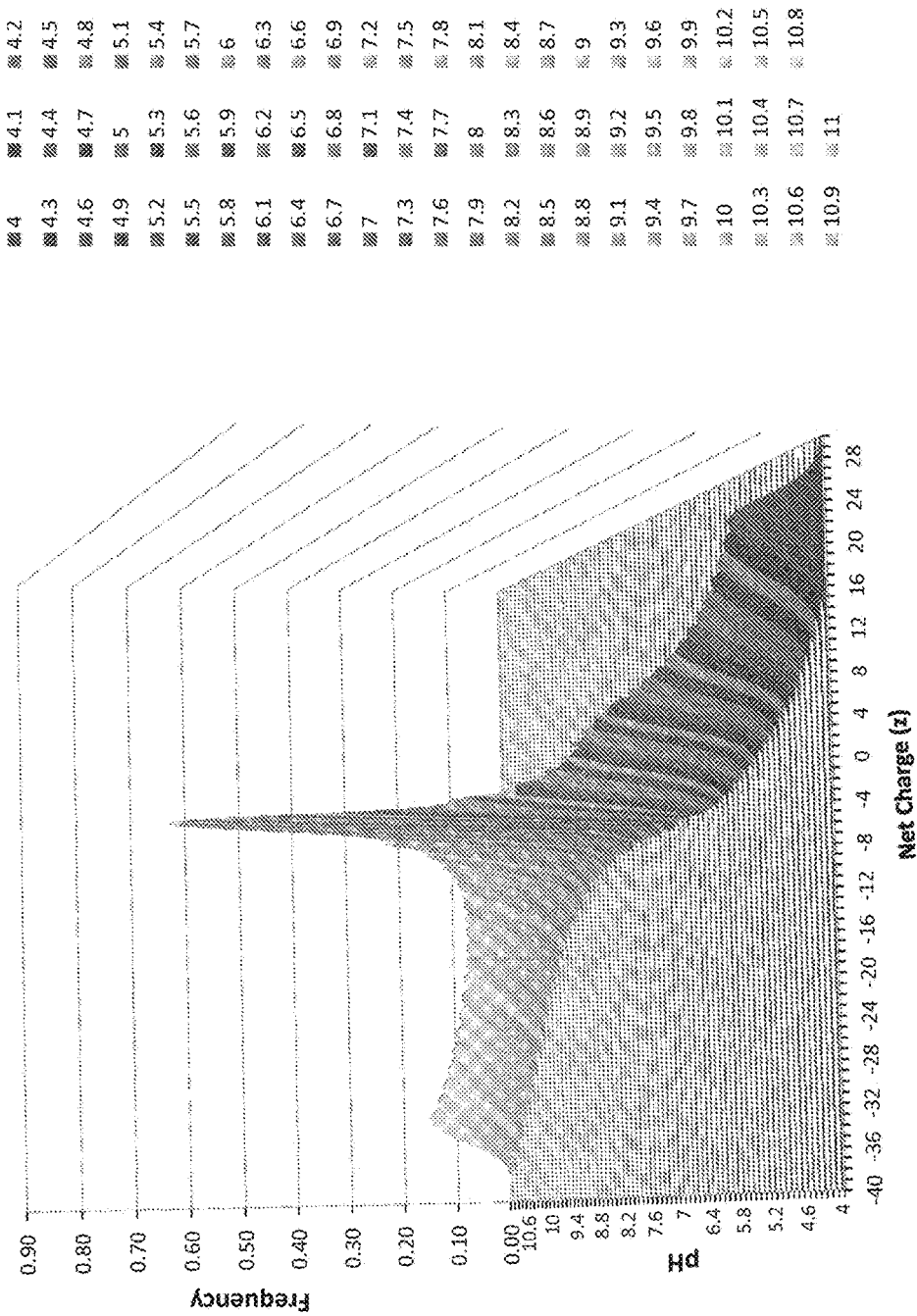
FIG. 5 shows the 3D view of charge distribution and the frequency of charge distribution in a population of mAb1 at different pH at 37° C. It shows that at the inflection point of the net charge vs. pH curve, the charge distribution is the most homogeneous with a frequency at about 0.7; while at pH away from the inflection point, the charge distribution is broader with a frequency of 0.15. Since IEC separation is based on charge, the higher the charge distribution frequency, the narrower the peak and the higher resolution.

Appling this equation to the critical amino acids demonstrates why operating at the equilibrium provides optimal resolution. Weighting the probabilities of the six charge-determining amino acids over the pH range, the most homogenous charge states can be solved (FIG. 3). The presence of a different charge states due to the probable distribution of pronated species will blur the results and hinder the ability to detect contaminants with slight changes in net charge distribution compared to the subject polypeptide. In some embodiments, a 3D graph of net charge distribution vs. pH is plotted. Higher resolution is achieved where the peak of charge vs. pH vs. frequency is the sharpest (FIG. 5). Therefore same conditions of pH and temperature for robustness create optimal resolution.

Figure 4:
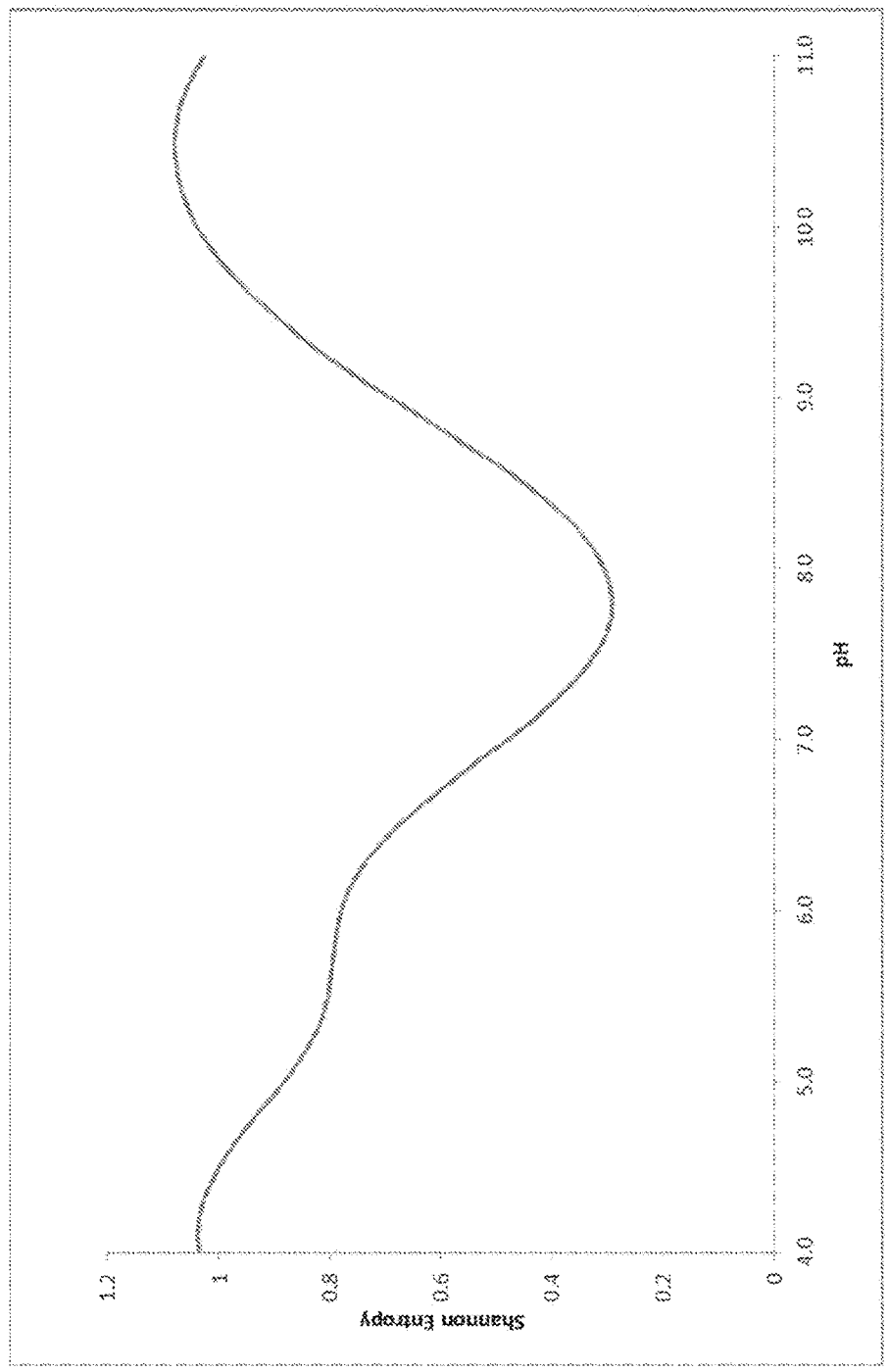
FIG. 4 shows the Shannon entropy of mAb1 at different pHs at 22° C. The type and the number of amino acid residues contributed to net charge calculation are listed in Table 3.

In some embodiments of the invention, the distribution of charge frequency is determined via Shannon entropy, which is a measure of the uncertainty in a random variable (Equation 2). Based on the number of residues of each six amino acids present in the polypeptide (lysine, histidine, aspartate, glutamate, tyrosine and arginine), Shannon entropy at a given pH the polypeptide is plotted as a function of pH (FIG. 4) at a given temperature. The lower the Shannon entropy, the more homogenous the charge distribution. In some embodiments of the invention, the chromatography is performed at a pH and temperature where the Shannon entropy is at about a minimum.

$$H(X) = -\sum_{i=1}^{n} p(x_i)\log_b p(x_i) \quad \text{Equation 2}$$

Where:
- n=possible of outcomes (n=2, either protonated or unprotonated)
- p=probability of outcome or event ($x_i$) (see Equation 1)
- b=# trials (# of charged amino acid residues)

In some embodiments of the invention, the optimal ion exchange chromatography separation conditions are determined for a plurality of different polypeptides such that a common chromatography procedure is used to analyze multiple polypeptide products; e.g. multiple antibody products. In some embodiments, the multiple polypeptide products (e.g., multiple antibody products) are analyzed for the presence of contaminants such as charge variants using a common chromatography procedure identified by the methods described herein. A significant advantage of this invention is that the IP for many polypeptides, including many mAbs, occurs at the same pH (FIG. 7), only differing by the number of charges at that point. Therefore the optimal conditions for all IEC for these polypeptides will be the same; i.e., at the pH and temperature where the polypeptide is at charge equilibrium.

To ensure changes in the conditions would not cause a departure from the IP, the term dIP/dT value is used. The dIP/dT of a protein is the change in a polypeptides's inflection point in a curve of net charge vs. pH with respect to a change in temperature. The inflection point for a given polypeptide will fluctuate based on the temperature for which the plot of net charge vs. pH is determined. However, although the inflection point pH decreases with increasing temperature (e.g. see FIGS. 8 and 9), the net charge remains constant. Therefore, optimizing chromatography for the inflection point also provides ion exchange method robustness against temperature fluctuations.

In some embodiments, the invention provides a means for determining the type of ion exchange chromatography to use for a given polypeptide of multiple polypeptides. For example, if the net charge at the inflection point is positive, a cation exchange chromatography material is used. Non-limiting examples of cation exchange chromatography materials are provided below. In some embodiments, a common cation exchange chromatography procedure is used to analyze a plurality of polypeptides (e.g. antibodies), wherein the plurality of polypeptides have a net positive charge at a common inflection point. If the net charge at the inflection point is negative, an anion exchange chromatography material is used. Non-limiting examples of anion exchange chromatography materials are provided below. In some embodiments, a common anion exchange chromatography procedure is used to analyze a plurality of polypeptides (e.g. antibodies), wherein the plurality of polypeptides have a net negative charge at a common inflection point.

B. Determining Optimal Buffer System

Figure 11:
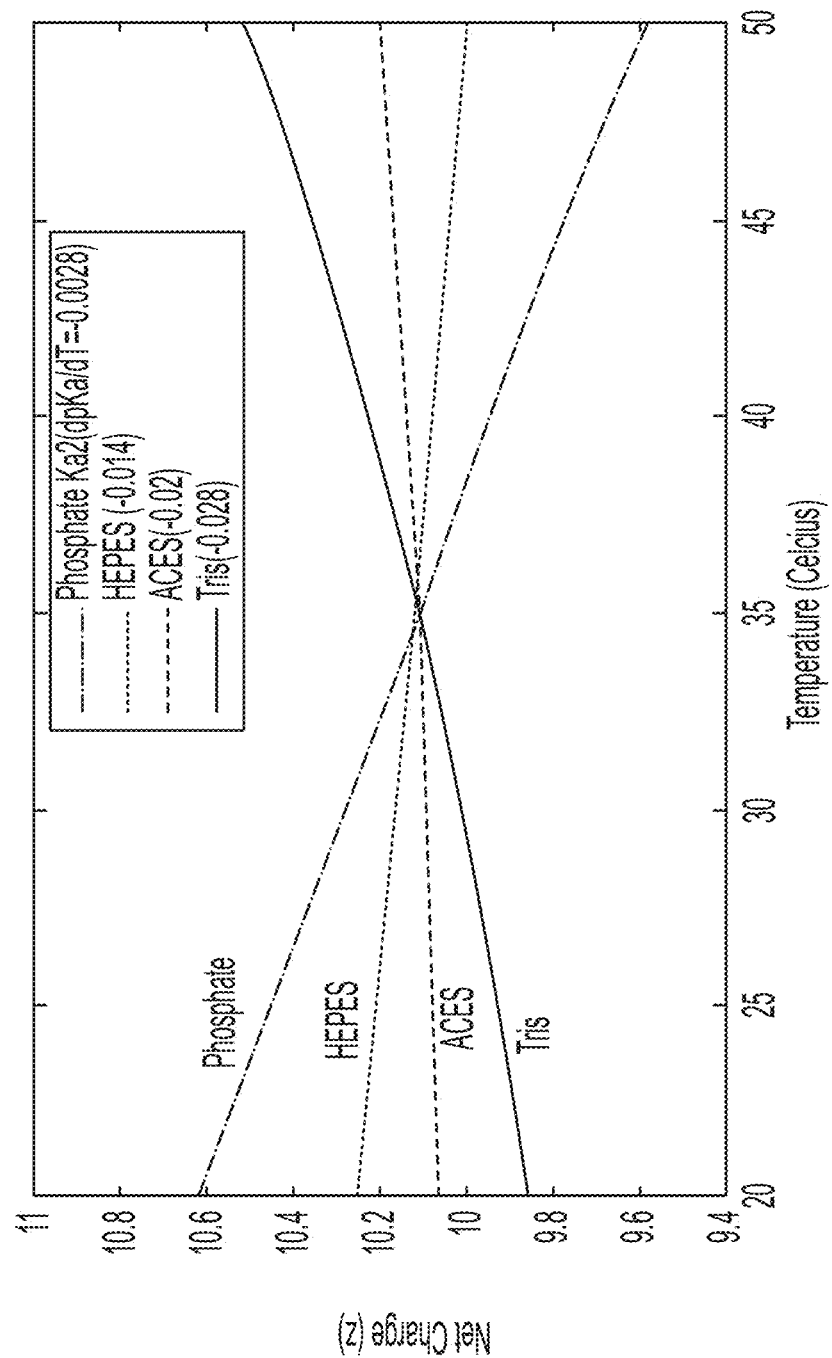
FIG. 11 is a graph showing the net charge for a mAb2 as a function of temperature in a given buffer (phosphate, HEPES, ACES, and Tris).

In some embodiments, the invention provides methods for selecting an optimal buffer to use in the chromatography procedure. In some embodiments, a buffer system with a similar rate of change in acid dissociation constant (pKa) as the change in inflection point with change in temperature is used in the chromatography procedure. Selecting a buffer with a change in pKa with change in temperature (i.e. dpKa/dT) approximately equal to the protein's dIP/dT ensures that any change in temperature will allow the protein to remain at the IP thereby contributing to the robustness of the analytical chromatography. In some embodiments, (dIP/dT)$_{polypeptide(s)}$≈(dpKa/dT)$_{buffer}$. In some embodiments, the buffer is ACES buffer or HEPES buffer. For example using the buffer ACES or HEPES, the charge state of an exemplary mAb at the inflection point changes less than 0.5 over 30° C. (FIG. 11).

$$dIP/dT \approx dpKa/dT \quad \text{Equation 3}$$

In some embodiments, the buffer provides an effective buffering capacity at the inflection point pH. In some embodiments, the dIP/dT of the polypeptide(s) is about −0.02. In some embodiments, the change in temperature is from about 20° C. to about 50° C. In some embodiments, dIP/dT=dpKa/dT±1%, dIP/dT=dpKa/dT±2%, dIP/dT=dpKa/dT±3%, dIP/dT=dpKa/dT±4%, dIP/dT=dpKa/dT±5%, dIP/dT=dpKa/dT±6%, dIP/dT=dpKa/dT±7%, dIP/dT=dpKa/dT±8%, dIP/dT=dpKa/dT±9%, dIP/dT=dpKa/dT±10%, dIP/dT=dpKa/dT±20%, dIP/dT=dpKa/dT±30%, dIP/dT=dpKa/dT±40%, or dIP/dT=dpKa/dT±50%. In some embodiments, the net charge of the polypeptide(s) in the selected buffer changes by less than 1 in over more than about 5° C., 10° C., 15° C., 20° C., 25° C., or 30° C.

In some embodiments, the invention provides methods to develop a high resolution and robust multiproduct polypeptide IEC to detect contaminants such as charge variants. Conditions are designed such that the polypeptide (e.g. mAb) is at charge equilibrium to improve the resolution of charged variants from the parent polypeptide. Charge equilibrium is determined for a number of polypeptide products (e.g. mAb products) by graphing the calculated net charge state (z) vs. pH. The condition where a polypeptide is at equilibrium is solved by setting the 2nd derivative of the equation for the line of z to pH equal to 0.

The net charge of a polypeptide at a given pH is determined based on the content of six amino acids in the mAb that play an important role in defining the pH-dependent characteristics of a protein by virtue of their side chains. The six amino acids are asparagine, glutamic acid, histidine, tyrosine, lysine and arginine. The acid disassociation constants of the six amino acids (pKa, defined as $-\log_{10} Ka$) is used to calculate the net-charge state (z) (Table 1). For example, at pH values below 6.02, on average a histidine is protonated and carries a positive charge whereas at pH values above 6.02, on average a histidine is unprotonated and does not carry a charge. The probability of the most abundant charge state for a given pH was determined for each of the six amino acids and the weighted probability of charge of mAb 1 at a given pH was determined based on the number residues of each of these six amino acids present in the antibody. The distribution of charge frequency can also be determined via Shannon entropy, which is a measure of the uncertainty in a random variable (Equation 3). Based on the number residues of each of these six amino acids present in the polypeptide, the Shannon entropy at a given pH for the polypeptide can be plotted as a function of pH. The lower the Shannon entropy, the more homogenous the charge distribution. From this data, the distribution of the net charge of the polypeptide as a function of pH is plotted and the inflection point (IP) closest to neutral pH is determined. This is the pH with the most homogenous charge state and will result in the sharpest peaks in IEC separation. To develop a multiproduct IEC protocol, the inflection points for a number of target polypeptides (e.g. target MAbs) with different pI's are determined. Targeting the IP can improve pH robustness of the IEC.

The term dIP/dT represents the change in a molecule's IP with a change in the temperature. From these results, an optimal buffer can be chosen where the change in acid dissociation constant of the buffer as a function of temperature approached dIP/dT (i.e., dIP/dT≈dpKa/dT) to minimize the temperature effect and to improve assay robustness. The published values of change in pKa as a function of temperature (dpKa/dT) for a number of buffers is as follows: Phosphate: −0.0028, HEPES: −0.014, ACES: −0.02, Tris: −0.028, Bicine: −0.018, Tricine: −0.021, TAPS: −0.02, and CHES: −0.018 (Benyon, R J & Easterby, J S, Buffer Solutions The Basics, IRL Press, 1996).

In some aspects, the invention provides a method for analyzing a plurality of antibody compositions, wherein each antibody composition comprises an antibody and one or more charge variants of the antibody, wherein the method effectively separates the antibody from its charge variants; for each antibody composition the method comprises, a) binding the antibody and one of more charge variants to an ion-exchange chromatography material using a loading buffer at a flow rate of about 1 mL/minute, wherein the loading buffer comprises 10 mM HEPES buffer at about pH 7.6 at about 40° C.; b) eluting the antibody and the charge variants contaminants from the ion-exchange chromatography material using a gradient of an elution buffer, wherein the elution buffer comprises about 10 mM HEPES buffer at about pH 7.6 and NaCl, wherein the concentration of the NaCl increases in the gradient from about 0 mM to about 80 mM in about 40 minutes, wherein the antibody and its charge variants are separated by the gradient; and c) detecting the antibody and the one or more charge variants. In some embodiments, the plurality of antibody compositions comprises different antibodies. In some embodiments, the plurality of antibody compositions comprises antibodies with different pIs.

C. Chromatography

In some aspects, the invention provides methods of analyzing compositions comprising a polypeptide and one or more contaminants, e.g. polypeptide variants, comprising binding the polypeptide and one or more contaminants to a ion exchange chromatography material using a loading buffer with an initial ionic strength, eluting the polypeptide and one or more contaminants from the ion-exchange column using an elution buffer wherein the ionic strength of the elution buffer is altered by an ionic strength gradient such that the polypeptides and the one or more contaminants elute from the chromatography material as distinct separate entities. In some embodiments, the chromatography methods are suitable for multiple polypeptides (e.g. polypeptide products) with a varying pI's. For example, the methods can be used for a number of different antibody products with pI's ranging from 6.0 to 9.5. In other embodiments, the chromatography methods include use of an optimal buffer identified by the methods described herein.

In some embodiments of any of the methods described herein, the chromatography material is a cation exchange material. In some embodiments, a cation exchange material is used when the polypeptide is positively charged at the inflection point as described herein. In some embodiments, the cation exchange material is a solid phase that is negatively charged and has free cations for exchange with cations in an aqueous solution passed over or through the solid phase. In some embodiments of any of the methods described herein, the cation exchange material may be a membrane, a monolith, or resin. In some embodiments, the cation exchange material may be a resin. The cation exchange material may comprise a carboxylic acid functional group or a sulfonic acid functional group such as, but not limited to, sulfonate, carboxylic, carboxymethyl sulfonic acid, sulfoisobutyl, sulfoethyl, carboxyl, sulphopropyl, sulphonyl, sulphoxyethyl, or orthophosphate. In some embodiments of the above, the cation exchange chromatography material is a cation exchange chromatography column. In some embodiments, an cation exchange chromatography material is used for different polypeptides, e.g. different antibodies or fragment thereof, with pI's ranging from about 7.0 to about 9.5. In some embodiments, the cation exchange chromatography material is used in chromatography methods using an optimal buffer identified by the methods described herein.

Examples of cation exchange materials are known in the art include, but are not limited to Mustang S, Sartobind S, SO3 Monolith, S Ceramic HyperD, Poros XS, Poros HS50, Poros HS20, SPSFF, SP-Sepharose XL (SPXL), CM Sepharose Fast Flow, Capto S, Fractogel Se HiCap, Fractogel SO3, or Fractogel COO. In some embodiments of any of the methods described herein, the cation exchange material is Poros HS50. In some embodiments, the Poros HS resin may be Poros HS 50 µm or Poros HS 20 µm particles. Examples of cation exchange chromatography columns for use in the methods of the invention include, but are not limited to ProPac WCX-10, ProPac WCX-10HT, MabPac SCX-10 5 µm, and MabPac SCX-10 10 µm.

In some embodiments of any of the methods described herein, the chromatography material is an anion exchange material. In some embodiments, an anion exchange material is used when the polypeptide is negatively charged at the inflection point as described herein. In some embodiments, the anion exchange chromatography material is a solid phase that is positively charged and has free anions for exchange with anions in an aqueous solution passed over or through the solid phase. In some embodiments of any of the methods described herein, the anion exchange material may be a membrane, a monolith, or resin. In an embodiment, the anion exchange material may be a resin. In some embodiments, the anion exchange material may comprise a primary amine, a secondary amine, a tertiary amine or a quarternary ammonium ion functional group, a polyamine functional group, or a diethylaminoaethyl functional group. In some embodiments of the above, the anion exchange chromatography material is an anion exchange chromatography column. In some embodiments, an anion exchange chromatography material is used for a polypeptide, e.g. and antibody or fragment thereof, with a pI less than about 7. In some embodiments, an anion exchange chromatography material is used for different polypeptides, e.g. different antibodies or fragment thereof, with pI's ranging from about 4.5 to about 7.0. In some embodiments, the anion exchange chromatography material is used in chromatography methods using an optimal buffer identified by the methods described herein.

Examples of anion exchange materials are known in the art and include, but are not limited to Poros HQ 50, Poros PI 50, Poros D, Mustang Q, Q Sepharose FF, and DEAE Sepharose. Examples of anion exchange chromatography columns for use in the methods of the invention include, but are not limited to Dionex ProPac 10 SAX and Tosoh GSKgel Q STAT 7 µM WAX.

In some embodiments of any of the methods described herein, the chromatography material is a mixed mode material comprising functional groups capable of one of more of the following functionalities: anionic exchange, cation exchange, hydrogen bonding, and hydrophobic interactions. In some embodiments, the mixed mode material comprises functional groups capable of anionic exchange and hydrophobic interactions. The mixed mode material may contain N-benzyl-N-methyl ethanol amine, 4-mercapto-ethyl-pyridine, hexylamine, or phenylpropylamine as ligand or contain cross-linked polyallylamine. Examples of the mixed mode materials include Capto Adhere resin, QMA resin, Capto MMC resin, MEP HyperCel resin, HEA HyperCel resin, PPA HyperCel resin, or ChromaSorb membrane or Sartobind STIC. In some embodiments, the mixed mode material is Capto Adhere resin. In some embodiments of the above, the mixed mode material is a mixed mode chromatography column.

In some embodiments of any of the methods described herein, the ion exchange material may utilize a conventional chromatography material or a convective chromatography material. The conventional chromatography materials include, for example, perfusive materials (e.g., poly(styrene-divinylbenzene) resin) and diffusive materials (e.g., cross-linked agarose resin). In some embodiments, the poly(styrene-divinylbenzene) resin can be Poros resin. In some embodiments, the cross-linked agarose resin may be sulphopropyl-Sepharose Fast Flow ("SPSFF") resin. The convective chromatography material may be a membrane (e.g., polyethersulfone) or monolith material (e.g. cross-linked polymer). The polyethersulfone membrane may be Mustang. The cross-linked polymer monolith material may be cross-linked poly(glycidyl methacrylate-co-ethylene dimethacrylate).

In some embodiments of any of the methods of the invention, the chromatography material is in a chromatography column; for example a cation exchange chromatography column or an anion exchange chromatography column. In some embodiments, the chromatography column is used for liquid chromatography. In some embodiments, the chromatography column is used for high performance liquid chromatography (HPLC). In some embodiments, the chromatography column is an HPLC chromatography column; for example, a cation exchange HPLC column or an anion exchange HPLC column.

An exemplary HPLC procedure that may be used for the multiproduct chromatography methods of the invention is as follows; however, the methods of the invention are not construed to be bound by these procedures. Samples are added to autosampler and are refrigerated (5±3° C.). Columns are placed in the column compartment and a temperature control feature may be employed to keep the compartment temperature within a narrow range (±1° C.) from the set point during analysis. Column effluent is monitored at 280 nm.

Samples are diluted with mobile phase to a target polypeptide concentration of approximately 1-2 mg/mL. In some embodiments, the polypeptide may be digested with carboxypeptidase B (CpB), added in a ratio of 1:100 (w/w) and incubated at 37° C. for 20 min. Samples may be stored at 5° C. until analysis.

The instrument may include a low-pressure quaternary gradient pump, a rapid separation auto-sampler with temperature control capability, a thermal-controlled column compartment and a diode array UV detector. At the outlet of the detector, a PCM-3000 pH and conductivity monitor may be connected to collect pH and conductivity data in real time. Instrument control, data acquisition, and data analysis can be performed; for example, by using Thermo Scientific Dionex Chromeleon software, version 6.8

Samples are diluted to 2 mg/mL with deionized water and may be held at 5±3° C. in the auto-sampler. A MabPac SCX-10, 4×250 mm column is placed in the column compartment with the temperature setting at 37±1° C. For each chromatographic run, 10 µL of protein (20 µg) is injected. Buffer A is 5 mM ACES pH 7.5 at 37° C. Buffer B is 180 mM NaCl in Buffer A. The gradient is 0-100 mM NaCl in 100 min at 1 mM/min by mixing Buffer B into Buffer A. The flow rate is 0.8 mL/min. Protein is detected by absorbance at 280 nm. In some embodiments, Buffer A is 10 mM HEPES buffer pH 7.6 at 40° C. and Buffer B is 100 mM NaCl.

Elution, as used herein, is the removal of the product, e.g. polypeptide, and or contaminants from the chromatography material. Elution buffer is the buffer used to elute the polypeptide or other product of interest from a chromatography material. In some embodiments, the elution buffer is part to the mobile phase of the chromatography. In some embodiments, the composition comprising the polypeptide and the contaminants is applied to the chromatography material as part of the mobile phase. The mobile phase is then altered to allow for separation of the polypeptide from contaminants as the polypeptide and contaminants are eluted from the chromatography material. In many cases, an elution buffer has a different physical characteristic than the load buffer. In some embodiments the ionic strength of the elution buffer is increased over the course of the elution compared to the load buffer. In some embodiments, the chromatography is a multi-product chromatography procedure. In some embodiments, the elution buffer comprises an optimal buffer identified by the methods described herein.

In some embodiments, the ionic strength gradient is a salt gradient. In some embodiments the salt gradient is a gradient from about 0 mM salt to about 200 mM salt. In some embodiments, the salt gradient is any of from about 0 mM to about 100 mM, 0 mM to about 60 mM, 0 mM to about 50 mM, 0 mM to about 40 mM, 0 mM to about 30 mM, 0 mM to about 20 mM, 0 mM to about 10 mM, 10 mM to about 200 mM, 10 mM to about 100 mM, 10 mM to about 50 mM, 10 mM to about 40 mM, 10 mM to about 30 mM, 10 mM to about 20 mM, 20 mM to about 200 mM, 20 mM to about 100 mM, 20 mM to about 50 mM, 20 mM to about 30 mM, 30 mM to about 200 mM, 30 mM to about 100 mM, and 30 mM to about 50 mM.

In some embodiments of the invention, ionic strength of the mobile phase, e.g the elution buffer, is measured by conductivity of the mobile phase. Conductivity refers to the ability of an aqueous solution to conduct an electric current between two electrodes. In solution, the current flows by ion transport. Therefore, with an increasing amount of ions present in the aqueous solution, the solution will have a higher conductivity. The basic unit of measure for conductivity is the Siemen (or mho), mho (mS/cm), and can be measured using a conductivity meter, such as various models of Orion conductivity meters. Since electrolytic conductivity is the capacity of ions in a solution to carry electrical current, the conductivity of a solution may be altered by changing the concentration of ions therein. For example, the concentration of a buffering agent and/or the concentration of a salt (e.g. sodium chloride, sodium acetate, or potassium chloride) in the solution may be altered in order to achieve the desired conductivity. Preferably, the salt concentration of the various buffers is modified to achieve the desired conductivity.

In some embodiments, the mobile phase of the chromatography has an initial conductivity of more than about any of 0.0 mS/cm, 0.5 mS/cm, 1.0 mS/cm, 1.5 mS/cm, 2.0 mS/cm, 2.5 mS/cm, 3.0 mS/cm, 3.5 mS/cm, 4.0 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, 10 mS/cm, 11 mS/cm, 12 mS/cm, 13 mS/cm, 14 mS/cm, 15 mS/cm, 16 mS/cm, 17.0 mS/cm, 18.0 mS/cm, 19.0 mS/cm, or 20.0 mS/cm. In some embodiments, the conductivity of the mobile phase is increased over the course of the chromatography, e.g. by an ionic strength gradient. In some embodiments, the conductivity of the mobile phase at the completion of elution is more than about any of 1.0 mS/cm, 1.5 mS/cm, 2.0 mS/cm, 2.5 mS/cm, 3.0 mS/cm, 3.5 mS/cm, 4.0 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, 10 mS/cm, 11 mS/cm, 12 mS/cm, 13 mS/cm, 14 mS/cm, 15 mS/cm, 16 mS/cm, 17.0 mS/cm, 18.0 mS/cm, 19.0 mS/cm, or 20.0 mS/cm. In some embodiments, the conductivity of the mobile phase is increased by a linear gradient. In some embodiments, the conductivity of the mobile phase is increased by a step gradient comprising one of more steps.

In some embodiments of any of the methods described herein; for example, a multi-product chromatography procedure or a chromatography procedure comprising an optimal buffer identified by the methods described herein, the composition comprising a polypeptide and one or more contaminants is loaded on the chromatography material at an amount of more than any one of about 1 µg, 2 µg, 3 µg, 4 µg, 5 µg, 6 µg, 7 µg, 8 µg, 9 µg, 10 µg, 15 µg, 20 µg, 25 µg, or 50 µg. In some embodiments, the composition is loaded onto the chromatography material at a concentration of more than any one of about 0.5 mg/mL, 1.0 mg/mL, 1.5 mg/mL, 2.0 mg/mL, 2.5 mg/mL, and 5.0 mg/mL. In some embodiments, the composition is diluted prior to loading onto the chromatography material; for example, diluted 1:1, 1:2, 1:5, 1:10 or greater than 1:10. In some embodiments, the composition is diluted into the mobile phase of the chromatography. In some embodiments, the composition is diluted into a loading buffer.

In some embodiments of any of the methods described herein, the flow rate is more than about any of 0.5 mL/min, 0.6 mL/min, 0.7 mL/min, 0.8 mL/min, 0.9 mL/min, 1.0 mL/min, 1.1 mL/min, 1.2 mL/min, 1.3 mL/min, 1.4 mL/min, 1.5 mL/min, 1.75 mL/min and 2.0 mL/min.

In some embodiments of the methods described herein, the chromatography material is in a column. In some embodiments the column is an HPLC column. In some embodiments the column has any one of the following dimensions: 4×50 mm, 4×100 mm, 4×150 mm, 4×200 mm, 4×250 mm, or 2×250 mm.

D. Detection of Charge Variants

In some aspects, the invention provides methods of detecting variants of a polypeptide (e.g. an antibody) in a composition comprising the polypeptide and one or more variants in the composition of the polypeptide. In some embodiments, the variants of the polypeptide are analyzed using ion exchange chromatography separation conditions optimized as described above. In some embodiments, the variants of the polypeptide are analyzed using ion exchange chromatography wherein the buffer has been optimized as described above. In some embodiments, the variants of the polypeptide are analyzed using ion exchange chromatography wherein the separation conditions and the buffer are optimized as described above. In some embodiments, the ion exchange chromatography separation conditions and/or buffer is optimized for a plurality of polypeptides; for example, by identifying a common dIP/dT value for one or more target polypeptides (e.g. one or more antibodies). The method comprising binding the polypeptide and one or more variants to a ion exchange chromatography material using a loading buffer with an initial ionic strength, eluting the polypeptide and one or more contaminants from the ion-exchange column using an elution buffer wherein the ionic strength of the elution buffer is altered by an ionic strength gradient such that the polypeptides and the one or more contaminants elute from the chromatography material as distinct separate entities. The eluents of the chromatography are then analyzed for the parent polypeptide and the presence of variants. Variants of the polypeptide may include acidic variants of the polypeptide and basic variants of the parent polypeptide. Examples of acidic variants, i.e. variants with a pI less than the pI of the parent polypeptide, include but are not limited to polypeptides where one or more glutamine and/or asparagine residues have been deamidated. Examples of basic polypeptide variants, i.e. variants with a pI greater than the pI of the parent polypeptide, include but are not limited to variants where an aspartic acid residue has undergone modification to a succinimide moiety. In some embodiments, the polypeptides have a pI ranging from about 6.0 to about 9.5. In some embodiments, the polypeptide is an antibody having a pI ranging from about 6.0 to about 9.5.

E. Determining the Purity of a Polypeptide in a Composition

In some aspects, the invention provides methods of determining the purity of a polypeptide in a composition comprising the polypeptide. In some embodiments, the purity of the polypeptide in the composition is analyzed using ion exchange chromatography separation conditions optimized as described above. In some embodiments, the purity of the polypeptide in the composition is analyzed using ion exchange chromatography wherein the buffer has been optimized as described above. In some embodiments, the purity of the polypeptide in the composition is analyzed using ion exchange chromatography wherein the separation conditions and the buffer are optimized as described above. In some embodiments, the ion exchange chromatography separation conditions and/or buffer are optimized for a plurality of polypeptides; for example, by identifying a common dIP/dT value for one or more target polypeptides (e.g. one or more antibodies). The method comprising binding the polypeptide and one or more contaminants to a ion exchange chromatography material using a loading buffer with an initial ionic strength, eluting the polypeptide and one or more contaminants from the ion-exchange column using an elution buffer wherein the ionic strength of the elution buffer is altered by an ionic strength gradient such that the polypeptides and the one or more contaminants elute from the chromatography material as distinct separate entities. The purity of the polypeptide can be assessed by determining the ratio of the amount of polypeptide eluting from the chromatography material to the total amount of contaminants, e.g. charge variants, eluting from the chromatography material. In some embodiments, the polypeptides have a pI ranging from about 6.0 to about 9.5. In some embodiments, the polypeptide is an antibody having a pI ranging from about 6.0 to about 9.5.

F. Determining the Stability of a Polypeptide in a Composition

In some aspects, the invention provides methods for determining the stability of a polypeptide in a composition comprising the polypeptide. In some embodiments, the stability of the polypeptide in the composition is determined using ion exchange chromatography wherein the separation conditions are optimized as described above. In some embodiments, the stability of the polypeptide in the composition is determined using ion exchange chromatography wherein the buffer has been optimized as described above. In some embodiments, the stability of the polypeptide in the composition is determined using ion exchange chromatography wherein the separation conditions and the buffer are optimized as described above. In some embodiments, the ion exchange chromatography separation conditions and/or buffer are optimized for a plurality of polypeptides; for example, by identifying a common dIP/dT value for one or more target polypeptides (e.g. one or more antibodies). In some embodiments, samples of the composition comprising the polypeptide are analyzed over time. In some embodiments, the composition is incubated at various times before analysis. In some embodiments, the composition is incubated at more than any one of about 0° C., 20° C., 37° C. or 40° C. prior to analysis. In some embodiments, the composition is incubated for one or more of 1 day, 2 days, 3 days, 5 days, 1 week, 2 weeks, 3 weeks, 4 weeks, 6 weeks, 2 months, 3 months, 6 months, 1 year prior to analysis. The composition is then analyzed by binding the polypeptide and one or more contaminants in the composition to a ion exchange chromatography material using a loading buffer an initial ionic strength, eluting the polypeptide and one or more contaminants from the ion-exchange column using an elution buffer wherein the ionic strength of the elution buffer is altered by an ionic strength gradient such that the polypeptides and the one or more contaminants elute from the chromatography material as distinct separate entities. The change in the ratio of polypeptide to contaminants indicates the stability of the polypeptide in the composition. For example, if the ratio of polypeptide to contaminants does not change over time, the polypeptide may be considered stable whereas the rapid accumulation of contaminants with a concomitant decrease in the amount of polypeptide in the composition indicates the polypeptide in the composition is less stable. In some embodiments, the stability of the polypeptide in the composition is analyzed using ion exchange chromatography wherein the separation conditions optimized as described above. In some embodiments, the stability of the polypeptide in the composition is analyzed using ion exchange chromatography wherein the buffer has been optimized as described above. In some embodiments, the stability of the polypeptide in the composition is analyzed using ion exchange chromatography wherein the separation conditions and the buffer are optimized as described above. In some embodiments, the ion exchange chromatography separation conditions and/or buffer are optimized for a plurality of polypeptides; for example, by identifying a common dIP/dT value for one or more target polypeptides (e.g. one or more antibodies). In some embodiments, the polypeptides have a pI ranging from about 6.0 to about 9.5. In some embodiments, the polypeptide is an antibody having a pI ranging from about 6.0 to about 9.5. Examples of polypeptides include, but are not limited to, antibodies and antibody fragments.

G. Purification of Polypeptides

In some aspects, the invention provides methods of purifying a polypeptide such as an antibody from a composition comprising the polypeptide and one or more contaminants. The method comprising optimizing the chromatography separation conditions as described above. In some embodiments, the polypeptide is purified using chromatography wherein the buffer has been optimized as described above. In some embodiments, the polypeptide is purified using chromatography wherein the separation conditions and the buffer are optimized as described above. In some embodiments, chromatography separation conditions and/or buffer are optimized for a plurality of polypeptides; for example, by identifying a common dIP/dT value for one or more target polypeptides (e.g. one or more antibodies). In some embodiments, the chromatography is ion exchange chromatography; e.g. cation exchange chromatography or anion exchange chromatography. In some embodiments, the chromatography is mixed mode chromatography.

In some embodiments, binding the polypeptide and contaminants to a ion exchange chromatography material or mixed mode chromatography material using a loading buffer with a pH at the inflection point of the polypeptide at the chromatography temperature. The loading buffer has an initial ionic strength. The polypeptide is then eluted from the ion-exchange chromatography media or mixed mode chromatography media using an elution buffer wherein the ionic strength of the elution buffer is altered by an ionic strength gradient such that the polypeptides and the one or more contaminants elute from the chromatography material as distinct separate entities. Fractions are collected during the elution phase of the chromatography and fractions that contain polypeptide with no or minimal contaminants are pooled for further processing or for pharmaceutical formulation. Examples of polypeptides include, but are not limited to, antibodies and antibody fragments.

III. Polypeptides

Polypeptides are provided for use in any of the methods of ion exchange chromatography wherein the separation conditions are optimized as described herein. In some embodiments of the invention, compositions of a polypeptide are analyzed by ion exchange chromatography. Such methods are useful in identifying charge variants of the polypeptide within the composition. In some embodiments, the polypeptide is an antibody or fragment thereof. In some embodiments, the polypeptides have a pI ranging from about 6.0 to about 9.5. In some embodiments, the polypeptide is an antibody having a pI ranging from about 6.0 to about 9.5. In some embodiments, the Inflection Point (IP) in a curve of charge vs. pH of the polypeptide is provided by the methods of the invention. In some embodiments, the change in the IP with a change in temperature (dIP/dT) is provided by the methods of the invention.

In some embodiments, the polypeptide is a therapeutic polypeptide. In some embodiments, the polypeptide is an antibody. In some embodiments, the polypeptide is an immunoadhesin.

In some embodiments, the polypeptide has a molecular weight of greater than about any of 5,000 Daltons, 10,000 Daltons, 15,000 Daltons, 25,000 Daltons, 50,000 Daltons, 75,000 Daltons, 100,000 Dalton, 125,000 Daltons, or 150,000 Daltons. The polypeptide may have a molecular weight between about any of 50,000 Daltons to 200,000 Daltons or 100,000 Daltons to 200,000 Daltons. Alternatively, the polypeptide for use herein may have a molecular weight of about 120,000 Daltons or about 25,000 Daltons.

pI is the isoelectric point and is the pH at which a particular molecule or surface carries no net electrical charge. In some embodiments, the method of the invention can be used for plurality of compositions comprising a polypeptide where the pI of the polypeptide in the composition, e.g. an antibody, ranges from about 6.0 to about 9.5. In some embodiments, the polypeptide has a pI greater than about 9.5; e.g., about 9.5 to about 12. In some embodiments of any of the methods described herein, the pI of the polypeptide, e.g. an antibody, may be less that about 7; e.g., about 4 to about 7.

In embodiments of any of the methods described herein, the one or more contaminants in a composition comprising a polypeptide and one or more contaminants are polypeptide charge variants. In some embodiments, the polypeptide charge variant is a polypeptide that has been modified from its native state such that the charge of the polypeptide is altered. In some embodiments, the charge variants are more acidic than the parent polypeptide; i.e. have a lower pI than the parent polypeptide. In other embodiments, the charge variants are more basic than the parent polypeptide; i.e. have a higher pI than the parent polypeptide. In some embodiments, the polypeptide charge variants are engineered. In some embodiments, the polypeptide charge variant is the result of natural processes; for example, oxidation, deamidation, C-terminal processing of lysine residues, N-terminal pyroglutamate formation, and glycation. In some embodiments, the polypeptide charge variant is a glycoprotein where the glycan attached to the protein is modified such that the charge of the glycoprotein is altered compared to parent glycoprotein; for example, by addition of sialic acid or its derivatives. In some embodiments, the polypeptide charge variant is an antibody charge variant.

The polypeptides to be analyzed using the methods described herein are generally produced using recombinant techniques. Methods for producing recombinant proteins are described, e.g., in U.S. Pat Nos. 5,534,615 and 4,816,567, specifically incorporated herein by reference. In some embodiments, the protein of interest is produced in a CHO cell (see, e.g. WO 94/11026). In some embodiments, the polypeptide of interest is produced in an *E. coli* cell. See, e.g., U.S. Pat. No. 5,648,237; U.S. Pat. No. 5,789,199, and U.S. Pat. No. 5,840,523, which describes translation initiation region (TIR) and signal sequences for optimizing expression and secretion. See also Charlton, Methods in Molecular Biology, Vol. 248 (B. K. C. Lo, ed., Humana Press, Totowa, N.J., 2003), pp. 245-254, describing expression of antibody fragments in *E. coli*. When using recombinant techniques, the polypeptides can be produced intracellularly, in the periplasmic space, or directly secreted into the medium.

The polypeptides may be recovered from culture medium or from host cell lysates. Cells employed in expression of the polypeptides can be disrupted by various physical or chemical means, such as freeze-thaw cycling, sonication, mechanical disruption, or cell lysing agents. If the polypeptide is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating polypeptides which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the polypeptide is secreted into the medium, supernatants from such expression systems are generally first concentrated using a commercially available polypeptide concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

In some embodiments, the polypeptide in the composition comprising the polypeptide and one or more contaminants has been purified or partially purified prior to analysis by the methods of the invention. For example, the polypeptide of the methods is in an eluent from an affinity chromatography, a cation exchange chromatography, an anion exchange chromatography, a mixed mode chromatography and a hydrophobic interaction chromatography. In some embodiments, the polypeptide is in an eluent from a Protein A chromatography.

Examples of polypeptides that may be analyzed by the methods of the invention include but are not limited to immunoglobulins, immunoadhesins, antibodies, enzymes, hormones, fusion proteins, Fc-containing proteins, immunoconjugates, cytokines and interleukins (A) Antibodies In some embodiments of any of the methods described herein, the polypeptide for use in any of the methods of analyzing polypeptides and formulations comprising the polypeptides by the methods described herein is an antibody.

Molecular targets for antibodies include CD proteins and their ligands, such as, but not limited to: (i) CD3, CD4, CD8, CD19, CD11a, CD20, CD22, CD34, CD40, CD79α (CD79a), and CD79β (CD79b); (ii) members of the ErbB receptor family such as the EGF receptor, HER2, HER3 or HER4 receptor; (iii) cell adhesion molecules such as LFA-1, Mac1, p150,95, VLA-4, ICAM-1, VCAM and αv/β3 integrin, including either alpha or beta subunits thereof (e.g., anti-CD11a, anti-CD18 or anti-CD11b antibodies); (iv) growth factors such as VEGF; IgE; blood group antigens; flk2/flt3 receptor; obesity (OB) receptor; mpl receptor; CTLA-4; protein C, BR3, c-met, tissue factor, β7 etc; and (v) cell surface and transmembrane tumor-associated antigens (TAA), such as those described in U.S. Pat. No. 7,521,541.

Other exemplary antibodies include those selected from, and without limitation, anti-estrogen receptor antibody, anti-progesterone receptor antibody, anti-p53 antibody, anti-HER-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11a antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentin antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

(i) Monoclonal Antibodies

In some embodiments, the antibodies are monoclonal antibodies. Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., *Nature* 256:495 (1975), or may be made by recombinant DNA methods (U.S. Pat. No. 4,816,567).

In the hybridoma method, a mouse or other appropriate host animal, such as a hamster, is immunized as herein described to elicit lymphocytes that produce or are capable of producing antibodies that will specifically bind to the polypeptide used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In some embodiments, the myeloma cells are those that fuse efficiently, support stable high-level production of antibody by the selected antibody-producing cells, and are sensitive to a medium such as HAT medium. Among these, in some embodiments, the myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (1984); Brodeur et al., *Monoclonal Antibody Production Techniques and Applications* pp. 51-63 (Marcel Dekker, Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.* 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, polypeptide A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin polypeptide, to obtain the synthesis of monoclonal antibodies in the recombinant host cells. Review articles on recombinant expression in bacteria of DNA encoding the antibody include Skerra et al., *Curr. Opinion in Immunol.* 5:256-262 (1993) and Plückthun, *Immunol. Revs.*, 130:151-188 (1992).

In a further embodiment, antibodies or antibody fragments can be isolated from antibody phage libraries generated using the techniques described in McCafferty et al., *Nature* 348:552-554 (1990). Clackson et al., *Nature* 352: 624-628 (1991) and Marks et al., *J. Mol. Biol.* 222:581-597 (1991) describe the isolation of murine and human antibodies, respectively, using phage libraries. Subsequent publications describe the production of high affinity (nM range) human antibodies by chain shuffling (Marks et al., *Bio/Technology* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison et al., *Proc. Natl Acad. Sci. USA* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In some embodiments of any of the methods described herein, the antibody is IgA, IgD, IgE, IgG, or IgM. In some embodiments, the antibody is an IgG monoclonal antibody.
(ii) Humanized Antibodies In some embodiments, the antibody is a humanized antibody. Methods for humanizing non-human antibodies have been described in the art. In some embodiments, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature* 321:522-525 (1986); Riechmann et al., *Nature* 332:323-327 (1988); Verhoeyen et al., *Science* 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.* 151:2296 (1993); Chothia et al., *J. Mol. Biol.* 196:901 (1987)).

Another method uses a particular framework region derived from the consensus sequence of all human antibodies of a particular subgroup of light or heavy chain variable regions. The same framework may be used for several different humanized antibodies (Carter et al., *Proc. Natl. Acad. Sci. USA* 89:4285 (1992); Presta et al., *J. Immunol.* 151:2623 (1993)).

It is further important that antibodies be humanized with retention of high affinity for the antigen and other favorable biological properties. To achieve this goal, in some embodiments of the methods, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iii) Human Antibodies

In some embodiments, the antibody is a human antibody. As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551 (1993); Jakobovits et al., *Nature* 362:255-258 (1993); Bruggermann et al., *Year in Immuno.* 7:33 (1993); and U.S. Pat. Nos. 5,591,669; 5,589,369; and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat polypeptide gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See also, U.S. Pat. Nos. 5,565,332 and 5,573,905.

Human antibodies may also be generated by in vitro activated B cells (see U.S. Pat. Nos. 5,567,610 and 5,229,275).

(iv) Antibody Fragments

In some embodiments, the antibody is an antibody fragment. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody," e.g., as described in U.S. Pat. No. 5,641,870 for example. Such linear antibody fragments may be monospecific or bispecific.

In some embodiments, fragments of the antibodies described herein are provided. In some embodiments, the antibody fragment is an antigen binding fragment. In some embodiments, the antigen binding fragment is selected from the group consisting of a Fab fragment, a Fab' fragment, a F(ab')$_2$ fragment, a scFv, a Fv, and a diabody.

(v) Bispecific Antibodies

In some embodiments, the antibody is a bispecific antibody. Bispecific antibodies are antibodies that have binding specificities for at least two different epitopes. Exemplary bispecific antibodies may bind to two different epitopes. Alternatively, a bispecific antibody binding arm may be combined with an arm that binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the cell. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. In some embodiments, the fusion is with an immunoglobulin heavy chain constant domain, comprising at least part of the hinge, CH2, and CH3 regions. In some embodiments, the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers that are recovered from recombinant cell culture. In some embodiments, the interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy chain variable domain ($V_H$) connected to a light chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.* 152:5368 (1994).

Antibodies with more than two valencies are contemplated. For example, trispecific antibodies can be prepared. Tutt et al., *J. Immunol.* 147: 60 (1991).

(v) Multivalent Antibodies

In some embodiments, the antibodies are multivalent antibodies. A multivalent antibody may be internalized (and/or catabolized) faster than a bivalent antibody by a cell expressing an antigen to which the antibodies bind. The antibodies provided herein can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2) n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

In some embodiments, the antibody is a multispecific antibody. Example of multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. In some embodiment that antibody has polyepitopic specificity; for example, the ability to specifically bind to two or more different epitopes on the same or different target(s). In some embodiments, the antibodies are monospecific; for example, an antibody that binds only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

(vi) Other Antibody Modifications

It may be desirable to modify the antibody provided herein with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. J., *Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement mediated lysis and ADCC capabilities. See Stevenson et al., *Anti-Cancer Drug Design* 3:219-230 (1989).

For increasing serum half the serum half life of the antibody, amino acid alterations can be made in the antibody as described in US 2006/0067930, which is hereby incorporated by reference in its entirety.

(B) Polypeptide Variants and Modifications

Amino acid sequence modification(s) of the polypeptides, including antibodies, described herein may be used in the methods of purifying polypeptides (e.g., antibodies) described herein.

(i) Variant Polypeptides

"Polypeptide variant" means a polypeptide, preferably an active polypeptide, as defined herein having at least about 80% amino acid sequence identity with a full-length native sequence of the polypeptide, a polypeptide sequence lacking the signal peptide, an extracellular domain of a polypeptide, with or without the signal peptide. Such polypeptide variants include, for instance, polypeptides wherein one or more amino acid residues are added, or deleted, at the N or C-terminus of the full-length native amino acid sequence. Ordinarily, a TAT polypeptide variant will have at least about 80% amino acid sequence identity, alternatively at least about any of 85%, 90%, 95%, 96%, 97%, 98%, or 99% amino acid sequence identity, to a full-length native sequence polypeptide sequence, a polypeptide sequence lacking the signal peptide, an extracellular domain of a polypeptide, with or without the signal peptide. Optionally, variant polypeptides will have no more than one conservative amino acid substitution as compared to the native polypeptide sequence, alternatively no more than about any of 2, 3, 4, 5, 6, 7, 8, 9, or 10 conservative amino acid substitution as compared to the native polypeptide sequence.

The variant polypeptide may be truncated at the N-terminus or C-terminus, or may lack internal residues, for example, when compared with a full length native polypeptide. Certain variant polypeptides may lack amino acid residues that are not essential for a desired biological activity. These variant polypeptides with truncations, deletions, and insertions may be prepared by any of a number of conventional techniques. Desired variant polypeptides may be chemically synthesized. Another suitable technique involves isolating and amplifying a nucleic acid fragment encoding a desired variant polypeptide, by polymerase chain reaction (PCR). Oligonucleotides that define the desired termini of the nucleic acid fragment are employed at the 5' and 3' primers in the PCR. Preferably, variant polypeptides share at least one biological and/or immunological activity with the native polypeptide disclosed herein.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

For example, it may be desirable to improve the binding affinity and/or other biological properties of the polypeptide. Amino acid sequence variants of the polypeptide are prepared by introducing appropriate nucleotide changes into the antibody nucleic acid, or by peptide synthesis. Such modifications include, for example, deletions from, and/or insertions into and/or substitutions of, residues within the amino acid sequences of the polypeptide. Any combination of deletion, insertion, and substitution is made to arrive at the final construct, provided that the final construct possesses the desired characteristics. The amino acid changes also may alter post-translational processes of the polypeptide (e.g., antibody), such as changing the number or position of glycosylation sites.

Guidance in determining which amino acid residue may be inserted, substituted or deleted without adversely affecting the desired activity may be found by comparing the sequence of the polypeptide with that of homologous known polypeptide molecules and minimizing the number of amino acid sequence changes made in regions of high homology.

A useful method for identification of certain residues or regions of the polypeptide (e.g., antibody) that are preferred locations for mutagenesis is called "alanine scanning mutagenesis" as described by Cunningham and Wells, *Science* 244:1081-1085 (1989). Here, a residue or group of target residues are identified (e.g., charged residues such as Arg, Asp, His, Lys, and Glu) and replaced by a neutral or negatively charged amino acid (most preferably Alanine or Polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table 2 below under the heading of "preferred substitutions." If such substitutions result in a change in biological activity, then more substantial changes, denominated "exemplary substitutions" in the Table 2, or as further described below in reference to amino acid classes, may be introduced and the products screened.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, *Biochemistry* second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the polypeptide to improve its stability (particularly where the antibody is an antibody fragment such as an Fv fragment).

A particularly preferred type of substitutional variant involves substituting one or more hypervariable region residues of a parent antibody (e.g., a humanized antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and target. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the polypeptide alters the original glycosylation pattern of the antibody. The polypeptide may comprise non-amino acid moieties. For example, the polypeptide may be glycosylated. Such glycosylation may occur naturally during expression of the polypeptide in the host cell or host organism, or may be a deliberate modification arising from human intervention. By altering is meant deleting one or more carbohydrate moieties found in the polypeptide, and/or adding one or more glycosylation sites that are not present in the polypeptide.

Glycosylation of polypeptide is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Removal of carbohydrate moieties present on the polypeptide may be accomplished chemically or enzymatically or by mutational substitution of codons encoding for amino acid residues that serve as targets for glycosylation. Enzymatic cleavage of carbohydrate moieties on polypeptides can be achieved by the use of a variety of endo- and exo-glycosidases.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group.

(ii) Chimeric Polypeptides

The polypeptide described herein may be modified in a way to form chimeric molecules comprising the polypeptide fused to another, heterologous polypeptide or amino acid sequence. In some embodiments, a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag.

In an alternative embodiment, the chimeric molecule may comprise a fusion of the polypeptide with an immunoglobulin or a particular region of an immunoglobulin. A bivalent form of the chimeric molecule is referred to as an "immunoadhesin."

As used herein, the term "immunoadhesin" designates antibody-like molecules which combine the binding specificity of a heterologous polypeptide with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The Ig fusions preferably include the substitution of a soluble (transmembrane domain deleted or inactivated) form of a polypeptide in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule.

(iii) Polypeptide Conjugates

The polypeptide for use in polypeptide formulations may be conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such conjugates can be used. In addition, enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated polypeptides. Examples include $^{212}Bi$, $^{131}I$, $^{131}In$, $^{90}Y$, and $^{186}Re$. Conjugates of the polypeptide and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the polypeptide.

Conjugates of a polypeptide and one or more small molecule toxins, such as a calicheamicin, maytansinoids, a trichothene, and CC1065, and the derivatives of these toxins that have toxin activity, are also contemplated herein.

Maytansinoids are mitototic inhibitors which act by inhibiting tubulin polymerization. Maytansine was first isolated from the east African shrub *Maytenus serrata*. Subsequently, it was discovered that certain microbes also produce maytansinoids, such as maytansinol and C-3 maytansinol esters. Synthetic maytansinol and derivatives and analogues thereof are also contemplated. There are many linking groups known in the art for making polypeptide-maytansinoid conjugates, including, for example, those disclosed in U.S. Pat. No. 5,208,020. The linking groups include disufide groups, thioether groups, acid labile groups, photolabile groups, peptidase labile groups, or esterase labile groups, as disclosed in the above-identified patents, disulfide and thioether groups being preferred.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Another conjugate of interest comprises a polypeptide conjugated to one or more calicheamicin molecules. The calicheamicin family of antibiotics are capable of producing double-stranded DNA breaks at sub-picomolar concentrations. For the preparation of conjugates of the calicheamicin family, see, e.g., U.S. Pat. No. 5,712,374. Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$. Another anti-tumor drug that the antibody can be conjugated is QFA which is an antifolate. Both calicheamicin and QFA have intracellular sites of action and do not readily cross the plasma membrane. Therefore, cellular uptake of these agents through polypeptide (e.g., antibody) mediated internalization greatly enhances their cytotoxic effects.

Other antitumor agents that can be conjugated to the polypeptides described herein include BCNU, streptozoicin, vincristine and 5-fluorouracil, the family of agents known collectively LL-E33288 complex, as well as esperamicins.

In some embodiments, the polypeptide may be a conjugate between a polypeptide and a compound with nucleolytic activity (e.g., a ribonuclease or a DNA endonuclease such as a deoxyribonuclease; DNase).

In yet another embodiment, the polypeptide (e.g., antibody) may be conjugated to a "receptor" (such streptavidin) for utilization in tumor pre-targeting wherein the polypeptide receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

In some embodiments, the polypeptide may be conjugated to a prodrug-activating enzyme which converts a prodrug (e.g., a peptidyl chemotherapeutic agent) to an active anti-cancer drug. The enzyme component of the immunoconjugate includes any enzyme capable of acting on a prodrug in such a way so as to convert it into its more active, cytotoxic form.

Enzymes that are useful include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs into free active drugs.

(iv) Other

Another type of covalent modification of the polypeptide comprises linking the polypeptide to one of a variety of nonproteinaceous polymers, e.g., polyethylene glycol, polypropylene glycol, polyoxyalkylenes, or copolymers of polyethylene glycol and polypropylene glycol. The polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 18th edition, Gennaro, A. R., Ed., (1990).

IV. Obtaining Polypeptides for Use in the Formulations and Methods

The polypeptides used in the methods of analysis described herein may be obtained using methods well-known in the art, including the recombination methods. The following sections provide guidance regarding these methods.

(A) Polynucleotides

"Polynucleotide," or "nucleic acid," as used interchangeably herein, refer to polymers of nucleotides of any length, and include DNA and RNA.

Polynucleotides encoding polypeptides may be obtained from any source including, but not limited to, a cDNA library prepared from tissue believed to possess the polypeptide mRNA and to express it at a detectable level. Accordingly, polynucleotides encoding polypeptide can be conveniently obtained from a cDNA library prepared from human tissue. The polypeptide-encoding gene may also be obtained from a genomic library or by known synthetic procedures (e.g., automated nucleic acid synthesis).

For example, the polynucleotide may encode an entire immunoglobulin molecule chain, such as a light chain or a heavy chain. A complete heavy chain includes not only a heavy chain variable region ($V_H$) but also a heavy chain constant region ($C_H$), which typically will comprise three constant domains: $C_H1$, $C_H2$ and $C_H3$; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and F(ab')$_2$ and "minibodies." Minibodies are (typically) bivalent antibody fragments from which the $C_H1$ and $C_K$ or $C_L$ domain has been excised. As minibodies are smaller than conventional antibodies they should achieve better tissue penetration in clinical/diagnostic use, but being bivalent they should retain higher binding affinity than monovalent antibody fragments, such as dAbs. Accordingly, unless the context dictates otherwise, the term "antibody" as used herein encompasses not only whole antibody molecules but also antigen-binding antibody fragments of the type discussed above. Preferably each framework region present in the encoded polypeptide will comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions.

VI. Exemplary Embodiments

1. A method for identifying an optimal ion exchange chromatography separation condition to analyze a plurality of compositions, wherein each composition comprises a polypeptide with and one or more contaminants, the method comprising a) plotting a net charge versus pH curve at a selected temperature based on the amino acid composition of the polypeptides of two or more of the compositions, and b) determining the inflection point of the net charge versus pH curve at or near neutral pH by determining the second derivative of the plots of step a); wherein the optimal ion exchange chromatography separation condition is a pH at about a common inflection point for the polypeptides of one or more of the compositions.

2. The method of embodiment 1, wherein if the net charge at the inflection point is positive, a cation exchange material is used for the ion exchange chromatography.

3. The method of embodiment 2, wherein the cation exchange chromatography material is a sulfonated chromatography material or a carboxylated chromatography material.

4. The method of embodiment 1, wherein if the net charge at the inflection point is negative, an anion exchange material is used for the chromatography.

5. The method of embodiment 4, wherein the anion exchange chromatography material is a quarternary amine chromatography material or a tertiary amine chromatography material.

6. The method of embodiment 1, wherein a mixed mode chormatography material is used for the chromatography.

7. The method of embodiment 6, wherein the mixed mode ion exchange material is a mixture of sequentially packed sulfonated chromatography material or carboxylated chromatography material and a quarternary amine chromatography material or tertiary amine chromatography material.

8. The method of any one of embodiments 1-7, further comprising c) determining the change in the inflection point pH of the net charge versus pH curve with a change in the temperature (dIP/dT) for the polypeptides of two or more of the compositions, d) selecting a buffer for use in the chromatography, wherein a change in the acid dissociation constant of the buffer with change in temperature (dpKa/dT) is essentially the same as the dIP/dT of the polypeptides.

9. The method of embodiment 8, wherein the buffer provides an effective buffer capacity at the inflection point pH.

10. The method of any one of embodiments 1-9, wherein the dIP/dT of the polypeptides of one or more of the compositions is about −0.02 pH units.

11. The method of any one of embodiments 1-10, wherein the change in temperature is from about 20° C. to about 70° C.

12. The method of any one of embodiments 1-11, wherein the change in temperature is from about 20° C. to about 50° C.

13. The method of any one of embodiments 8-12, wherein dpKa/dT=dIP/dT±50%.

14. The method of any one of embodiments 8-13, wherein the net charge of the polypeptide in the buffer selected in step d) changes by less than 0.5 over 30° C.

15. The method of any one of embodiments 8-14, wherein the buffer selected in step d) is used in the chromatography at a concentration ranging from about 5 mM to about 250 mM.

16. The method of any one of embodiments 1-15, wherein the buffer compositions further comprise a salt.

17. The method of embodiment 16, wherein the salt is NaCl, KCl, $(NH_4)_2SO_4$, or $Na_2SO_4$.

18. The method of embodiment 16 or 17, wherein the concentration of the salt ranges from about 1 mM to about 1M.

19. The method of any one of embodiments 1-18, wherein the polypeptide is an antibody or immunoadhesin or fragment thereof.

20. The method of any one of embodiments 1-19, wherein the polypeptide is a monoclonal antibody or fragment thereof.

21. The method of embodiment 19 or 20, wherein the antibody is a human antibody.

22. The method of embodiment 19 or 20, wherein the antibody is a humanized antibody.

23. The method of embodiment 19 or 20, wherein the antibody is a chimeric antibody.

24. The method of any one of embodiments 19-23, wherein the antibody is an antibody fragment.

25. The method of any one of embodiments 1-14, wherein the contaminant is a variant of the polypeptide.

26. The method of any one of embodiments 1-25, wherein the contaminant is a degradation product of the polypeptide.

27. The method of any one of embodiments 1-26, wherein the contaminant is a charge variant of the polypeptide.

28. A method for identifying an optimal ion exchange chromatography separation condition to analyze a composition comprising a polypeptide with and one or more contaminants, the method comprising a) plotting a net charge versus pH curve at a selected temperature based on the amino acid composition of the polypeptide, and b) determining the inflection point of the net charge versus pH curve at or near neutral pH by determining the second derivative of the plots of step a); wherein the optimal ion exchange chromatography separation condition is a pH at about the inflection point for the polypeptide.

29. The method of embodiment 28, wherein if the net charge at the inflection point is positive, a cation exchange material is used for the ion exchange chromatography.

30. The method of embodiment 29, wherein the cation exchange chromatography material is a sulfonated chromatography material or a carboxylated chromatography material.

31. The method of embodiment 28, wherein if the net charge at the inflection point is negative, an anion exchange material is used for the chromatography.

32. The method of embodiment 31, wherein the anion exchange chromatography material is a quarternary amine chromatography material or a tertiary amine chromatography material.

33. The method of embodiment 28, wherein a mixed mode chormatography material is used for the chromatography.

34. The method of embodiment 33, wherein the mixed mode ion exchange material is a mixture of sequentially packed sulfonated chromatography material or carboxylated chromatography material and a quarternary amine chromatography material or tertiary amine chromatography material.

35. The method of any one of embodiments 28-34, further comprising c) determining the change in the inflection point pH of the net charge versus pH curve with a change in the temperature (dIP/dT) for the polypeptide, d) selecting a buffer for use in the chromatography, wherein a change in the acid dissociation constant of the buffer with change in temperature (dpKa/dT) is essentially the same as the dIP/dT of the polypeptide.

36. The method of embodiment 35, wherein the buffer provides an effective buffer capacity at the inflection point pH.

37. The method of any one of embodiments 28-36, wherein the dIP/dT of the polypeptides of one or more of the compositions is about −0.02 pH units.

38. The method of any one of embodiments 28-37, wherein the change in temperature is from about 20° C. to about 70° C.

39. The method of any one of embodiments 28-38, wherein the change in temperature is from about 20° C. to about 50° C.

40. The method of any one of embodiments 28-39, wherein dIP/dT=dpKa/dT±50%.

41. The method of any one of embodiments 28-40, wherein the net charge of the polypeptide in the buffer selected in step d) changes by less than 0.5 over 30° C.

42. The method of any one of embodiments 28-41, wherein the buffer selected in step d) is used in the chromatography at a concentration ranging from about 5 mM to about 50 mM.

43. The method of any one of embodiments 28-42, wherein the buffer composition further comprise a salt.

44. The method of embodiment 43, wherein the salt is NaCl, KCl, $(NH_4)_2SO_4$, or $Na_2SO_4$.

45. The method of embodiment 43 or 44, wherein the concentration of the salt ranges from about 10 mM to about 1M.

46. The method of any one of embodiments 28-45, wherein the polypeptide is an antibody or immunoadhesin or fragment thereof.

47. The method of any one of embodiments 28-46, wherein the polypeptide is a monoclonal antibody or fragment thereof.

48. The method of embodiment 46 or 47, wherein the antibody is a human antibody.

49. The method of embodiment 46 or 47, wherein the antibody is a humanized antibody.

50. The method of embodiment 46 or 47, wherein the antibody is a chimeric antibody.

51. The method of any one of embodiments 38-50, wherein the antibody is an antibody fragment.

52. The method of any one of embodiments 28-51, wherein the contaminant is a variant of the polypeptide.

53. The method of any one of embodiments 28-52, wherein the contaminant is a degradation product of the polypeptide.

54. The method of any one of embodiments 28-53, wherein the contaminant is a charge variant of the polypeptide.

55. A method for analyzing a composition, wherein the composition comprises a polypeptide and one or more contaminants, wherein the method effectively separates polypeptides from the contaminants, the method comprising a) determining the optimal pH and temperature ion exchange separation conditions for a plurality of compositions, each composition comprising a target polypeptide and one or more contaminants according to the method of embodiment 1, b) binding the polypeptide and one of more contaminants from the composition to an ion-exchange chromatography material using a loading buffer, wherein the loading buffer comprises a buffer identified by the method of any one of embodiments 8-15; c) eluting the polypeptide and one or more contaminants from the ion-exchange chromatography material using a gradient of an elution buffer, wherein the elution buffer comprises the buffer and a salt, wherein the concentration of the salt increases in a gradient over time, wherein the polypeptide and the one or more contaminants are separated by the gradient; and d) detecting the polypeptide and the one or more contaminants.

56. A method for analyzing a composition comprising a polypeptide and one or more contaminants, wherein the method effectively separates the polypeptide from the contaminants, the method comprising a) binding the polypeptide and one of more contaminants to an ion-exchange chromatography material using a loading buffer, wherein the loading buffer comprises a buffer, and wherein the pH and temperature of the chromatography has been optimized for a plurality of target polypeptides by i) plotting a net charge versus pH curve at a selected temperature, wherein the curve is based on the amino acid composition of the polypeptide of two or more target polypeptides, and ii) determining the inflection point of the net charge versus pH curve by determining the second derivative of the plots of step i); wherein the optimal ion exchange chromatography condition is a pH at a common inflection point for two or more target polypeptides; b) eluting the polypeptide and one or more contaminants from the ion-exchange chromatography material using a gradient of an elution buffer, wherein the elution buffer comprises the buffer and a salt, wherein the polypeptide and the one or more contaminants are separated by the gradient; and c) detecting the polypeptide and the one or more contaminants.

57. The method of embodiment 56, wherein the selected temperature is ambient temperature.

58. The method of embodiment 56 or 57, wherein the buffer is identified by a) determining the change in the inflection point pH of the net charge versus pH curve with a change in the temperature (dIP/dT) for the two or more target polypeptides, b) selecting a buffer for which a change in the acid dissociation constant buffer with change in temperature (dpKa/dT) is essentially the same as the dIP/dT of the one or more target polypeptides with common inflection points.

59. The method of embodiment 58, wherein the buffer provides an effective buffer capacity at the inflection point pH.

60. A method for analyzing a composition comprising a polypeptide and one or more contaminants, wherein the method effectively separates the polypeptide from the contaminants, the method comprising a) binding the polypeptide and one of more contaminants to an ion-exchange chromatography material using a loading buffer, wherein the loading buffer comprises a buffer, and wherein the pH and temperature of the chromatography has been optimized for a plurality of target polypeptides; b) eluting the polypeptide and one or more contaminants from the ion-exchange chromatography material using a gradient of an elution buffer, wherein the elution buffer comprises the buffer and a salt, wherein the polypeptide and the one or more contaminants are separated by the gradient; and c) detecting the polypeptide and the one or more contaminants.

61. The method of embodiment 60, wherein the buffer is N-(2-Acetamido)-2-aminoethanesulfonic acid (ACES) or 4-(2-hydroxyethyl)-1-piperazineethanesulfonic acid (HEPES).

62. The method of any one of embodiments 55-61, wherein the concentration of the buffer ranges from about 5 mM to about 20 mM.

63. The method of any one of embodiments 55-62, wherein the pH of the buffer ranges from about 6.5 to about 8.5 at a temperature range of about 20° C. to about 70° C.

64. The method of any one of embodiments 55-63, wherein the pH of the buffer ranges from about 6.5 to about 8.5 at a temperature range of about 20° C. to about 50° C.

65. The method of any one of embodiments 55-64, wherein the pH of the buffer and the polypeptide at the inflection point is about 7.8 at about 22° C., about 7.5 at about 37° C., or about 7.2 at about 50° C.

66. The method of any one of embodiments 55-65, wherein the salt gradient is a linear gradient.

67. The method of any one of embodiments 55-66, wherein the salt gradient is a step gradient.

68. The method of any one of embodiments 55-67, wherein the salt gradient is a NaCl gradient, a KCl gradient, $(NH_4)_2SO_4$, or a $Na_2SO_4$ gradient.

69. The method of any one of embodiments 55-68 wherein the salt concentration in the gradient increases from about 0 mM to about 1M.

70. The method of embodiment 69, wherein the salt concentration increases from about 0 mM to about 100 mM in about 100 minutes.

71. The method of embodiment 69, wherein the salt concentration increases from about 0 mM to about 80 mM in about 40 minutes.

72. The method of embodiment any one of embodiments 55-71, wherein the polypeptide is an antibody or immunoadhesin or fragment thereof.

73. The method of any one of embodiments 55-72, wherein the polypeptide is a monoclonal antibody or fragment thereof.

74. The method of embodiment 72 or 73, wherein the antibody is a human antibody.

75. The method of embodiment 72 or 73, wherein the antibody is a humanized antibody.

76. The method of embodiment 72 or 73, wherein the antibody is a chimeric antibody.

77. The method of any one of embodiments 72-76, wherein the antibody is an antibody fragment.

78. The method of any one of embodiments 55-77, wherein the contaminant is a variant of the polypeptide.

79. The method of any one of embodiments 55-78, wherein the contaminant is a degradation product of the polypeptide.

80. The method of any one of embodiments 55-79, wherein the contaminant is a charge variant of the polypeptide.

81. The method of any one of embodiments 55-80, wherein the chromatography material is a cation exchange chromatography material.

82. The method of embodiment 81, wherein the cation exchange chromatography material is a sulfonated chromatography material or a carboxylated chromatography material.

83. A method for analyzing a plurality of polypeptide compositions, wherein each polypeptide composition comprises an polypeptide and one or more charge variants of the polypeptide, wherein the method effectively separates the polypeptide from its charge variants;
for each polypeptide composition the method comprises, a) binding the polypeptide and one of more charge variants to an ion-exchange chromatography material using a loading buffer at a flow rate of about 1 mL/minute, wherein the loading buffer comprises 10 mM HEPES buffer at about pH 7.6 at about 40° C.; b) eluting the polypeptide and the charge variants contaminants from the ion-exchange chromatography material using a gradient of an elution buffer, wherein the elution buffer comprises about 10 mM HEPES buffer at about pH 7.6 and a NaCl, wherein the concentration of the NaCl increases in the gradient from about 0 mM to about 80 mM in about 40 minutes, wherein the polypeptide and its charge variants are separated by the gradient; and c) detecting the polypeptide and the one or more charge variants.

84. The method of embodiment 83, wherein the plurality of polypeptide compositions comprises different polypeptides.

85. The method of embodiment 83 or 84, wherein the plurality of polypeptide compositions comprises polypeptides with different pIs.

86. The method of any one of embodiments 83-85, wherein the polypeptide compositions are antibody compositions.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further details of the invention are illustrated by the following non-limiting Examples. The disclosures of all references in the specification are expressly incorporated herein by reference.

EXAMPLES

The examples below are intended to be purely exemplary of the invention and should therefore not be considered to limit the invention in any way. The following examples and detailed description are offered by way of illustration and not by way of limitation.

Materials and Methods for Examples

The following materials and methods were used for the examples unless otherwise noted.
Materials
All mAbs were manufactured using stable Chinese Hamster Ovary (CHO) cell lines or *Escherichia coli* cells.
MabPac SCS-10 and Propac WCX-10 columns were purchased from ThermoFisher. AntiBodix columns were from Sepax. YMC columns were purchased from YMC. Trisma (Tris) were obtained from Mallinckrodt Baker Inc. or Sigma (St. Louis, Mo.), and HEPES, ACES, Trizma base and CAPS was obtained from Sigma. Sodium chloride, sodium hydroxide (10 N) and hydrochloric acid (12 N) were obtained from Mallinckrodt Baker Inc. Phosphoric acid (85%) was obtained from EMD Millipore.
HPLC Set up
Cation-exchange chromatography experiments were primarily performed on a Waters 2796 BioAlliance liquid chromatography instrument, Agilent 1200SL HPLC system, or an UltiMate 3000 Quaternary Rapid Separation LC (Thermo Scientific Dionex). The instrument included a low-pressure quaternary gradient pump or a binary pump, an auto-sampler with temperature control capability, a thermal column compartment for precise temperature control, and a dual-wavelength diode array UV detector. Instrument control, data acquisition, and data analysis were performed with Dionex Chromeleon software, version 6.8.

Example 1. Optimization of Multi-Product Analytical Ion Exchange Chromatography

To develop a high resolution and robust multiproduct IEC to detect contaminants such as charge variants, conditions were designed such that the mAb's was at charge equilibrium. Charge equilibrium was determined for a number of mAb products by graphing the net charge state (z) vs. pH. The condition where a mAb is at equilibrium was solved by setting the 2nd derivative of the equation for the line of z to pH equal to 0.

Figure 2A:
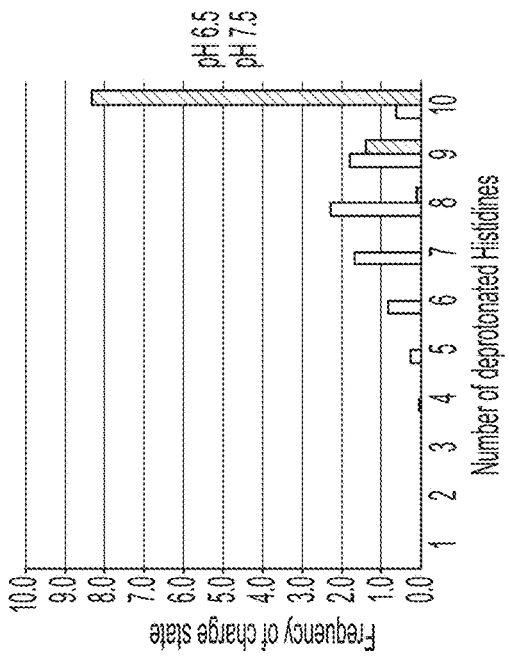
FIG. 2A shows a graph of the percentage of protonated histidines (positively charged) in a population (e.g. a polypeptide solution) over the pH scale.
Figure 2B:
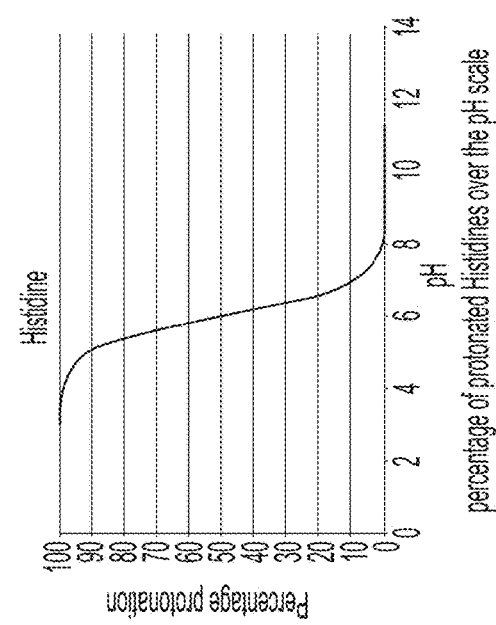
FIG. 2B shows the number of deprotonated histidines (charge frequency) in a polypeptide containing ten histidine residues at pH 6.5 and pH 7.5. It shows that the inflection point (pH 7.5), most of the histidine residues are deprotonated and not charged.
Figure 2C:
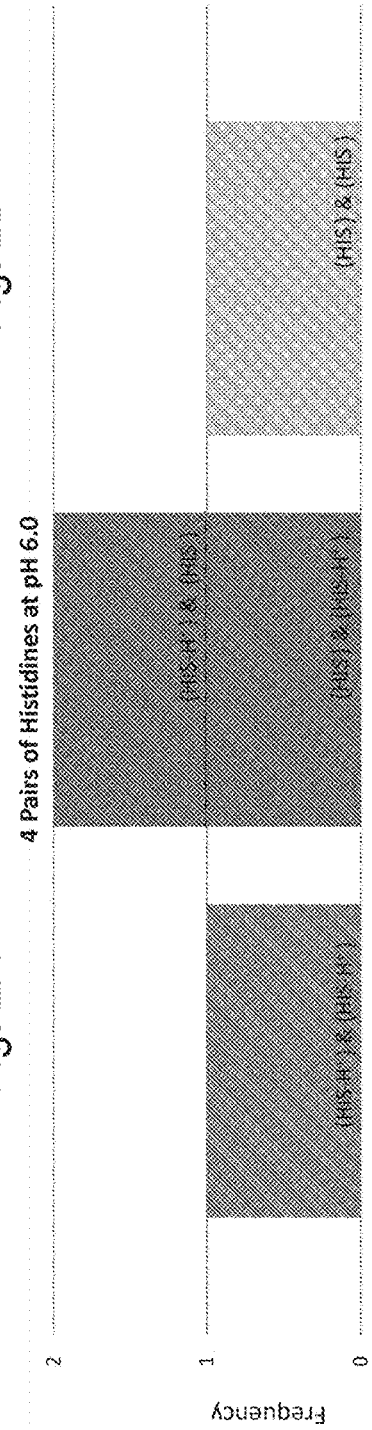
FIG. 2C shows an example of four polypeptide molecules, each with two histidine residues. At the pKa of His (pH 6.0), 50% of His residues are protonated, and 50% are deprotonated. The charge state combination of His residues on these four molecules is a binomial distribution at pKa: one with both His protonated; two with one His protonated and another deprotonated; and one with both His deprotonated.

The net charge of a mAb at a given pH was determined based on the content of six amino acids in the mAb that play an important role in defining the pH-dependent characteristics of a protein by virtue of their side chains. The six amino acids are asparagine, glutamic acid, histidine, tyrosine, lysine and arginine. The acid disassociation constants of the six amino acids (pKa, defined as −log 10 Ka) were used to calculate the net-charge state (z). For example, MAb1 has 10 histidine residues. FIG. 2 shows the protonation of histidine as a function of pH. At pH values below histidine's pKa of 6.02, the histidine is protonated and carries a positive charge (FIG. 2A). At pH values above 6.02, the histidine is deprotonated and does not carry a charge. Using Equation 1, the probability of a particular charge state for histidine at a particular pH was determined. FIG. 2B shows the probable distribution of deprotonated histidine in mAb1 at pH 6.5 and at pH 7.5. At pH 6.5, mAb1 had a median of 8 deprotonated histidine residues whereas at pH 7.5 nearly all the histidine residues were deprotonated. FIG. 2C shows an example with four polypeptide molecules, each with two histidine residues. At pKa (pH 6.02), 50% of His residues are protonated, and 50% are deprotonated. The charge state combination of histidine residues on these four molecules is a binomial distribution at pKa: one with both histidines protonated; two with one histidine protonated and another deprotonated; and one with both histidines deprotonated.

The probability of the most abundant charge state for a given pH was determined for each of the six amino acids and the weighted probability of charge of mAb1 at a given pH was determined based on the number residues of each of these six amino acids present in the antibody (FIG. 3). The distribution of charge frequency can also be determined via Shannon entropy, which is a measure of the uncertainty in a random variable (Equation 3). Based on the number residues of each of these six amino acids present in mAb1 (Table 3), Shannon entropy at a given pH for mAb1 is plotted in FIG. 4. The lower the Shannon entropy, the more homogenous the charge distribution.

TABLE 3

Number of selected amino acids residues in mAb1

| pH | lysine | histidine | aspartate | glutamate | tyrosine | arginine |
|---|---|---|---|---|---|---|
| No. residues | 90 | 28 | 52 | 64 | 66 | 32 |

Figure 6:
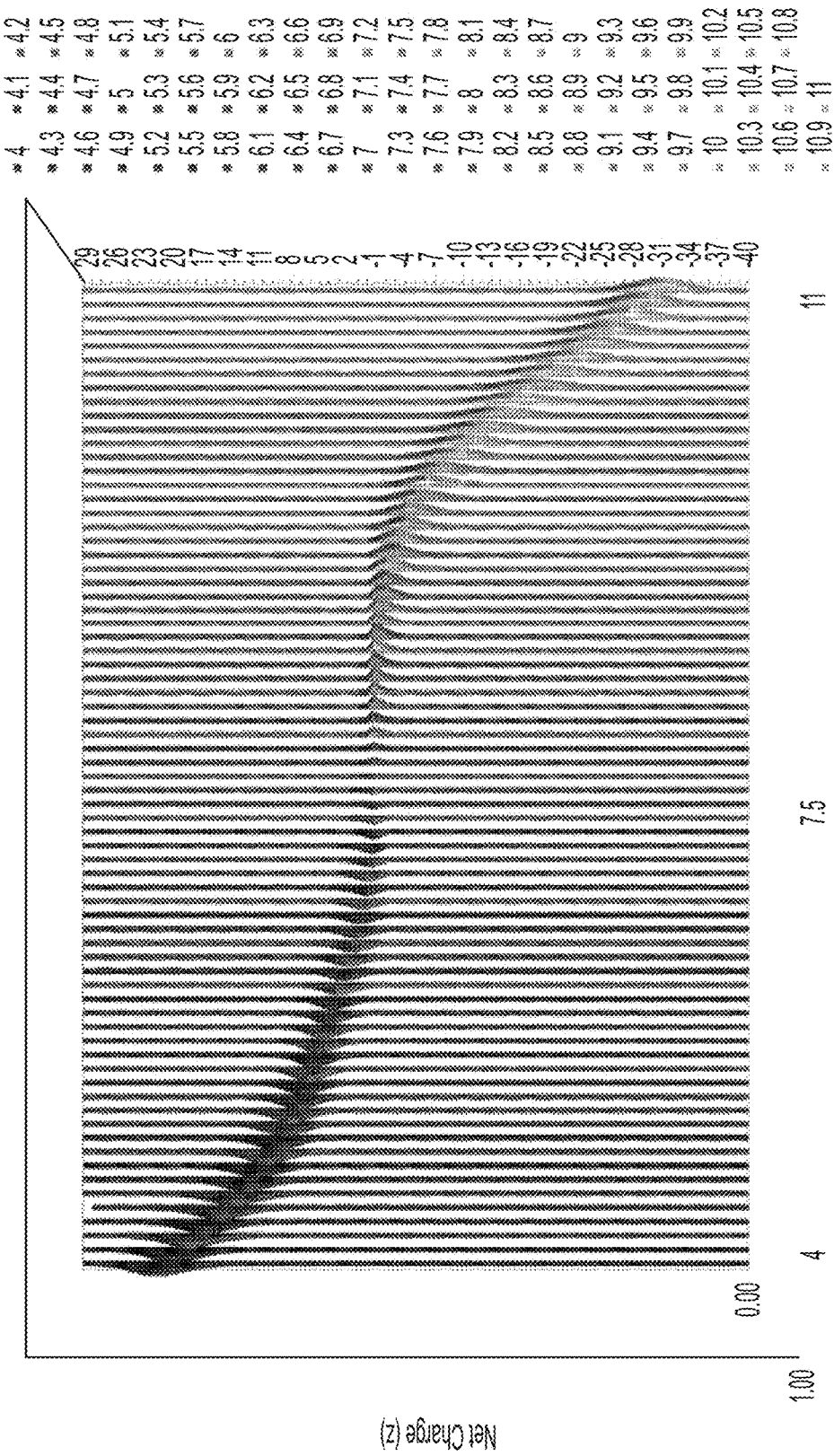
FIG. 6 is the 2D illustration of FIG. 5, a net charge vs. pH curve for mAb1. The inflection point is at pH 7.5 when temperature is 37° C.

From this data, the distribution of the net charge of mAb1 as a function of pH was plotted (FIG. 5) and the inflection point was determined to be pH 7.5 at 37° C. (FIG. 6, which is the top view of FIG. 5). Note that this is the pH with the most homogenous charge state, shown as the tallest and sharpest peaks in FIG. 5. The most homogenous charge state will also result in the sharpest peak in IEC separation.

Figure 7:
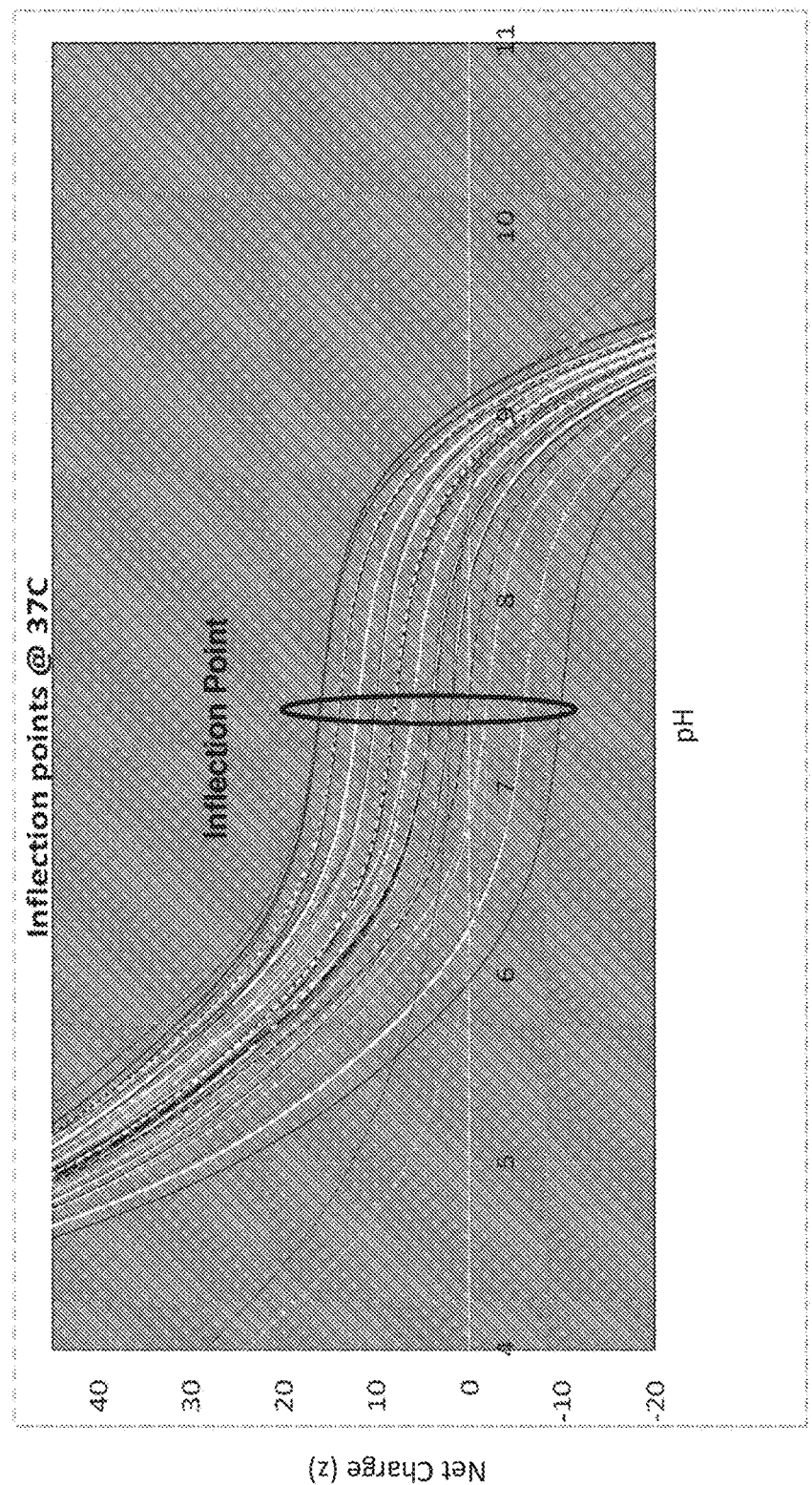
FIG. 7 is a graph showing net charge as a function of pH for a number of mAb products at 37° C. The calculated net charge of each mAb was calculated based on the amino acid sequence of the mAb. Some mAbs had different framework amino acid sequences. The inflection point of all curves is around pH 7.5 at 37° C.

Using the method described above, the inflection points for a number of mAbs with pI's ranging from 7.6 to 9.4 were determined (FIG. 7). Surprisingly, the inflection point for nearly all mAbs was the same, pH 7.5 at 37° C. Targeting the IP can improve pH robustness of the IEC. As shown in FIG. 7, the net charge varies little for all antibodies between pH 7 and pH 8.

Figure 8:
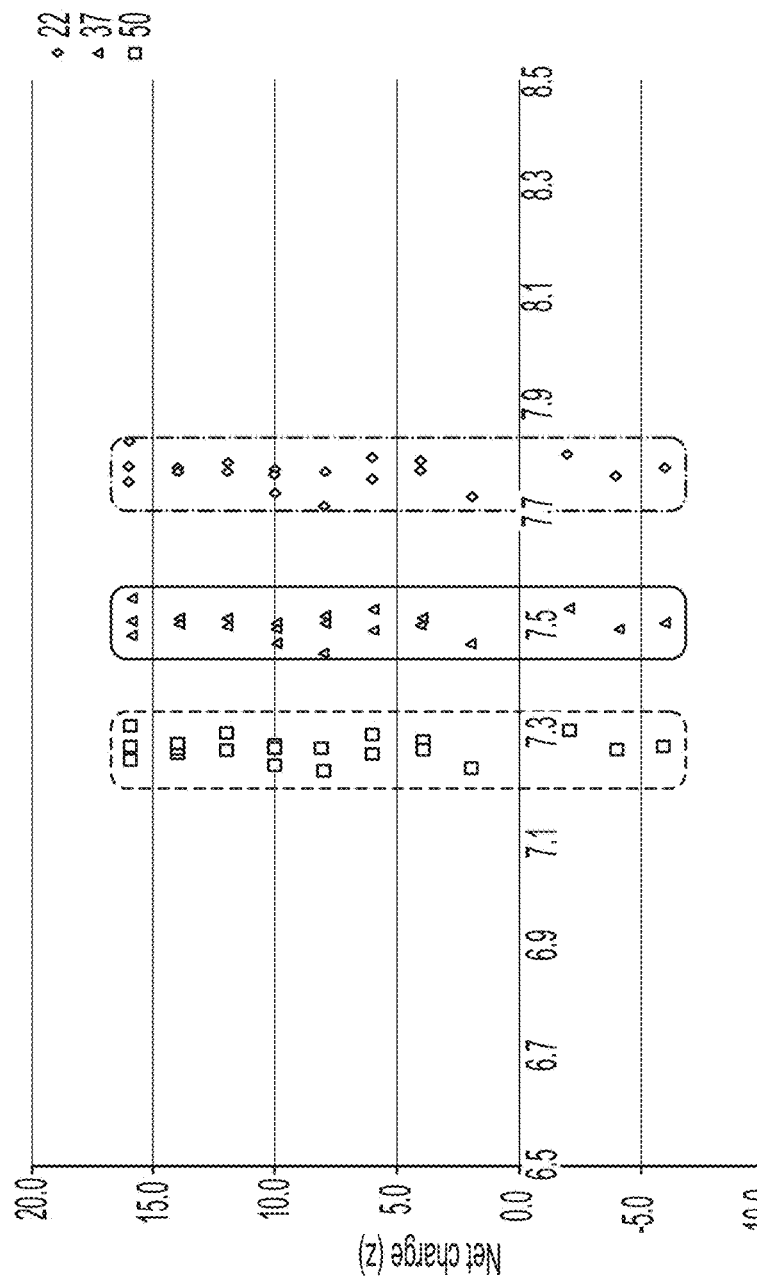
FIG. 8 is a graph showing the calculated inflection points for a number of mAb products at 22° C. (diamonds), 37° C. (triangles) and 50° C. (squares).

The inflection points for the mAbs was determined as 22° C., 37° C. and 50° C. As shown in FIG. 8, although the inflection points were dependent on the temperature, the inflection points for all antibodies tested were similar at a given temperature.

Figure 9:
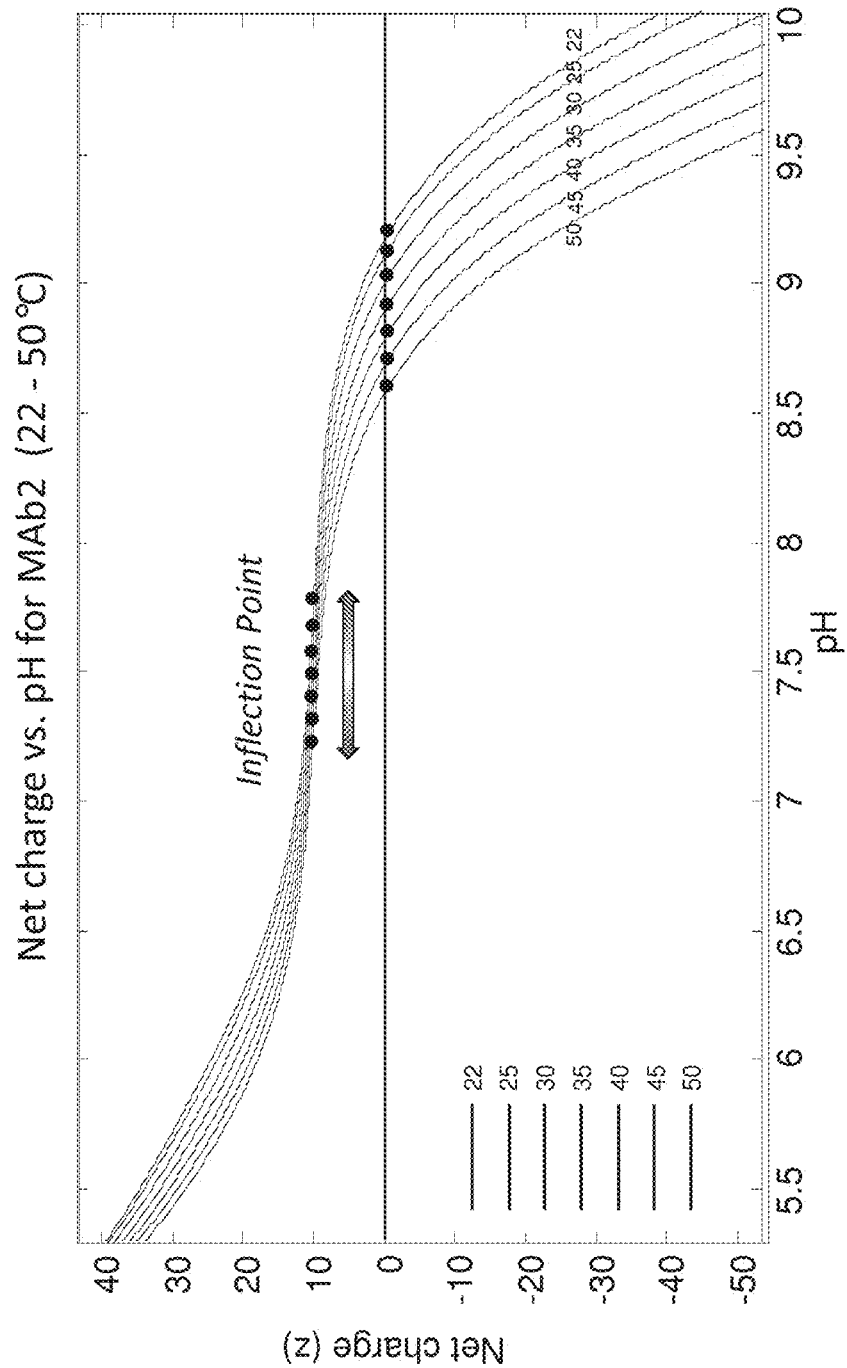
FIG. 9 is a graph showing the relationship of net charge to pH for mAb2 at temperatures ranging from 22° C. to 50° C.

The inflection point for mAb2 was determined for temperatures ranging from 22° C. to 50° C. As seen in FIG. 9, while the inflection point pH decreases with the increase in temperature, the net charge remains constant. Therefore, optimizing the chromatography for the inflection point also provides IEX method robustness against temperature fluctuation. The term dIP/dT represents the change in a molecule's IP with a change in the temperature. From these results, an optimal buffer can be chosen where the change in acid dissociation constant of the buffer as a function of temperature approached dIP/dT (i.e., dIP/dT≈dpKa/dT) to minimize the temperature effect and to improve assay robustness.

Figure 10A:
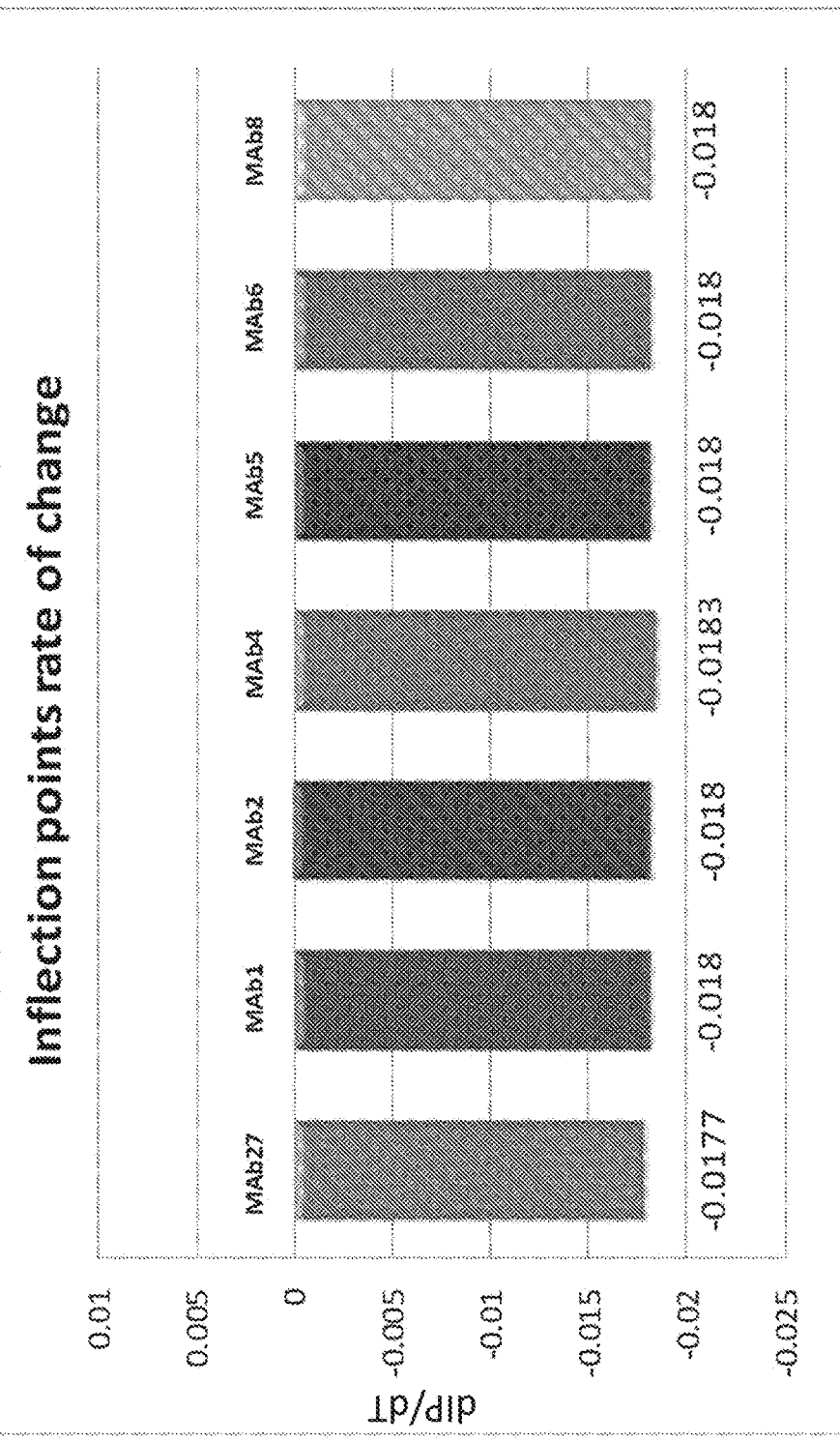
FIG. 10A shows the inflection points rate of change.
Figure 10B:
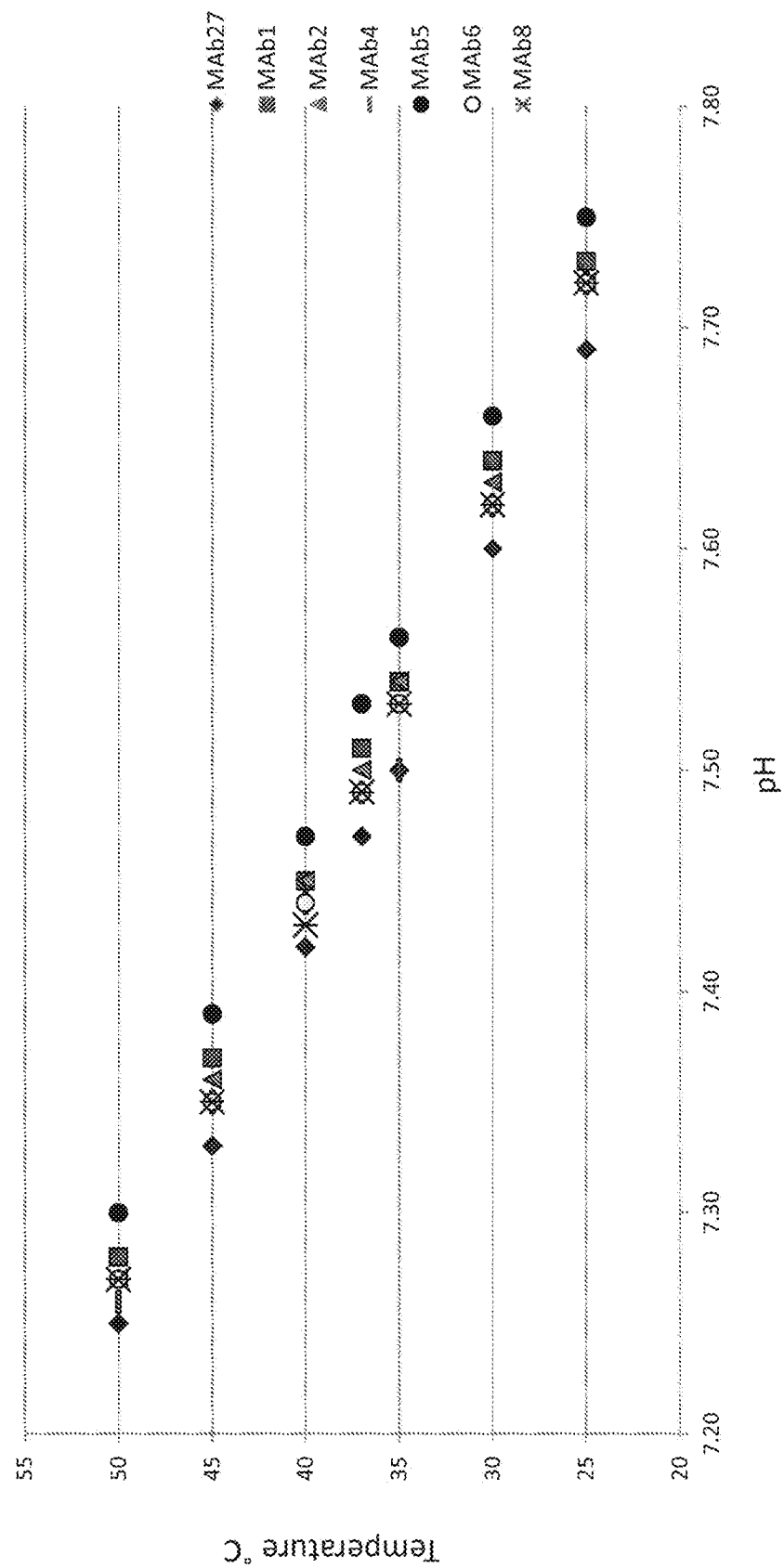
FIG. 10B shows the change in dIP as a function of temperature for selected mAbs. The rate of change is nearly identical.

The relationship between the inflection point pH and temperature was plotted and the slope of the linear regression, dIP/dT values, were calculated for a number of mAbs with different pI values (FIG. 10 and Table 4). It was found that the dIP/dT values for these six mAbs are essentially the same (−0.0177 to −0.0183). As such, a buffer with a dpKa/dT value of about −0.018 would be optimal for IEC analysis all of the mAbs presented in FIG. 10 and therefore optimal for a multi-product IEC.

TABLE 4

Inflection points (pH)

| Temp ° C. | MAb27 | MAb1 | MAb2 | MAb4 | MAb5 | MAb6 | MAb8 |
|---|---|---|---|---|---|---|---|
| 25 | 7.69 | 7.73 | 7.72 | 7.72 | 7.75 | 7.72 | 7.72 |
| 30 | 7.60 | 7.64 | 7.63 | 7.62 | 7.66 | 7.62 | 7.62 |
| 35 | 7.50 | 7.54 | 7.54 | 7.53 | 7.56 | 7.53 | 7.53 |
| 37 | 7.47 | 7.51 | 7.50 | 7.49 | 7.53 | 7.49 | 7.49 |
| 40 | 7.42 | 7.45 | 7.45 | 7.44 | 7.47 | 7.44 | 7.44 |
| 45 | 7.33 | 7.37 | 7.36 | 7.35 | 7.39 | 7.35 | 7.35 |
| 50 | 7.25 | 7.28 | 7.27 | 7.26 | 7.30 | 7.27 | 7.27 |
| dIP/dT | −0.0177 | −0.018 | −0.018 | −0.0183 | −0.018 | −0.018 | −0.018 |

The published values of change in pKa as a function of temperature (dpKa/dT) for a number of buffers is as follows:
Phosphate: −0.0028
HEPES: −0.014
ACES: −0.02
Tris: −0.028
Bicine: −0.018
Tricine: −0.021
TAPS: −0.02
CHES: −0.018
See Benyon, R J & Easterby, J S, Buffer Solutions The Basics, IRL Press, 1996.

FIG. 11 shows a graph of the net charge at the inflection point of mAb2 in phosphate buffer, HEPES buffer, ACES buffer and Tris buffer as a function of temperature. The graphs of the net charge of mAb2 in ACES buffer or HEPES buffer was nearly flat changing less than 0.5 over a 30° C. range. On the other hand, the graphs for Tris and phosphate were not as flat, showing greater change in net charge with a change in temperature. It was concluded that ACES or HEPES are optimal buffers for a multi-product IEC analysis.

Example 2. Development of a Multi-Product IEC Protocol

Figure 12:
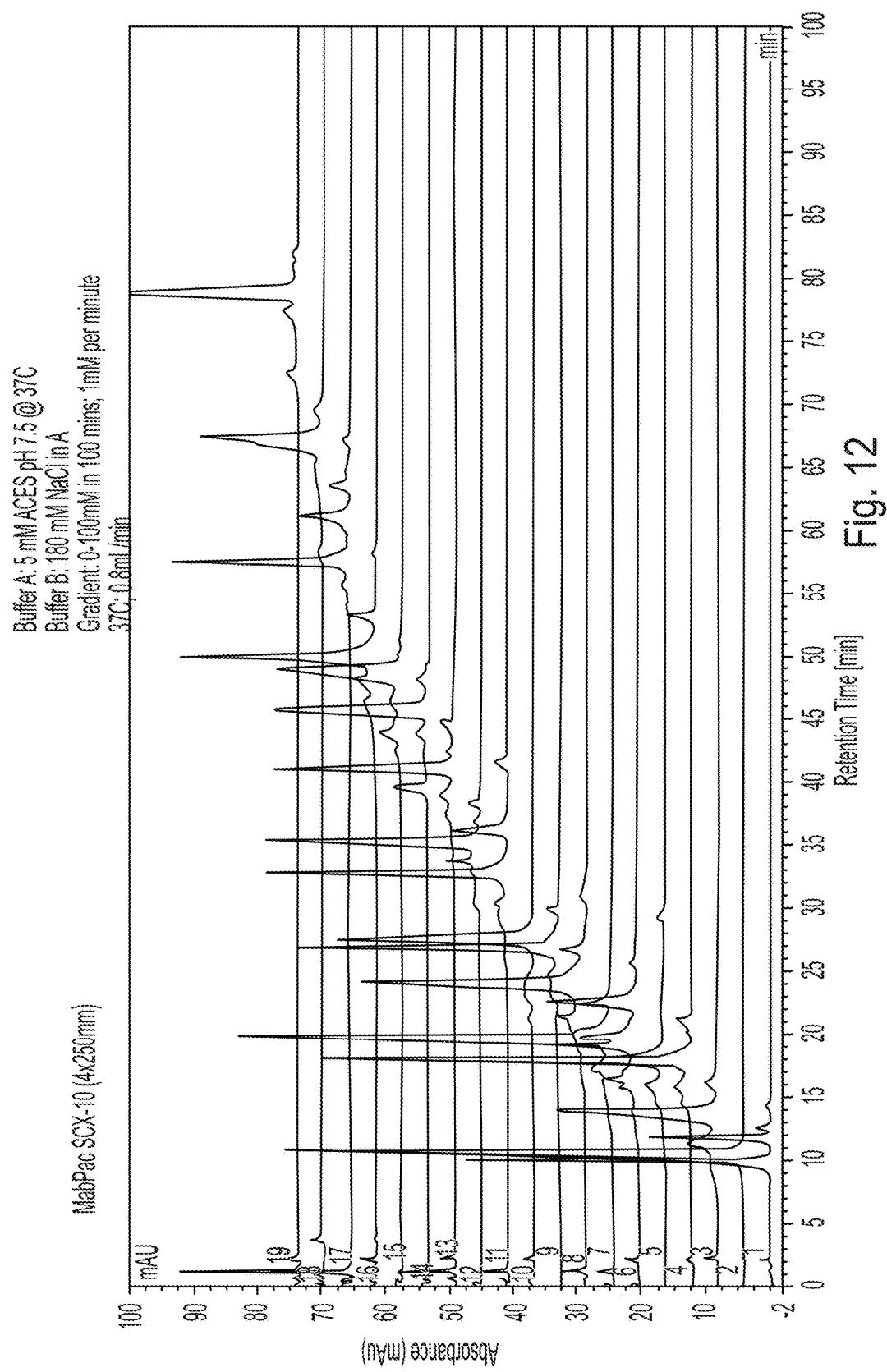
FIG. 12 shows overlaid chromatograms of a number of mAbs with different pI's using the same chromatography procedure. Buffer A was 5 mM ACES pH 7.5 at 37° C. Buffer B was 180 mM NaCl in Buffer A. The salt gradient was 0 mM NaCl to 100 mM NaCl in 100 minutes or 1 mM/min at 37° C. The flow rate was 0.8 mL/min. The column was a MabPac SCX-10 column (4×250 mm).

A multi-product IEC protocol was developed in view of the inflection point and the relationship of the dpKa/dT value for ACES and HEPES and the dIP/dT values determined for a number of mAbs. 19 mAbs were tested. mAb samples were diluted to 1 mg/mL with buffer A and were kept at 5±3° C. in the auto-sampler. The MabPac SCX-10, 4×250 mm column was placed in the column compartment with the temperature setting at 37±1° C. For each chromatographic run, 10 μL of protein (20 μg) was injected. Buffer A was 5 mM ACES pH 7.5 at 37° C. Buffer B was 180 mM NaCl in Buffer A. The gradient was 0-100 mM NaCl in 100 min at 1 mM/min by mixing Buffer B into Buffer A. The flow rate was 0.8 mL/min. Protein was detected by absorbance at 280 nm. As shown in FIG. 12, the multi-produce IEC provided good resolution for a broad range of mAb products.

Example 3. pH Robustness of Multi-Product IEC

The pH robustness of the multi-product IEC was examined using the method described in Example 2 except the gradient was 1.5 mM NaCl/min and at three different pH values, pH 7.3, pH 7.5 and pH 7.7. mAb4 was used as an non-limiting exemplary antibody for this study.

Figure 13:
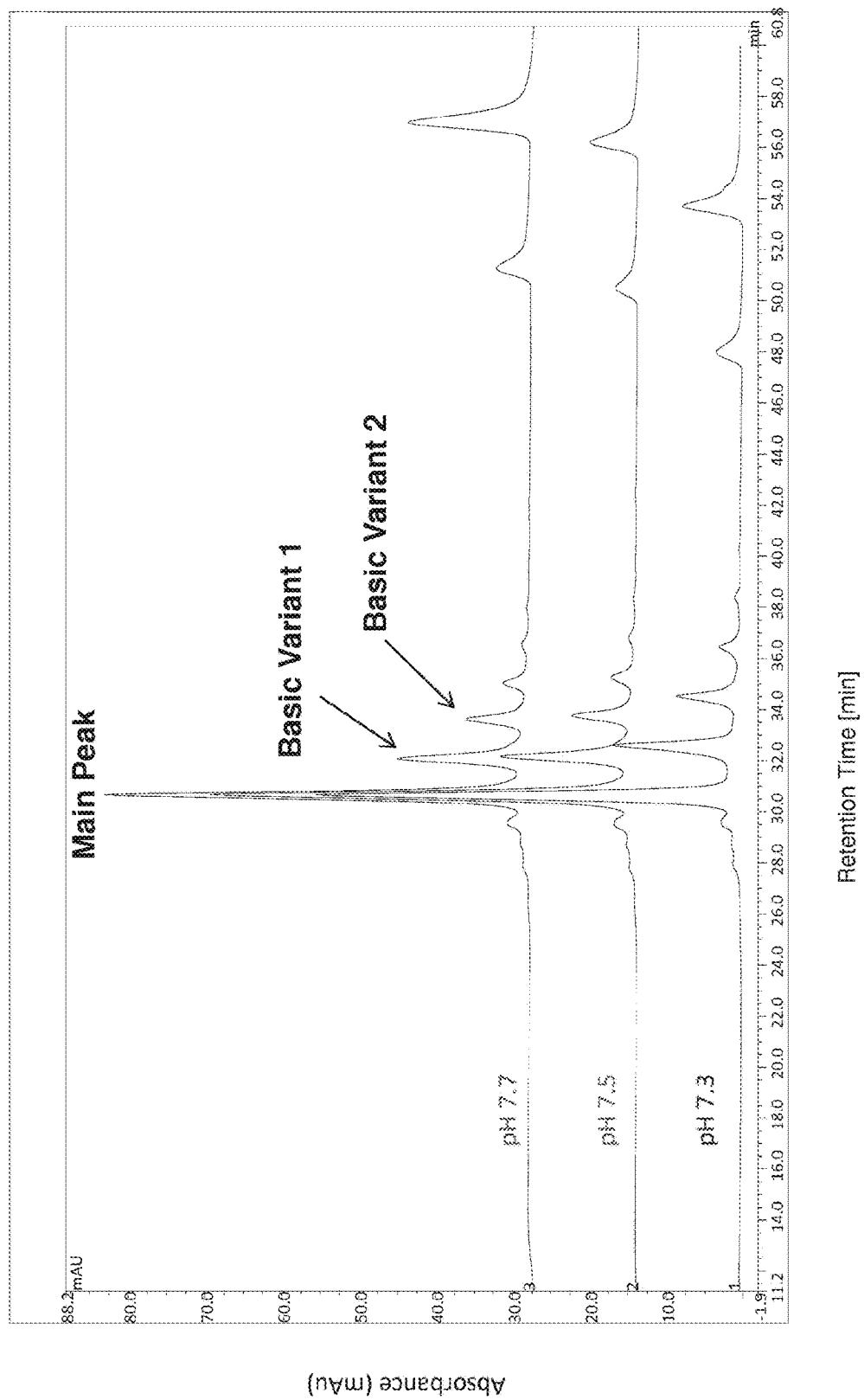
FIG. 13 shows the robustness of an IEC for mAb4 as a function of pH. The chromatography conditions are as in FIG. 12 except the gradient was 1.5 mM NaCl/min.

As shown in FIG. 13, good resolution between the antibody main peak and its charge variants were seen at all pH values tested. Quantification of peak areas revealed no significant changes in analysis with respect to pH (Table 5).

TABLE 5 pH robustness of multi-product IEC

| pH | % acidic | % Main Peak | % Basic 1 | % Basic 2 | Total Basic | Resolution[a] Main/BV1 | BV1/BV2 |
|---|---|---|---|---|---|---|---|
| 7.7 | 8.4 | 52.1 | 21.1 | 18.4 | 39.5 | 2.3 | 2.2 |
| 7.5 | 8.4 | 53.3 | 21.0 | 18.3 | 39.3 | 2.3 | 2.3 |
| 7.3 | 8.6 | 52.4 | 21.3 | 17.7 | 39.0 | 3.0 | 2.7 |

[a]Resolution defined by Equation 4.

$$R = \frac{(t_{r2} - t_{r1})}{1/2(w_1 + w_2)}.$$ Equation 4 where R is resolution $t_{r1}$ and $t_{r2}$ are the retention times of the two immediately adjacent peaks $w_1$ and $w_2$ are the peak widths of the two immediately adjacent peaks Example 4. Temperature Robustness The temperature robustness of the multi-product IEC was examined using the method described in Example 2 except the gradient was 1.5 mM NaCl/min and at three different temperatures 32° C., 37° C., and 42° C. mAb2, mAb6 and mAb 10 were used as an non-limiting exemplary antibodies for this study.

Figure 14:
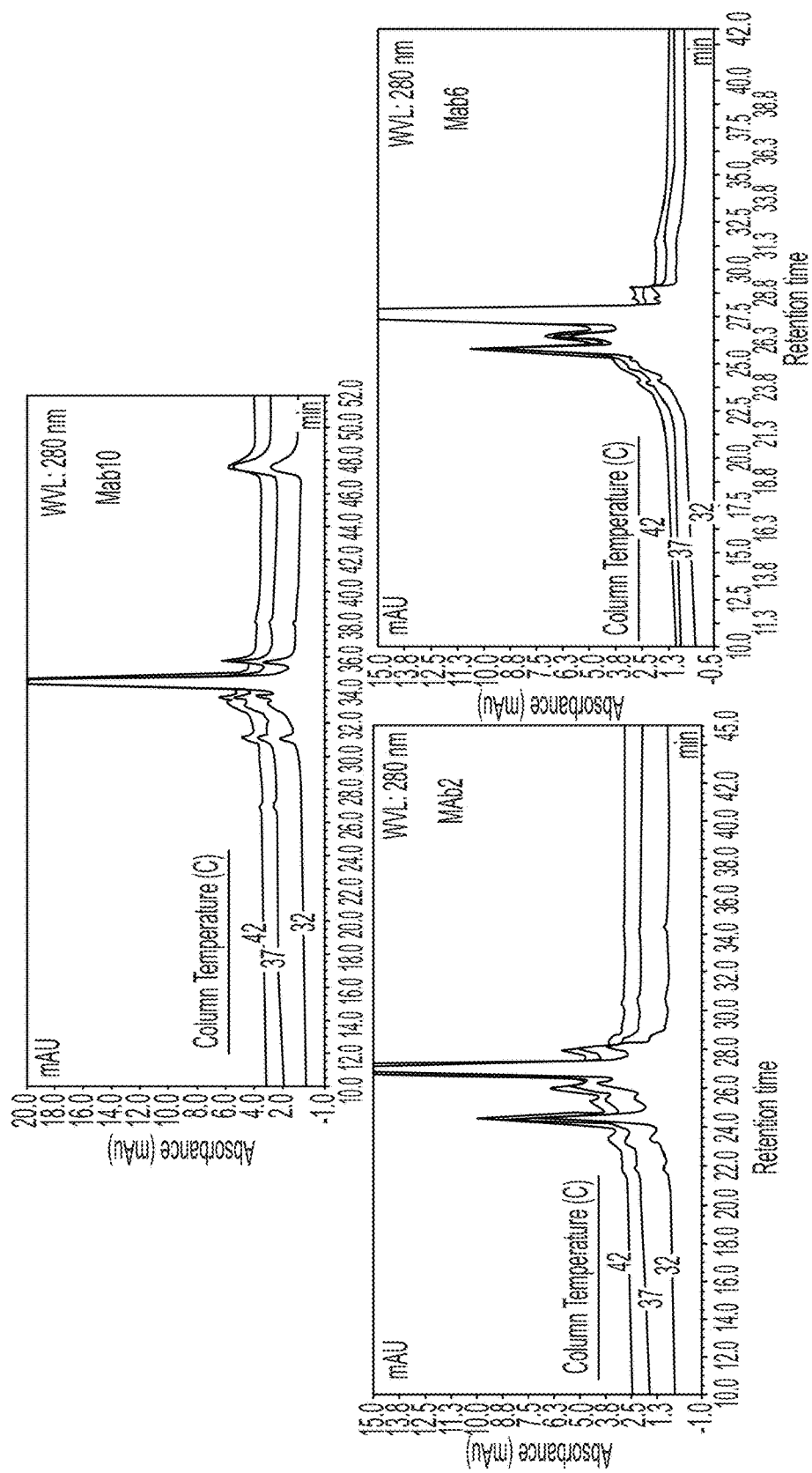
FIG. 14 shows the robustness of an IEC for three mAb's as a function of temperature. The chromatography conditions were the same for all three antibodies and as described for FIG. 13.

As shown in FIG. 14, good resolution between the antibodies and their charge variants were seen at all temperatures tested for each of the antibodies. Nearly identical chromatograms were seen with each temperature for each antibody.

Figure 15:
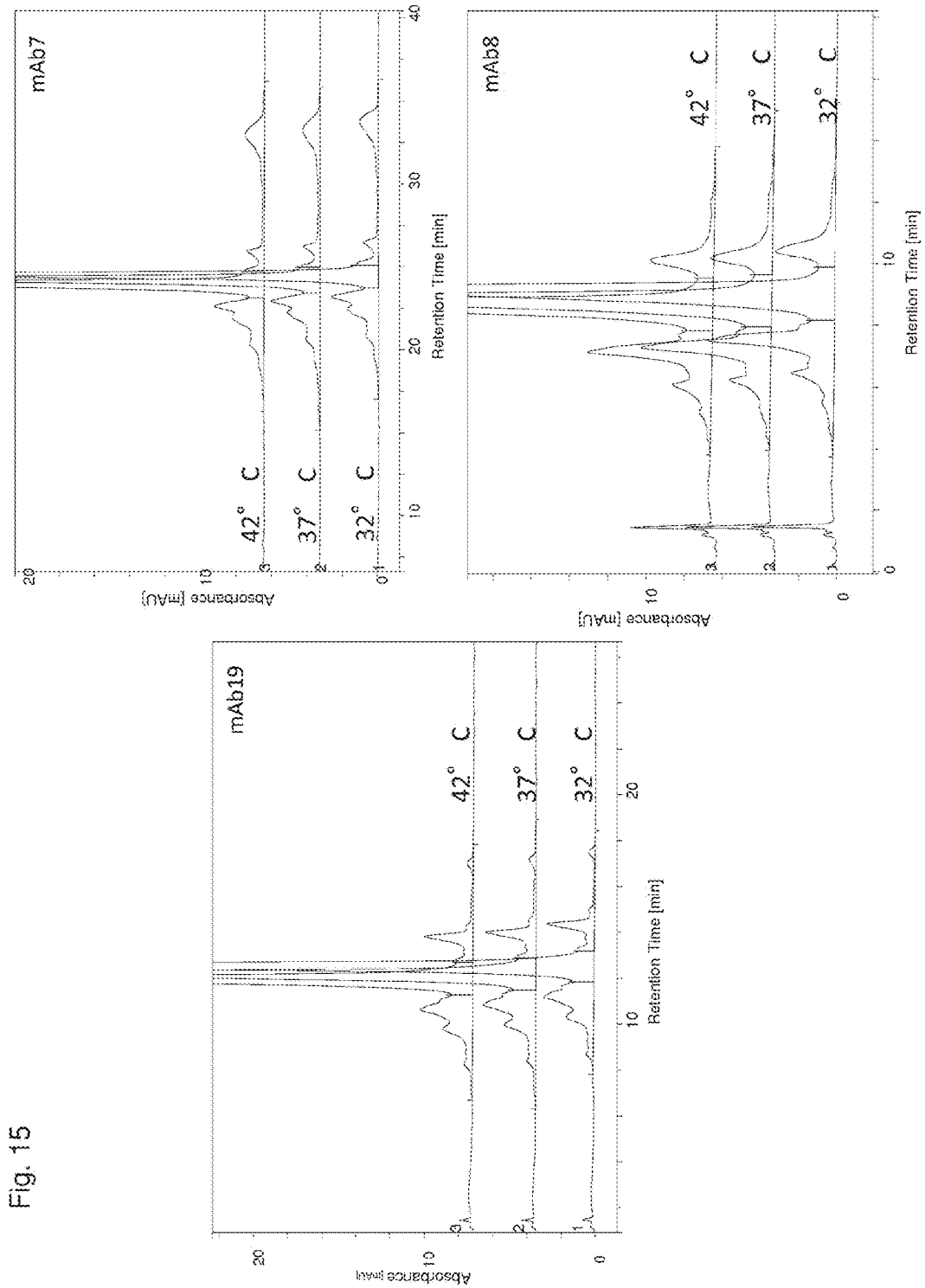
FIG. 15 shows the robustness of an IEC for three mAb's as a function of temperature. The chromatography conditions were the same for all three antibodies. The chromatography conditions are as in FIG. 13 except the buffer was 10 mM HEPES.
Figure 16A:
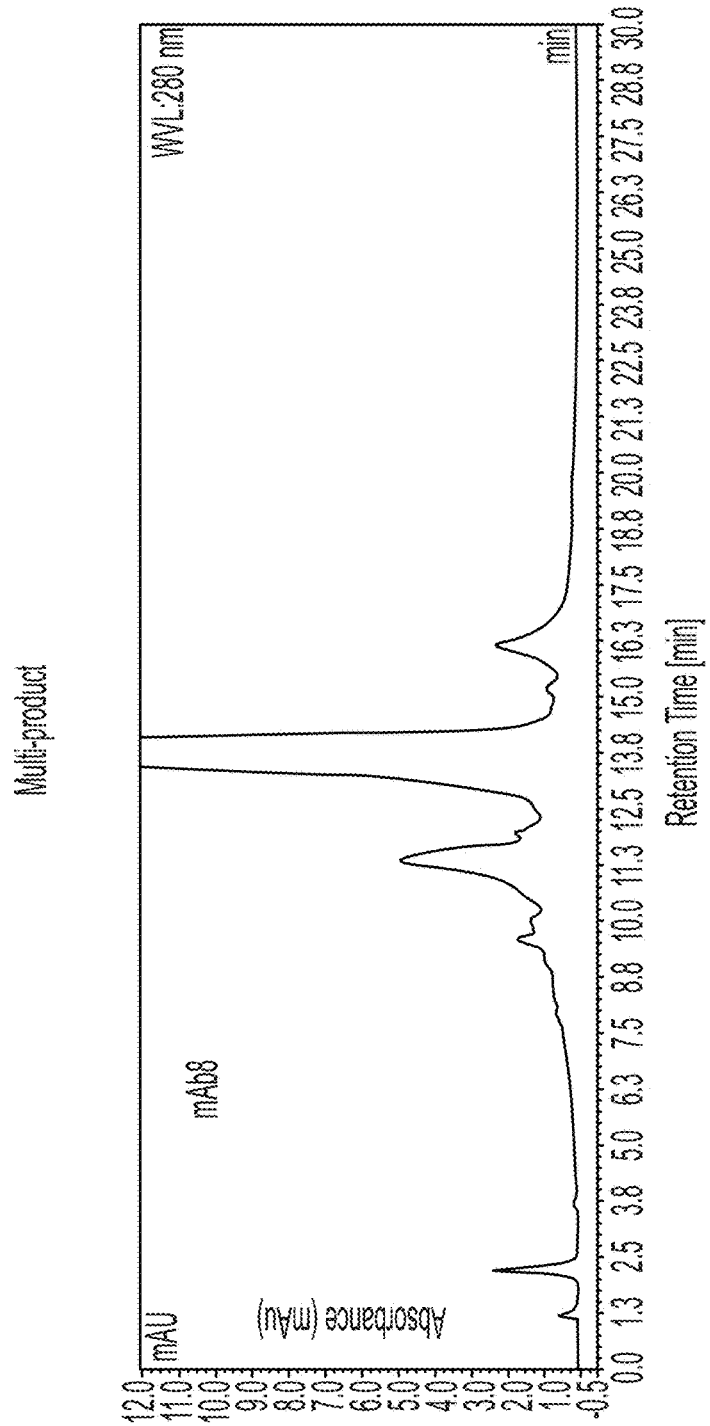
FIG. 16 shows graphs comparing IEX chromatography of three mAbs using the multi-product procedure and using procedures developed for each mAb. The multi-product method was 5 mM ACES pH 7.5 at 37° C. with a gradient from 0 mM NaCl to 75 mM NaCl in 50 minutes (1.5 mM/min) and a flow rate of 0.8 mL/min. The buffer and temperature for the product-specific methods were different. For mAb8, it was 20 mM MES pH 6.5 at 30° C.; for mAb25, it was 20 mM HEPES pH 7.6 at 42° C.; and for mAb26 it was 20 mM ACES pH 7.1 at 40° C. The column was a MabPac SCX-10 column (4×250 mm).
Figure 16B:
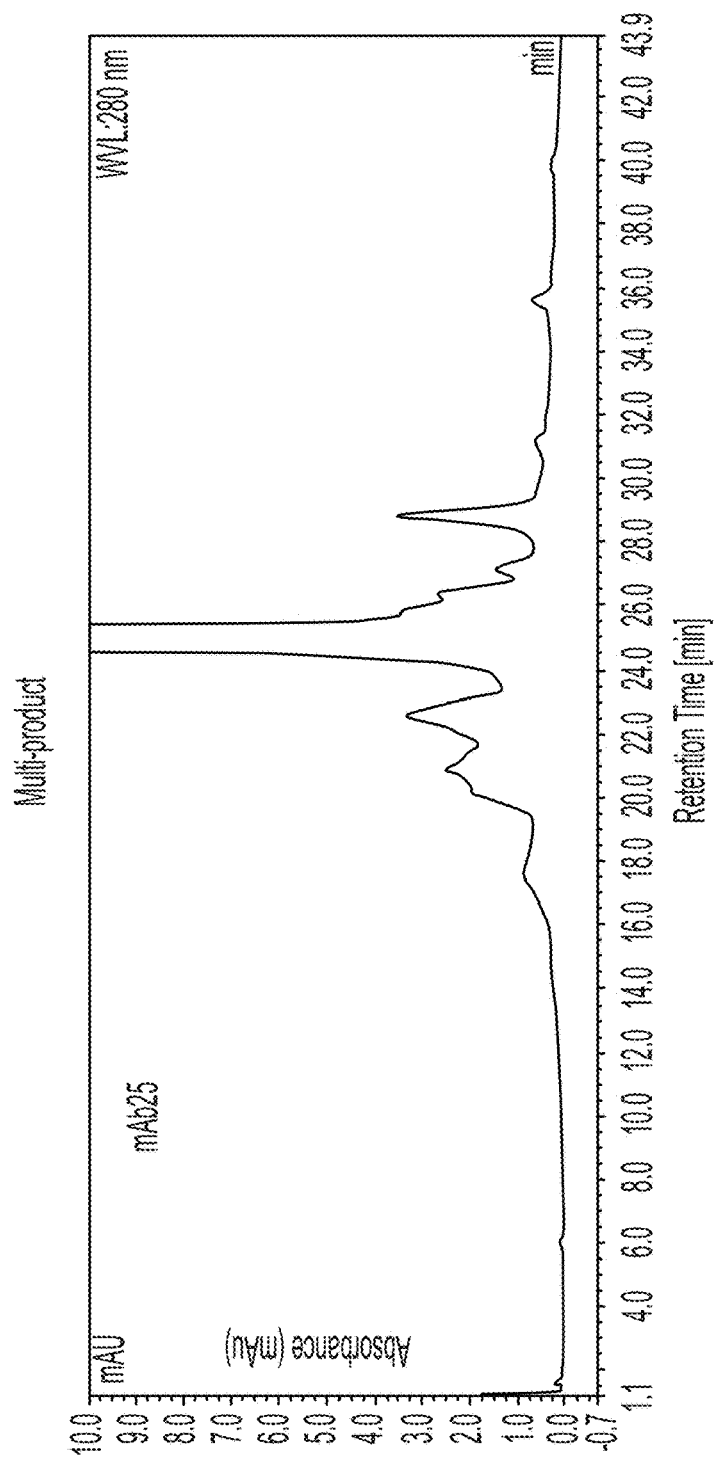
Figure 16C:
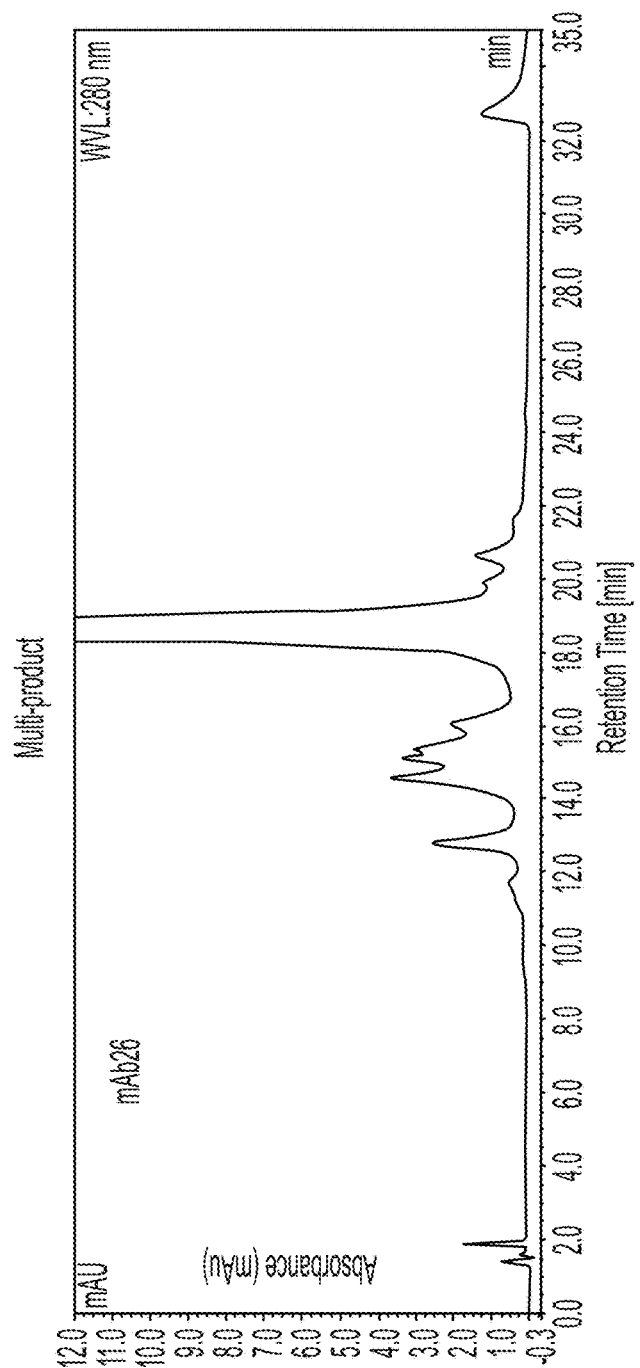
Figure 16D:
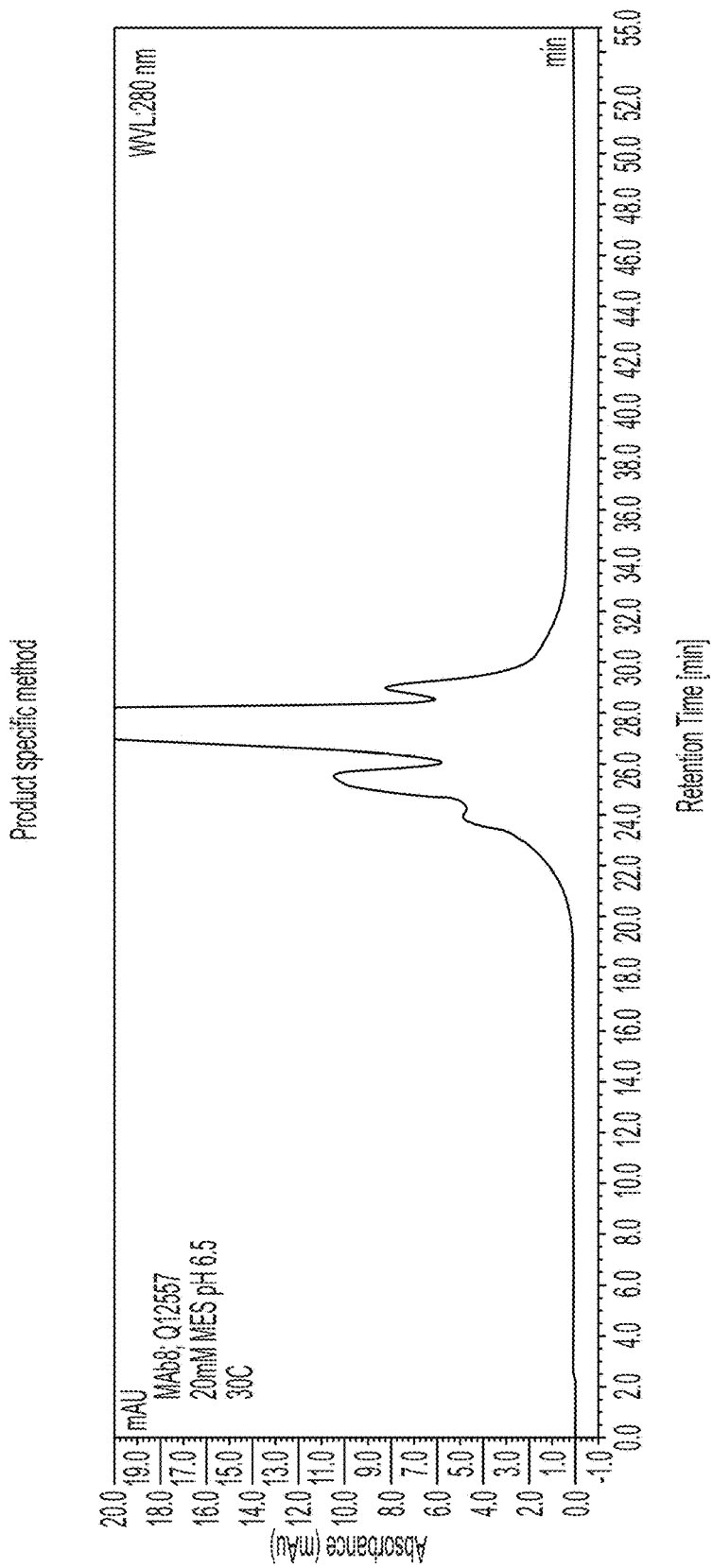
Figure 16E:
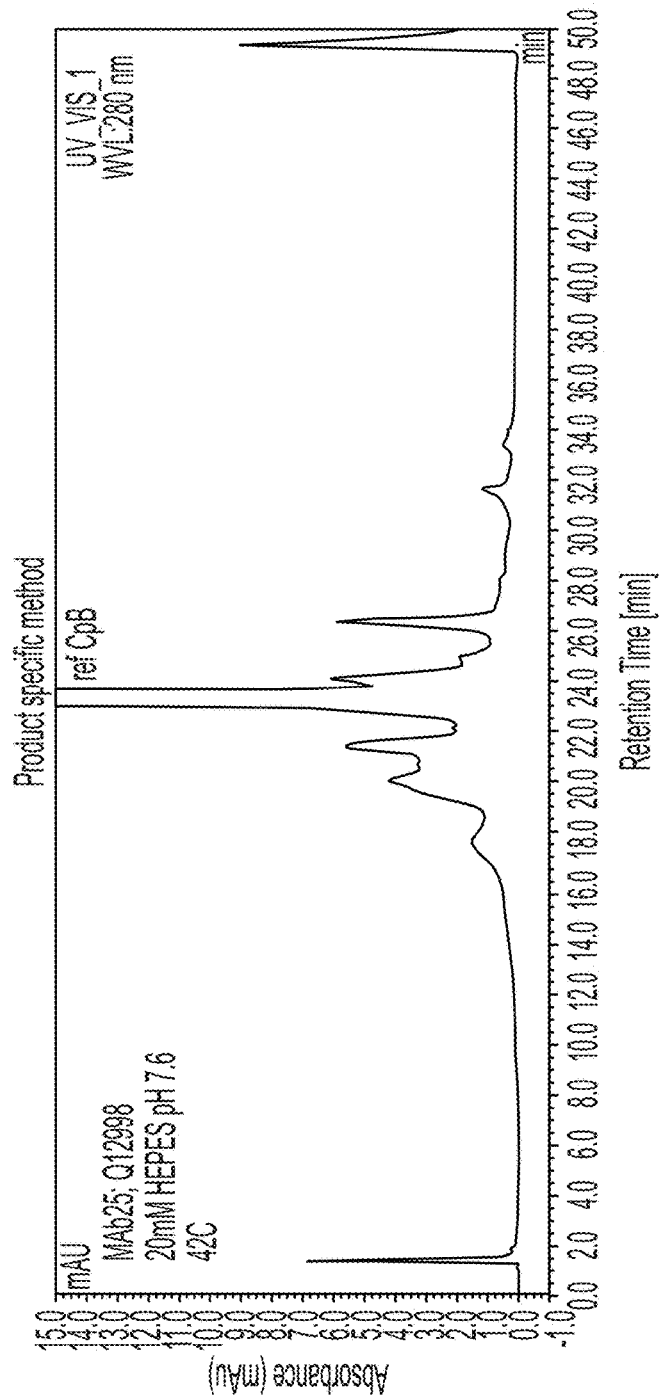
Figure 16F:
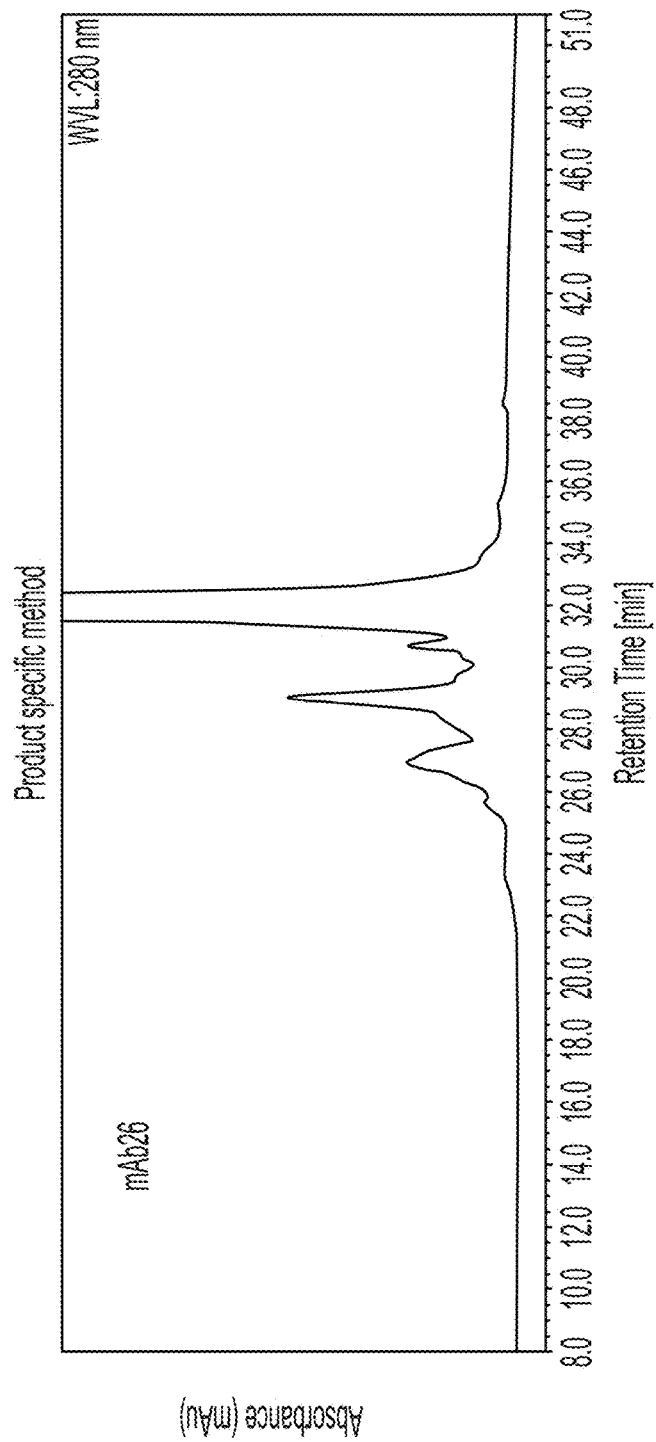

In a second experiment, mAbs 19, 7 and 8 were tested for temperature robustness in 10 mM HEPES buffer. As seen in FIG. 15, good resolution between the antibodies and their charge variants were seen at all temperatures tested for each of the antibodies. Quantification of peak areas revealed no significant changes in analysis with respect to temperature.

TABLE 6

Temperature robustness of multi-product IEC

| mAb | Temp. | % Acidic | % Main Peak | % Basic 1 | Resolution Acidic | Resolution Basic |
|---|---|---|---|---|---|---|
| mAb19 | 42° C. | 16.46 | 75.62 | 7.92 | 1.51 | 3.20 |
|  | 37° C. | 16.69 | 74.65 | 8.56 | 1.53 | 3.26 |
|  | 32° C. | 15.97 | 76.17 | 7.86 | 1.62 | 3.30 |
| mAb7 | 42° C. | 18.95 | 67.30 | 13.75 | 1.31 | na |
|  | 37° C. | 19.80 | 67.28 | 12.92 | 1.36 | na |
|  | 32° C. | 18.53 | 68.80 | 12.66 | 1.45 | na |
| mAb8 | 42° C. | 22.20 | 68.78 | 9.03 | 2.21 | 1.72 |
|  | 37° C. | 22.44 | 67.67 | 9.89 | 2.25 | 1.45 |
|  | 32° C. | 22.60 | 67.25 | 10.15 | 2.33 | 1.35 |

Example 5. Comparison of Multi-Product IEC with Product-Specific IEC

The multi-produce IEC was compared to product-specific IEC methods developed for mAb8, mAb25 and mAb26. IEC of mAb8, mAb28 and mAb26 was performed using the multi-product IEC method described in Example 2 except gradient at 1.5 mM NaCl/min [Genentech-please confirm.] The buffer and temperature for the product specific methods were different. For mAb8, it was 20 mM MES pH 6.5 at 30° C.; for mAb25, it was 20 mM HEPES pH 7.6 at 42° C.; and for mAb26 it was 20 mM ACES pH 7.1 at 40° C. As can be seen in FIG. 16, the multi-product IEC (left panels) performed similarly or with better resolution than the product-specific IEC methods (right panels).

Example 6. Use of Multi-Product IEC with Different Columns

Figure 17:
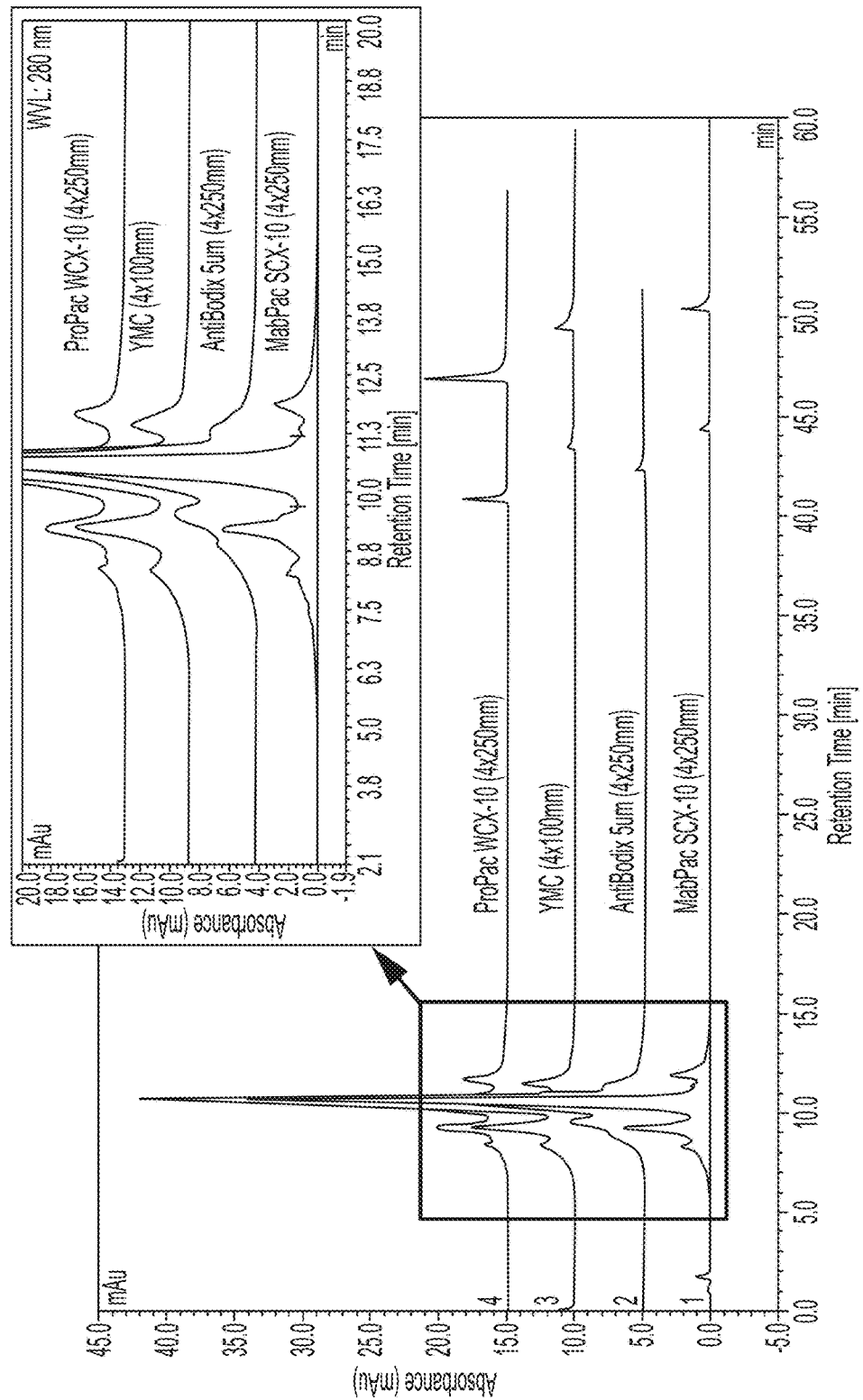
FIG. 17 shows the use of the multi-product chromatography conditions using mAb8 on four different chromatography columns; ProPac WCX-10 (10 μm, 4×250 mm), YMC (5 μm, 4×100 mm), AntiBodix (5 μm, 4×250 mm), and MabPac SCX-10 (10 μm, 4×250 mm). Chromatography conditions were as described for FIG. 13. Insert shows enlargement of variant peaks.

The multi-product IEC was used for chromatography column selection. mAb8 was tested in four different cation exchange columns using the methods described in Example 2 except the gradient was 1.5 mM NaCl/min. The columns tested were ProPac WCX-10, 4×250, 10 μm; YMC, 4.6×100, 5 μm; Antibodix NPS, 4.6×250, 5 μm; and MabPac SCX-10, 4×250, 10 μm (used in Example 2). As can be seen in FIG. 17, all four columns resulted in adequate resolution. Quantification of peak areas and resolutions between the acid peak and basic peak with the main peak are shown in Table 7.

TABLE 7

Column screening for mAb8

| Column | % Acidic | % Main Peak | % Basic 1 | Resolution Acidic | Resolution Basic |
|---|---|---|---|---|---|
| ProPac WCX-10 | 19.80 | 66.98 | 13.22 | 2.06 | 1.42 |
| YMC | 25.21 | 64.86 | 9.93 | 1.78 | 0.93 |
| AntiBodix NP5 | 23.23 | 66.10 | 10.67 | 0.99 | 0.22 |
| MabPac SCX-10 | 14.80 | 73.38 | 11.83 | 2.81 | 2.54 |

Example 7. Scalability

Figure 18:
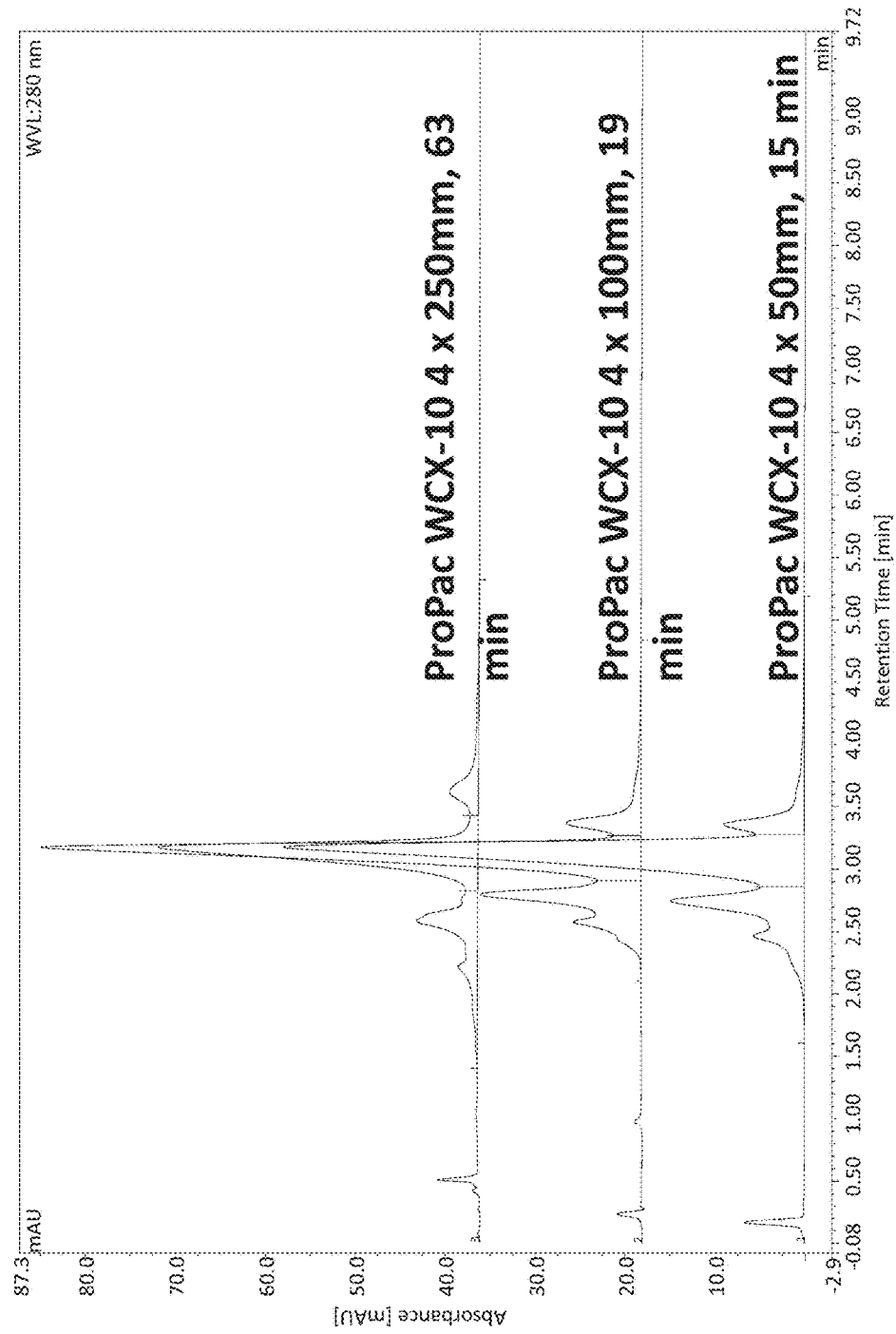
FIG. 18 shows the use of the multiproduct chromatography conditions using mAb8 on ProPac WCX-10 chromatography columns of different sizes; 4×250 mm, 4×100 mm, 4×50 mm. Run times were shorter with shorter columns. Chromatograms are normalized for main peak. Chromatography conditions were as described for FIG. 15 except for the gradient time.

The use of different sized cation exchange chromatography columns were evaluated for use in the multi-product IEC. A reduced column length will result in shorter run times. mAb8 was chromatographed on ProPac WCX-10 columns of three different sizes using the multi-product IEC method described in Example 2. As the columns were different sizes, the chromatography runs were for different periods of time. The columns sizes and respective run times were as follows: 4×250 mm for 63 min, 4×100 mm for 19 min, and 4×50 mm for 15 min. Results are presented in FIG. 18. Although, some resolution is lost with shorter columns, adequate separation with consistent quantitative results is obtained with the shorter column for a high throughput application. Quantification of peak areas is consistent and is shown in Table 8.

tigate assay robustness using a six factor Plackett-Burman Design of Experiment (Tables 9 and 10). The factors examined were the solvent pH, ending salt concentration, Column temperature, Flow rate, injection volume, and buffer molality. The response variables for this study included the relative percentage Main peak, Acidic and Basic variants. A total of 21 runs were performed, 12 at factorial conditions and 9 runs at target.

TABLE 13

Variable Parameters

| Injection # | Pattern | pH | Buffer Molarity (mM) | Injection Volumne (μL) | Temperature (C.°) | Flow Rate (mL/min) | Gradient ending NaCl (mM) |
|---|---|---|---|---|---|---|---|
| 1 | Target | 7.50 | 5.0 | 25 | 40 | 1.50 | 90 |
| 2 | (+---+-) | 7.65 | 4.7 | 22 | 37 | 1.53 | 85 |
| 3 | (+-+++-) | 7.65 | 4.7 | 28 | 43 | 1.53 | 85 |
| 4 | Target | 7.50 | 5.0 | 25 | 40 | 1.50 | 90 |
| 5 | (--+--+) | 7.35 | 4.7 | 28 | 37 | 1.47 | 95 |
| 6 | Target | 7.50 | 5.0 | 25 | 40 | 1.50 | 90 |
| 7 | (+++---) | 7.65 | 5.3 | 28 | 37 | 1.47 | 85 |
| 8 | Target | 7.50 | 5.0 | 25 | 40 | 1.50 | 90 |
| 9 | (-+++--) | 7.35 | 5.3 | 28 | 43 | 1.47 | 85 |
| 10 | (-+--+-) | 7.35 | 5.3 | 22 | 37 | 1.47 | 85 |
| 11 | Target | 7.50 | 5.0 | 25 | 40 | 1.50 | 90 |
| 12 | (-+-+++) | 7.35 | 5.3 | 22 | 43 | 1.53 | 95 |
| 13 | Target | 7.50 | 5.0 | 25 | 40 | 1.50 | 90 |
| 14 | (++---+) | 7.65 | 5.3 | 22 | 37 | 1.47 | 95 |
| 15 | Target | 7.50 | 5.0 | 25 | 40 | 1.50 | 90 |
| 16 | (+--+-+) | 7.65 | 4.7 | 22 | 43 | 1.47 | 95 |
| 17 | Target | 7.50 | 5.0 | 25 | 40 | 1.50 | 90 |
| 18 | (--+-++) | 7.35 | 4.7 | 28 | 37 | 1.53 | 95 |
| 19 | (---+--) | 7.35 | 4.7 | 22 | 43 | 1.47 | 85 |
| 20 | Target | 7.50 | 5.0 | 25 | 40 | 1.50 | 90 |
| 21 | (++++++) | 7.65 | 5.3 | 28 | 43 | 1.53 | 95 |

TABLE 8

Scalability of multi-product IEC

| Column Size | Run Time | % Acidic | % Main Peak | % Basic 1 | Resolution Acidic | Resolution Basic |
|---|---|---|---|---|---|---|
| 4 × 250 | 63 min | 22.44 | 67.67 | 9.89 | 2.25 | 1.45 |
| 4 × 100 | 19 min | 24.72 | 65.85 | 9.42 | 1.66 | 0.85 |
| 4 × 50 | 15 min | 23.22 | 67.03 | 9.75 | 1.51 | 0.65 |

Example 8. Robustness of Assay

Validation of a test procedure requires the method to be suitably robust. A design-of-experiments (DoE) approach to evaluate robustness comprehensively assesses the effects of minor variations in the assay conditions, including interactive effects. The specific multivariate conditions of each experiment were selected to combine factors with the potential for interaction. Factors that could not be varied continuously but are known to have effects, i.e., columns (e.g., lot to lot variability, age) and instruments (e.g., two model types) were examined with one-factor-at-a-time methods. The effects were determined by comparing the response variability at target conditions to the variability of responses at conditions varied according to the factorial design.

Experimental Design

The following describes the Ion Exchange conditions used for monitoring charge heterogeneity of recombinant monoclonal antibody proteins for the Platform Method Control approach. The objective of this study was to inves-

TABLE 10

Results

| Pattern | % Acidic | % Main | % Basic |
|---|---|---|---|
| Target | 16.72 | 58.38 | 24.89 |
| (+---+-) | 16.37 | 57.79 | 25.84 |
| (+-+++-) | 16.44 | 57.84 | 25.72 |
| Target | 16.54 | 58.34 | 25.12 |
| (--+--+) | 16.22 | 59.20 | 24.58 |
| Target | 16.58 | 58.44 | 24.98 |
| (+++---) | 16.60 | 58.58 | 24.81 |
| Target | 16.57 | 58.86 | 24.57 |
| (-+++--) | 16.29 | 59.37 | 24.33 |
| (-+--+-) | 16.12 | 59.36 | 24.52 |
| Target | 16.34 | 58.45 | 25.20 |
| (-+-+++) | 15.97 | 58.82 | 25.21 |
| Target | 16.70 | 58.16 | 25.14 |
| (++---+) | 16.62 | 57.94 | 25.44 |
| Target | 16.63 | 58.79 | 24.58 |
| (+--+-+) | 16.34 | 58.71 | 24.95 |
| Target | 16.54 | 59.05 | 24.41 |
| (--+-++) | 16.29 | 59.47 | 24.24 |
| (---+--) | 16.21 | 59.32 | 24.48 |
| Target | 16.46 | 58.32 | 25.22 |
| (++++++) | 16.40 | 58.64 | 24.96 |

TABLE 11

Robustness Summary Table

| Studies | Conditions | Results |
|---|---|---|
| Multivariate parameters: Solvents A & B pH, Buffer Molality (mM), Column Temp. (° C.), Flow Rate (mL/min.), Injection Volume (µL), Salt Conc. (mM) | Multivariate design to evaluate Solvents A&B pH of 7.5 ± 0.15 Buffer Molality 5 ± 0.3 mM Column Temp. 40° ± 3° C. Flow Rate 1.50 ± 0.03 mL/min Injection Volume 25 ± 3 µg Salt Conc. 90 ± 3 mM | No significant effect. 1.2%, 0.9% and 1.8% RSD values across all IEC parameters for percent peak areas of main peak, acidic and basic regions, respectively. |
| Instrument-to-Instrument and Column lot Variability | 2 instruments (1 HPLC & 1 UPLC), 2 columns of different resin lots, single analyst | No significant effect. 0.9%, 1.0% and 2.3% RSD values from two instruments and five cartridges for percent peak areas of main peak, acidic and basic regions, respectively. |

Statistical Analysis

The sample of target response values exhibits the variability that occurs when all variable factors are at target conditions. The sample of factorial response values exhibits the variability that occurs when multiple factors are varied in combination.

TABLE 12

| | Target Conditions; (n = 9) | | | Factorial Conditions; (n = 11) | | |
|---|---|---|---|---|---|---|
| | % Acidic | % Main peak | % Basic | % Acidic | % Main peak | % Basic |
| Average | 16.5 | 58.5 | 24.9 | 16.3 | 58.6 | 24.8 |
| SD | 0.1 | 0.3 | 0.3 | 0.2 | 0.6 | 0.5 |
| % RSD | 0.70% | 0.50% | 1.23% | 1.13% | 1.06% | 2.16% |

Figure 19:
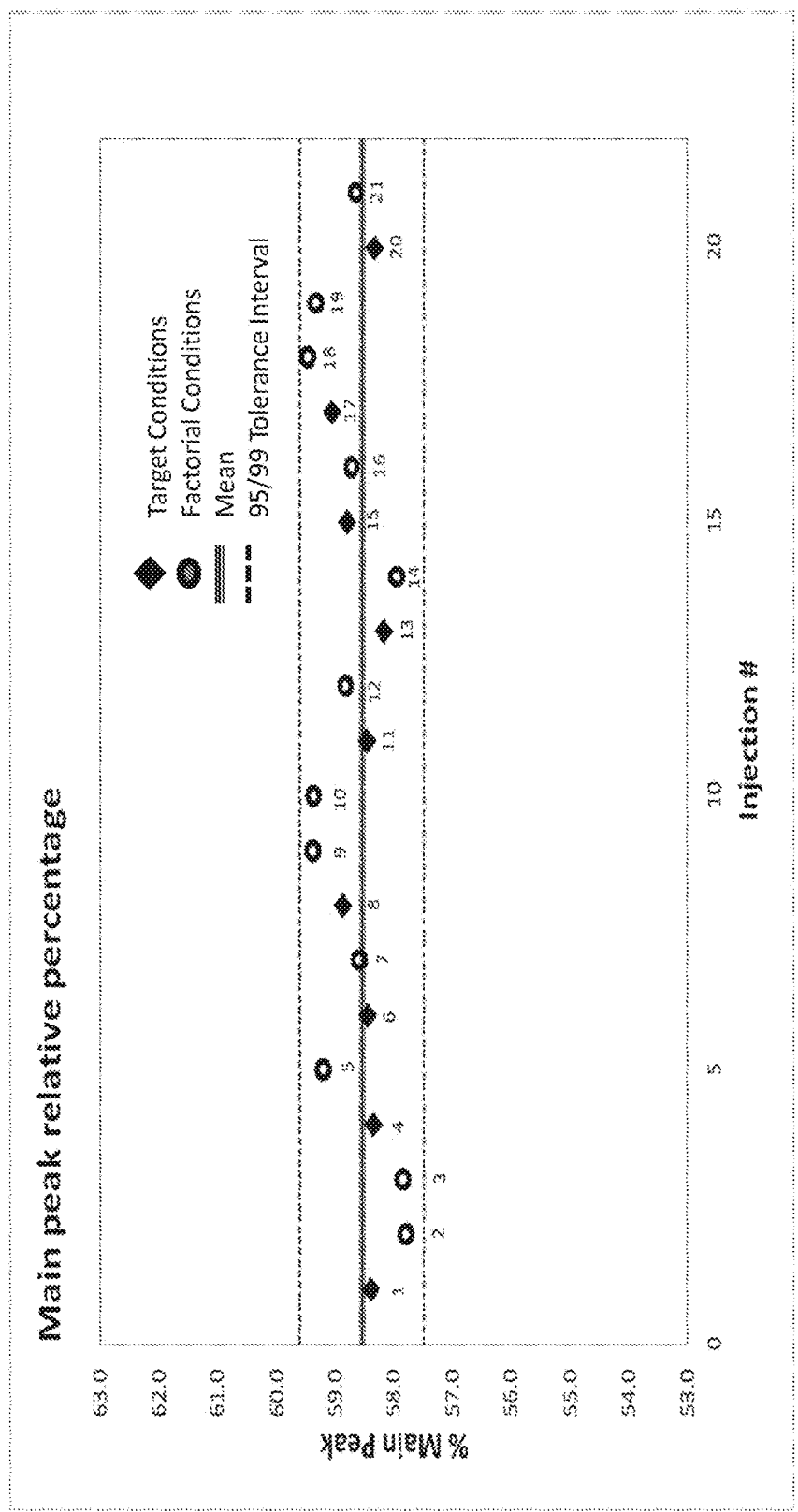
FIG. 19 shows a graph of the main peak relative percentage of a GMP Robustnest DOE study.
Figure 20:
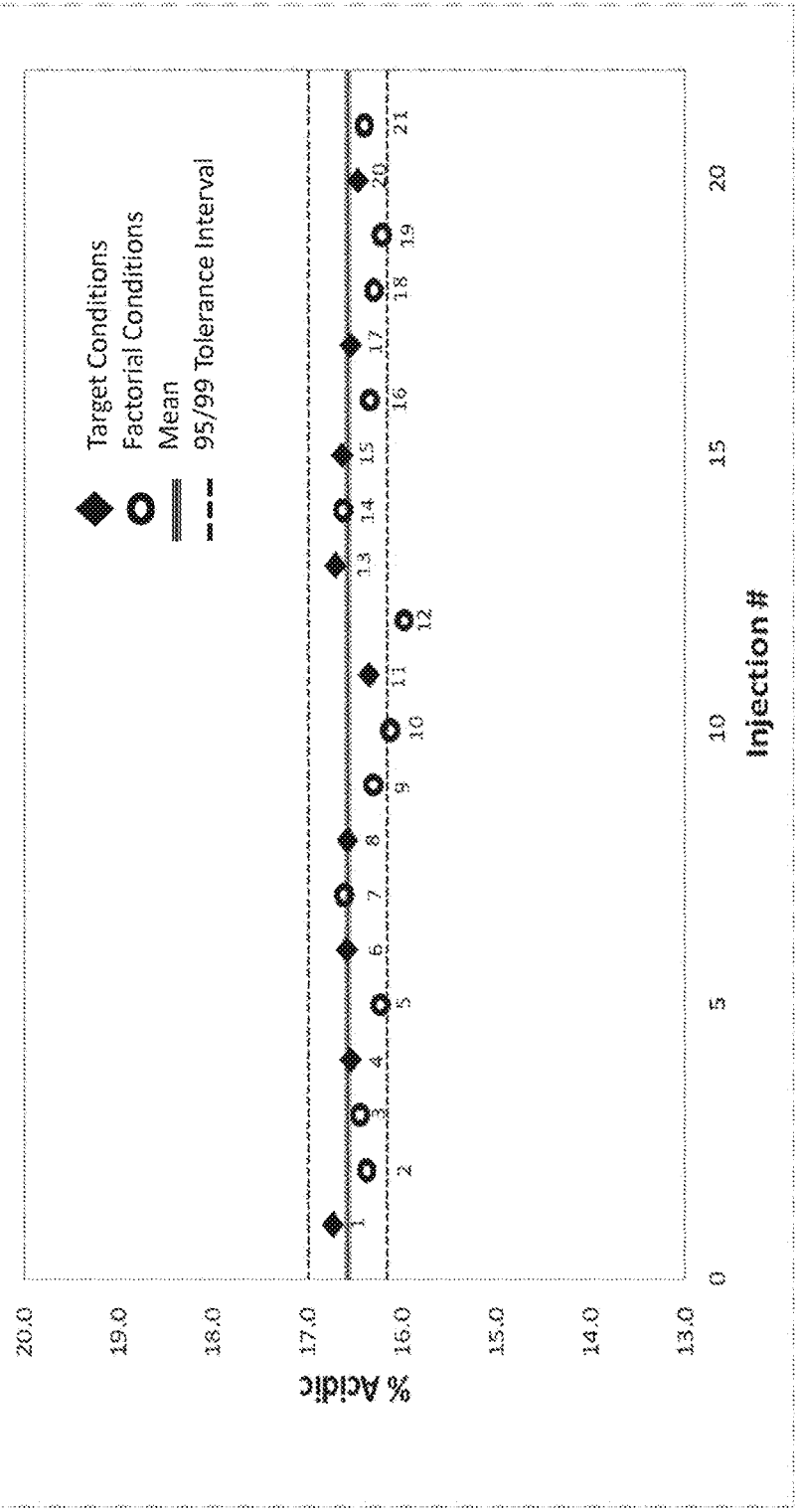
FIG. 20 shows a graph of the main peak relative percentage of a GMP Robustnest DOE study.
Figure 21:
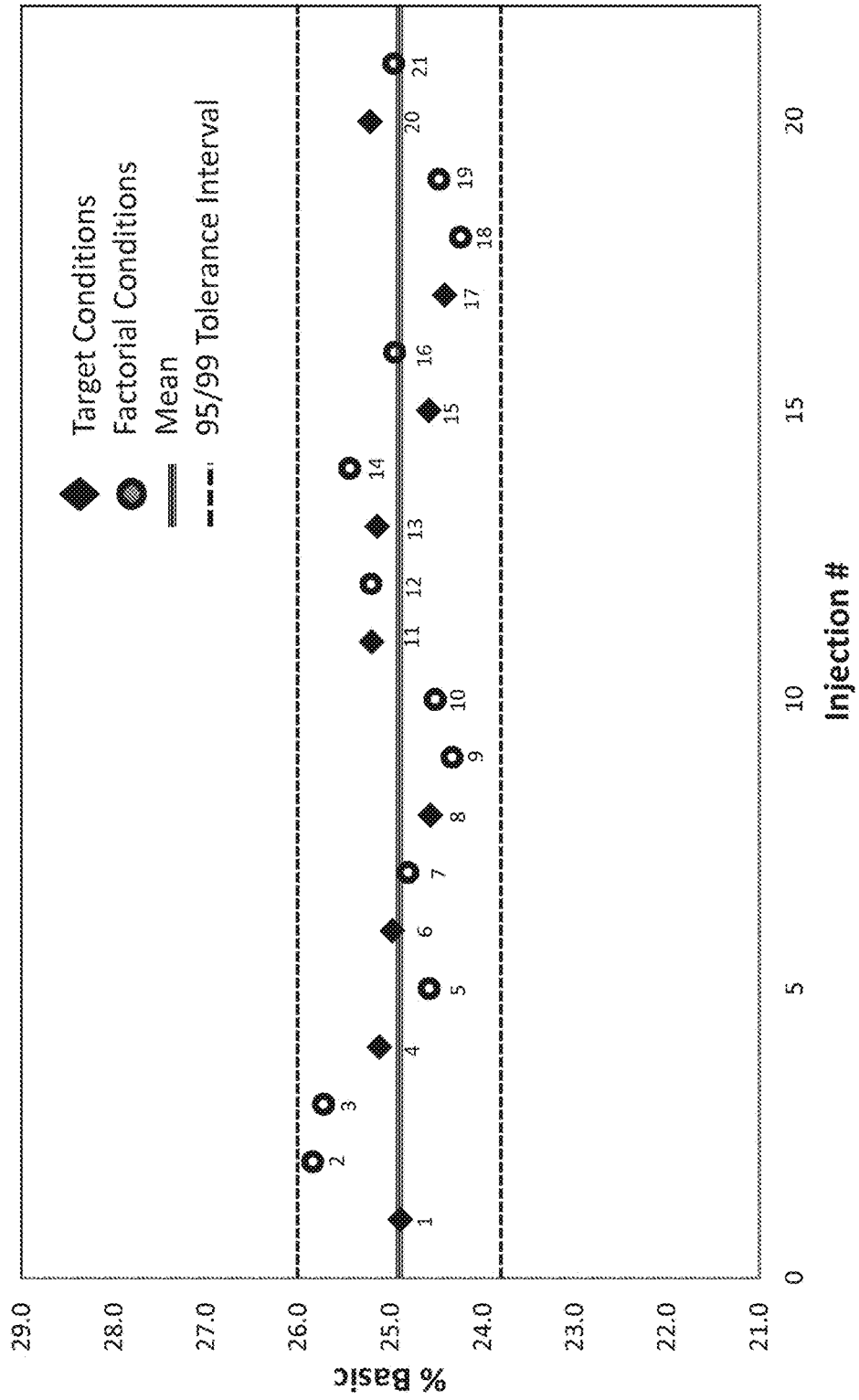
FIG. 21 shows a graph of the main peak relative percentage of a GMP Robustnest DOE study.

Mean, standard deviation (SD) and relative standard deviation (RSD) were calculated for all target and DoE factorial response values. Although minor differences are seen between the target conditions and factorial conditions isoform's SDs and RSDs they are unprecedentedly low. Results are shown in FIGS. 19-21.

Typically for an IEC validation the acceptable % RSD limits are: <5% for the Main Peak, <10% for the Acidic and Basic variants.

All of the factorial conditions produce results for the % Main Peak and % Basic which are within the 95/99 Tolerance Interval calculated from the target conditions results.

Two factorial conditions #10 (−+−−+−) and #12 (−+−+++) produced % Acidic variant values below the low 95/99 TI requirement calculated from the target conditions results. All others factorial conditions produced values within the interval.

The conditions which produced values outside of the target conditions 95/99 TI are a consequence of the high level of precision in the assay and limited uncontrolled variability (instruments & column) within the DoE study.

A normal 95/99 TI for IEC can be in a 3-5% range for Main peak, Acidic and Basic variants.

Materials and Methods

To quantitate charged variants of protein or antibody drug substance, drug product or toxicology material for clinical products using the Platform Method Control (PMC) approach. The Platform Method Control approach utilizes a representative antibody as Method Control for determination of system suitability in this multi-product cation exchange chromatography method. This multi-product test procedure is applicable to protein molecules with a positive net charge (at approximate pI>7.2).

Equipment and Material 1.1 HPLC system: Waters UPLC H-Class Bio with Tunable UV (TUV); Waters Alliance 2695 with Waters 2487 detector, and Waters Alliance e2695 with Waters 2489 UV/Vis detector or equivalent.

1.2 In-line UV detector capable of monitoring at 280 nm.

1.3 HPLC must contain a column compartment capable of maintaining temperature at the set point ±2° C.

1.4 Electronic integrator or computer system capable of peak area integration.

1.5 Autosampler capable of cooling to 2-8° C.

1.6 Column: ThermoFisher MabPacR SCX-10, 10 µm, 4 250 mm (Thermo, product no. 074625).

1.7 pH meter with temperature compensation.

1.8 Water bath capable of heating at 37±2° C.

1.9 Calibrated thermometers with 1° C. divisions and specified for use with partial immersion into water baths.

Reagents

NOTE: Recipes are for nominal quantities of reagent and can be adjusted proportionally according to assay requirements.

2.1 Purified water, suitable for HPLC analysis (Super-Q or equivalent)

2.2 Solvent A: 5 mM HEPES Buffer, pH 7.5±0.1
  HEPES Free Acid, reagent grade (FW 238.3, Corning CellGro; Product No. 61-034-R0), 1.87 g
  HEPES Sodium Salt, reagent grade (FW 260.3, SigmaAldrich; Product No. H3784), 1.87 g
  Purified water QS to 3 L
  Combine the listed chemicals in a graduated cylinder with approximately 2900 mL of purified water. Stir until dissolved. QS to 3 L with purified water and measure the pH. Verify the pH is 7.5±0.1 at ambient temperature. If pH is outside the specified range, discard and repeat preparation. Filter through a 0.2-µm membrane.

2.3 Solvent B: 100 mM Sodium Chloride in Solvent A
  Sodium Chloride (FW 58.44 J. T. Baker Cat. no. 3624-01 or equivalent), 5.844 g
  Solvent A (Step 2.2) qs to 1 L
  Combine sodium chloride in a graduated cylinder with approximately 450 mL of Solvent A and stir until dissolved. QS to 1 L with Solvent A and filter through a 0.2-m membrane.

2.4 Solvent C: 1M Sodium Chloride in Solvent A
  Sodium Chloride (FW 58.44 J. T. Baker Cat. no. 3624-01),29.22 g Solvent A (Step 2.2) qs to 500 mL Combine sodium chloride in a graduated cylinder with approximately 450 mL of Solvent A and stir until dissolved. QS to 500 mL with Solvent A and filter through a 0.2-m membrane.

2.5 Column Storage Solution: 0.05% Sodium Azide in Solvent B, pH 7.5±0.1 CAUTION: Sodium azide is highly toxic and mutagenic. Avoid breathing dust and avoid contact with skin (it is readily absorbed through skin).

Sodium Azide (FW 65.01, EM Science 0066884R or equivalent), 2.25 g; Solvent B (Step 2.2), qs to 500 mL Combine the sodium azide in graduated cylinder with approximately in 450 mL of Solvent B and stir until dissolved. Qs the solution to 500 mL with Solvent B and filter through a 0.22-m membrane.

2.6 Column and system cleaning solution: 0.1N Sodium Hydroxide (JT Baker 5636-02), prepare per the steps below:
1N NaOH 100 µL
Purified water 900 µL
Combine the listed chemicals and mix well.

2.7 Sample and Reference Standard formulation buffer
2.8 10% Polysorbate 20 Stock (w/v)
Polysorbate 20 (Polysorbate™ 20, Sigma Cat. P7949 or equivalent) 10 g, Purified water, qs to 100 mL
Weigh the Polysorbate 20 directly into a tared graduate cylinder. Avoid contact with the neck of the cylinder with surfactant. Carefully qs to 100 mL with purified water, avoiding formation of bubbles. Gently lower a magnetic stir bar into the cylinder. Stir the solution for 15-20 minutes until all the surfactant is dissolved.

2.9 Method Control formulation buffer
MAb8 Formulation Buffer: 20 mM Histidine HCl, 120 mM Sucrose, 0.02% Polysorbate 20, pH 6.0±0.3
L-Histidine HCl, monohydrate (FW 209.6) 2.31 g
L-Histidine, free base (FW 155.2) 1.40 g
Sucrose (FW 342.3) 41.08 g
Polysorbate 20 0.20 g
or 10% Polysorbate 20 (w/v) stock solution 2.0 mL
Purified Water qs to 1.0 L
Combine the listed chemicals with approximately 800 mL of purified water and stir until dissolved. Verify the pH is 6.0±0.3. If pH is outside the specified range, discard and repeat preparation. Qs the solution to 1.0 L with purified water. Filter through a ? 0.45-?m membrane.

2.10 5 mg/mL Carboxypeptidase B, DFP treated (Roche 103233) or equivalent, approximate activity of 150 U/mg
2.11 1 mg/mL CpB
5 mg/mL Carboxypeptidase B, DFP treated 20 µL
Purified water 80 µL
Accurately add the 5 mg/mL Carboxypeptidase B into the purified water. For concentrations of purchased Carboxypeptidase B other than 5 mg/mL, adjustments to the volumes may be made to ensure a final concentration of 1 mg/mL. Prepare fresh.

Method Control, Sample, Reference and Formulation Buffer Blank Preparation 3.1 Method Control (MAb8), Nominal concentration: 50 mg/mL
Dilute the Method Control with Solvent A (Step 2.2) to a final concentration of approximately 2.0 mg/mL (e.g., for 50 mg/mL Method Control, combine 40 µL sample and 960 µL of Solvent A).

3.2 Method control blank
Dilute the Method Control Formulation Buffer with Solvent A using the same dilution scheme as in Step 3.1.

3.3 Sample and reference standard preparation
Dilute sample(s) and reference standard to 2 mg/mL with Solvent A.

3.4 Sample and reference standard blank preparation
3.4.1 Dilute formulation buffer for the product using the same dilution scheme as Step 3.4.

3.5 Record dilutions on data sheet.

3.6 Sample Preparation with CpB Digestion Refer to Product Specific Information and Instructions for CpB digestion requirements
3.6.1 Make a 1% (w/w) addition of 1 mg/mL CpB (step 2.12) to the diluted method control, sample(s), reference standard and formulation buffer blanks (e.g., add 20 L of 1 mg/mL CpB to 1000 L of 2.0 mg/mL sample).
3.6.2 Vortex gently and incubate the CpB treated method control, sample(s), reference standard and formulation buffer blanks for 20±2 minutes at 37±2?C.
3.6.3 Record preparations on data sheet.

3.7 Transfer the diluted Method Control, Reference Standard, sample(s) and formulation buffer blanks into appropriate vials for analysis.

3.8 HPLC analysis should be completed within 48 hours of sample preparation. Sample(s) should be stored at 2-8° C. prior to analyses.

Chromatographic Conditions 4.1 Chromatographic conditions common to both Waters' HPLCs instruments:
4.1.1 Flow rate: 1.5 mL/min
4.1.2 Autosampler temperature: 5±3° C.
4.1.3 Column temperature: 40±2° C.
4.1.4 UV detection wavelength: 280 nm
4.1.5 Injection volume: 25 L (~50 g)

4.2 Instrument setting for Water's Aqcuity H-class UPLC and multiple wavelength or diode array detectors
4.2.1 Zero off set analog output: 5%
4.2.2 Attenuation analog output: 500 mAU
4.2.3 Washes settings: Injection with needle wash (10% IPA)
Pre-Inject 10 s
Post-Inject 20 s
4.2.4 Draw and dispense speed: 100 µL/min
4.2.5 Acceleration 2.0 mL/min/0.02 min (100 mL/min/min)
4.2.6 Detector settings
4.2.6.1 Sampling Rate: 1 pt/sec
4.2.6.2 Filter: Hamming
4.2.6.3 Time Constant 1.0
4.2.6.4 Ratio Minimum Minimum Ratio 0.00 Maximum Ratio 2.00
4.2.6.5 Auto Zero Channel A: (Time 0 and Time 50)
4.2.6.6 Sensitivity: 2.000 AUFS 4.3 Instrument setting for Waters Alliance (e)2695 HPLC with Waters 2487 Detector
4.3.1 Stroke volume: 100 µL
4.3.2 Needle Wash Time: Extended (10% IPA)
4.3.3 Solvent degassing: set "on" mode
4.3.4 Acceleration 10.0 mL/min/0.1 min (100 mL/min/min)
4.3.5 Draw and dispense speed: Slow (50 µL/min)
4.3.6 Detector settings
4.3.6.1 Sampling Rate: 1 pt/sec
4.3.6.2 Filter: Hamming
4.3.6.3 Time Constant 1.0
4.3.6.4 Ratio Minimum 0.1000
4.3.6.5 Auto Zero Channel A at Time 0 and Time 50
4.3.6.6 Sensitivity: 2.000 AU 4.4 Gradient:

TABLE 13

| Time (min) | % A | % B | % C | Flow Rate (mL/min) |
|---|---|---|---|---|
| 0.0 | 100 | 0.0 | 0.0 | 1.5 |
| 3.0 | 100 | 0.0 | 0.0 | 1.5 |
| 37.0 | 10.0 | 90.0 | 0.0 | 1.5 |
| 37.1 | 0.0 | 0.0 | 100 | 1.5 |
| 40.0 | 0.0 | 0.0 | 100 | 1.5 |
| 40.1 | 100 | 0.0 | 0.0 | 1.5 |
| 50.0 | 100 | 0.0 | 0.0 | 1.5 |

Instrument Conditioning 5.1 Follow the appropriate protocol for use of HPLC 5.2 Prime lines with ~20 mL of appropriate solvent, including the needle wash line with 10% IPA Column Cleaning and Conditioning 6.1 Perform system and column wash by using the following isocratic program. Inject 100 µL of 0.1N NaOH.

TABLE 14

| Time (min) | Flow (mL/min) | % Solvent B | % Solvent B |
|---|---|---|---|
| 0 | 1.5 | 50 | 50 |
| 3 | 1.5 | 50 | 50 |

6.2 Repeat step 6.1, at least five (5) times.

6.3 Using the isocratic program in step 6.1, make a single injection of 100 uL of Solvent A.

6.4 Equilibrate column at initial conditions of the gradient program in step 4.4 (100% Solvent A at 1.5 mL/min) for ~20 minutes or until a stable baseline is observed.

Injection Protocol 7.1 Conditioning: Inject Method Control without CpB digestion until consistent chromatograms are observed for a minimum of 2 injections. The resolution of the acidic region, main peak and basic region must be consistent by visual inspection to the typical chromatograms.

7.2 Platform Method Control without CpB digestion (single injection)

7.3 Formulation buffer blank for Method Control 7.4 Reference Standard* (single injection)

7.5 Sample(s)* (duplicate injection)

7.6 Reference Standard* (single injection)

7.7 Formulation buffer blank(s) for Reference Standard(s)* (single injection)

7.8 Platform Method Control without CpB digestion (single injection)

*With or without CpB if product warranted.

NOTES: 1) If formulation buffers differ for Reference Standard and sample, inject separate blanks for Reference Standard and the sample.

2) If more than 15 injections (including Reference Standards and respective product formulation buffer blanks) in between the Method Control are needed, bracket every 15 injections with Method Control injections. On the system suitability section of the test data sheet, report only the Method Control injections that bracket the sample(s) being reported.

3) Reference Standard is considered a sample and is not used to assess system suitability of the test session.

Column Shutdown and Storage

Store the column by flushing the column with at least 30 mL of Column Storage, Solution (Step 2.4).

System Suitability

NOTE: For the Method Control, determine the integration endpoints by overlaying the Method Control profiles with the Method Control formulation buffer blank. Expand the overlaid profiles and identify the endpoints of the integration by comparing the blank to the Method Control profiles.

9.1 Integrate all peaks attributed to protein. Do not include any peaks that are present in the Method Control formulation buffer blank chromatograms, unless the corresponding peak in the blank is <1% of the peak in PMC.

9.2 Visually confirm consistency of the chromatogram profiles of the bracketing Method Control injections with each other and with the typical chromatographic profiles. All named peaks in the typical chromatograms must be present.

NOTE: Profiles of the named peaks may differ slightly in peak shape from the example profiles due to column and instrument variability.

9.3 Calculate the percent main peak, acidic region and basic region for each bracketing Method Control injection.

9.4 System suitability Range

TABLE 15

| | Acceptable system suitability ranges for the Non CpB treated Method Control | | |
|---|---|---|---|
| | Acidic Region | Main Peak | Basic Region |
| Acceptable range of % Peak Area | 15.5 and 17.7 | 55.5 and 61.4 | 21.3 and 28.6 |

9.5 Record results in the system suitability data sheet.

Data Analysis 10.1 Visually compare the profiles to identify the peaks in both sample and Reference Standard chromatograms.

10.2 Integrate all peaks attributed to protein. Do not include any peaks that are present in the product formulation buffer blank chromatograms, unless the corresponding peak in the blank is <1% of the peak in PMC.

NOTE: To determine the integration endpoints, overlay the sample(s) and Reference Standard profiles with the product formulation buffer blank. Expand the overlaid profiles and identify the endpoints of the integration by comparing the product formulation buffer blank to the sample(s) and Reference Standard profiles.

10.3 Analyze each sample(s) and Reference Standard injection to calculate the percent peak area of the main peak, acidic region and basic region.

What is claimed is:

1. A method for identifying an optimal ion exchange chromatography separation condition to analyze a plurality of compositions, wherein each composition comprises a polypeptide with one or more contaminants, the method comprising
    a) plotting a net charge versus pH curve at a selected temperature for each polypeptide based on an amino acid composition of the polypeptides of two or more of the compositions, and
    b) determining an inflection point of the net charge versus pH curve at or near neutral pH by determining a second derivative of the curves of step a);
    wherein the optimal ion exchange chromatography separation condition is a pH at about a common inflection point for the polypeptides of two or more of the compositions.

2. The method of claim 1, wherein if the net charge at the inflection point is positive, a cation exchange material is used for an ion exchange chromatography.

3. The method of claim 2, wherein the cation exchange chromatography material is a sulfonated chromatography material or a carboxylated chromatography material.

4. The method of claim 1, wherein if the net charge at the inflection point is negative, an anion exchange material is used for a chromatography.

5. The method of claim 4, wherein the anion exchange chromatography material is a quaternary amine chromatography material or a tertiary amine chromatography material.

6. The method of claim 1, wherein a mixed mode chromatography material is used for a chromatography.

7. The method of claim 6, wherein the mixed mode ion exchange material is an ion exchange material comprising a mixture of sequentially packed sulfonated chromatography material or carboxylated chromatography material and a quaternary amine chromatography material or tertiary amine chromatography material.

8. The method of claim 1, further comprising
  c) determining a change in the inflection point pH of the net charge versus pH curve with a change in the temperature (dIP/dT) for the polypeptides of two or more of the compositions,
  d) selecting a buffer for use in the chromatography, wherein a change in an acid dissociation constant of the buffer with change in temperature (dpKa/dT) is essentially the same as the dIP/dT of the polypeptides.

9. The method of claim 8, wherein the buffer provides an effective buffer capacity at an inflection point pH.

10. The method of claim 8, wherein the dIP/dT of the polypeptides of one or more of the compositions is about −0.02 pH units.

11. The method of claim 8, wherein the change in temperature is from about 20° C. to about 70° C.

12. The method of claim 8, wherein the change in temperature is from about 20° C. to about 50° C.

13. The method of claim 8, wherein dpKa/dT=dIP/dT±50%.

14. The method of claim 8, wherein the net charge of the polypeptide in the buffer selected in step d) changes by less than 0.5 over 30° C.

15. The method of claim 8, wherein the buffer selected in step d) is used in a chromatography at a concentration ranging from about 5 mM to about 250 mM.

16. The method of claim 8, wherein the buffer further comprises a salt.

17. The method of claim 16, wherein the salt is NaCl, KCl, $(NH_4)_2SO_4$, or $Na_2SO_4$.

18. The method of claim 16, wherein a concentration of the salt ranges from about 1 mM to about 1M.

19. A method for analyzing a composition, wherein the composition comprises a polypeptide and one or more contaminants, wherein the method effectively separates the polypeptide from the contaminants, the method comprising
  a) determining the optimal pH ion exchange separation condition according to the method of claim 8 and a temperature ion exchange separation condition for a plurality of compositions, each composition comprising a target polypeptide and one or more contaminants;
  b) binding each polypeptide and one or more contaminants from the compositions to an ion-exchange chromatography material using a loading buffer, wherein the loading buffer comprises a buffer selected by the method of claim 8;
  c) eluting the polypeptides and one more contaminants from the compositions from the ion-exchange chromatography material using a gradient of an elution buffer, wherein the elution buffer comprises the buffer and a salt, wherein a concentration of the salt increases in a gradient over time, wherein the polypeptides and the one or more contaminants of the compositions are separated by the gradient; and
  d) detecting the polypeptides and the one or more contaminants.

20. The method of claim 19, wherein a concentration of the buffer ranges from about 5 mM to about 20 mM.

21. The method of claim 19, wherein a pH of the buffer ranges from about 6.5 to about 8.5 at a temperature range of about 20° C. to about 70° C. or from about 6.5 to about 8.5 at a temperature range of about 20° C. to about 50° C.

22. The method of claim 19, wherein a pH of the buffer and the polypeptide at the inflection point is about 7.8 at about 22° C., about 7.5 at about 37° C., or about 7.2 at about 50° C.

23. The method of claim 19, wherein the salt gradient is a linear gradient or a step gradient.

24. The method of claim 19, wherein the salt gradient is a NaCl gradient, a KCl gradient, $(NH_4)_2SO_4$ gradient, or a $Na_2SO_4$ gradient.

25. The method claim 19, wherein the salt concentration in the gradient increases from about 0 mM to about 1M.

26. The method of claim 25, wherein the salt concentration increases from about 0 mM to about 100 mM in about 100 minutes or from about 0 mM to about 80 mM in about 40 minutes.

27. The method of claim 19, wherein the polypeptide is an antibody or immunoadhesin or fragment thereof.

28. The method of claim 27, wherein the antibody is a human antibody, a humanized antibody or a chimeric antibody.

29. The method of claim 27, wherein the antibody is an antibody fragment.

30. The method of claim 19, wherein the polypeptide is a monoclonal antibody or fragment thereof.

31. The method of claim 19, wherein the contaminant is a variant of the polypeptide.

32. The method of claim 19, wherein the contaminant is a degradation product of the polypeptide and/or a charge variant of the polypeptide.

33. The method of claim 19, wherein the chromatography material is a cation exchange chromatography material.

34. The method of claim 33, wherein the cation exchange chromatography material is a sulfonated chromatography material or a carboxylated chromatography material.

35. The method of claim 1, wherein the polypeptide is an antibody or immunoadhesin or fragment thereof.

36. The method of claim 35, wherein the antibody is an antibody fragment.

37. The method of claim 1, wherein the polypeptide is a monoclonal antibody or fragment thereof.

38. The method of claim 35 or 37, wherein the antibody is a human antibody, a humanized antibody or a chimeric antibody.

39. The method of claim 1, wherein the contaminant is a variant of the polypeptide.

40. The method of claim 1, wherein the contaminant is a degradation product of the polypeptide and/or a charge variant of the polypeptide.

41. A method for identifying an optimal ion exchange chromatography separation condition to analyze a composition comprising a polypeptide with one or more contaminants, the method comprising
  a) plotting a net charge versus pH curve at a selected temperature for the polypeptide based on an amino acid composition of the polypeptide, and b) determining an inflection point of the net charge versus pH curve at or near neutral pH by determining a second derivative of the curve of step a);

wherein the optimal ion exchange chromatography separation condition is a pH at about the inflection point for the polypeptide.

42. A method for analyzing a composition comprising a polypeptide and one or more contaminants, wherein the method effectively separates the polypeptide from the contaminants, the method comprising
   a) binding the polypeptide and one or more contaminants to an ion-exchange chromatography material using a loading buffer, wherein the loading buffer comprises a buffer, and performing chromatography; wherein a pH of the chromatography has been optimized for two or more target polypeptides by
      i) plotting a net charge versus pH curve at a selected temperature for each target polypeptide, wherein the curve is based on an amino acid composition of each polypeptide of the two or more target polypeptides, and
      ii) determining an inflection point of the net charge versus pH curve by determining a second derivative of the curves of step i); wherein an optimal ion exchange chromatography condition is a pH at a common inflection point for the two or more target polypeptides;
   b) eluting the polypeptide and one or more contaminants from the ion-exchange chromatography material using a gradient of an elution buffer, wherein the elution buffer comprises the buffer and a salt, wherein the polypeptide and the one or more contaminants are separated by the gradient; and
   c) detecting the polypeptide and the one or more contaminants.

43. The method of claim 42, wherein the buffer is identified by
   a) determining a change in the inflection point pH of the net charge versus pH curve with a change in a temperature (dIP/dT) for the two or more target polypeptides,
   b) selecting a buffer for which a change in an acid dissociation constant of the buffer with change in temperature (dpKa/dT) is essentially the same as the dIP/dT of the two or more target polypeptides.

44. The method of claim 43, wherein the buffer provides an effective buffer capacity at the inflection point pH.

* * * * *